US009067848B2

(12) United States Patent
Stadie et al.

(10) Patent No.: US 9,067,848 B2
(45) Date of Patent: Jun. 30, 2015

(54) NANOSTRUCTURED CARBON MATERIALS FOR ADSORPTION OF METHANE AND OTHER GASES

(71) Applicants: Nicholas P. Stadie, Pasadena, CA (US); Brent T Fultz, Pasadena, CA (US); Channing Ahn, Pasadena, CA (US); Maxwell Murialdo, Westminster, CA (US)

(72) Inventors: Nicholas P. Stadie, Pasadena, CA (US); Brent T Fultz, Pasadena, CA (US); Channing Ahn, Pasadena, CA (US); Maxwell Murialdo, Westminster, CA (US)

(73) Assignee: California Institute of Technology, Pasadena, CA (US)

( * ) Notice: Subject to any disclaimer, the term of this patent is extended or adjusted under 35 U.S.C. 154(b) by 120 days.

(21) Appl. No.: 14/050,755

(22) Filed: Oct. 10, 2013

(65) Prior Publication Data
US 2014/0113811 A1    Apr. 24, 2014

Related U.S. Application Data

(60) Provisional application No. 61/716,041, filed on Oct. 19, 2012.

(51) Int. Cl.
*B01J 20/02* (2006.01)
*B01J 20/20* (2006.01)
(Continued)

(52) U.S. Cl.
CPC ............... *C07C 9/04* (2013.01); *C07C 17/389* (2013.01); *C07C 29/76* (2013.01); *C07C 51/42* (2013.01);
(Continued)

(58) Field of Classification Search
CPC ............ B01D 53/02; B01D 2253/102; B01D 2253/31; B01D 2257/7025; B01D 2259/4525; B01J 20/00; B01J 20/20; C07C 17/389; C07C 29/76; C07C 51/42; C07C 9/04; C10L 2230/14; C10L 2270/10; C10L 3/06; Y02C 20/20
USPC ................ 95/90, 116, 143, 900, 903; 96/108; 502/400, 416, 439
See application file for complete search history.

(56) References Cited

U.S. PATENT DOCUMENTS

| 4,716,736 | A | 1/1988 | Schwarz |
| 4,752,310 | A | 6/1988 | Maier-Laxhuber et al. |

(Continued)

FOREIGN PATENT DOCUMENTS

| JP | 2004/093187 | 3/2004 |
| WO | WO 2014/062470 | 4/2014 |

OTHER PUBLICATIONS

Alcañiz-Monge (2009) "Fundamentals of methane adsorption in microporous carbons," *Microporous Mesoporous Mater.* 124:110-116.
(Continued)

*Primary Examiner* — Frank Lawrence
(74) *Attorney, Agent, or Firm* — Lathrop & Gage LLP

(57) ABSTRACT

Provided are methods for storing gases on porous adsorbents, methods for optimizing the storage of gases on porous adsorbents, methods of making porous adsorbents, and methods of gas storage of optimized compositions, as in systems containing porous adsorbents and gas adsorbed on the surface of the porous adsorbent. The disclosed methods and systems feature a constant or increasing isosteric enthalpy of adsorption as a function of uptake of the gas onto the exposed surface of a porous adsorbent. Adsorbents with a porous geometry and surface dimensions suited to a particular adsorbate are exposed to the gas at elevated pressures in the specific regime where n/V (density) is larger than predicted by the ideal gas law by more than several percent.

30 Claims, 23 Drawing Sheets

(51) Int. Cl.
| | |
|---|---|
| *C07C 9/04* | (2006.01) |
| *C07C 17/389* | (2006.01) |
| *C07C 29/76* | (2006.01) |
| *C07C 51/42* | (2006.01) |
| *B01J 20/00* | (2006.01) |
| *C10L 3/06* | (2006.01) |
| *B01D 53/02* | (2006.01) |

(52) U.S. Cl.
CPC .............. *C10L 2270/10* (2013.01); *B01J 20/00* (2013.01); *C10L 3/06* (2013.01); *C10L 2230/14* (2013.01); *B01D 53/02* (2013.01); *B01D 2253/102* (2013.01); *B01D 2253/31* (2013.01); *B01D 2257/7025* (2013.01); *B01D 2259/4525* (2013.01); *Y02C 20/20* (2013.01)

(56) References Cited

U.S. PATENT DOCUMENTS

| | | | |
|---|---|---|---|
| 4,881,376 | A | 11/1989 | Yonezawa et al. |
| 5,171,333 | A | 12/1992 | Maurer |
| 5,626,637 | A | 5/1997 | Baker |
| 7,250,074 | B2 | 7/2007 | Tonkovich et al. |
| 8,192,709 | B2 | 6/2012 | Reyes et al. |
| 2002/0023539 | A1 | 2/2002 | Tange et al. |
| 2002/0187896 | A1* | 12/2002 | Ryoo et al. ................. 502/418 |
| 2005/0202969 | A1 | 9/2005 | Kondo et al. |
| 2008/0207442 | A1 | 8/2008 | Pfeifer et al. |
| 2009/0273106 | A1 | 11/2009 | Lin et al. |
| 2009/0301902 | A1 | 12/2009 | Gogotsi et al. |
| 2010/0021366 | A1* | 1/2010 | Hu et al. ................. 423/445 R |
| 2011/0048063 | A1 | 3/2011 | Carruthers et al. |
| 2011/0052486 | A1 | 3/2011 | Ito et al. |
| 2011/0092362 | A1 | 4/2011 | Furuya et al. |
| 2011/0240491 | A1 | 10/2011 | Farone |
| 2012/0196745 | A1* | 8/2012 | Pak et al. ................... 502/439 |
| 2013/0337365 | A1* | 12/2013 | Pak et al. ................... 429/482 |
| 2014/0038816 | A1* | 2/2014 | Bakker et al. ............... 502/337 |

OTHER PUBLICATIONS

Al-Muhtaseb et al. (1999) "Roles of Surface Heterogeneity and Lateral Interactions on the Isosteric Heat of Adsorption and Adsorbed Phase Heat Capacity," *J. Phys. Chem. B*. 103:2467-79.

Aranovich et al. (1995) "Adsorption isotherms for microporous adsorbents," *Carbon*. 33:1369-75.

Aranovich et al. (1997) "Determining surface areas from linear adsorption isotherms at supercritical conditions," *J. Colloid Interface Sci*. 194:392-97.

Bénard et al. "Determination of the Adsorption Isotherms of Hydrogen on Activated Carbons above the Critical Temperature of the Adsorbate over Wide Temperature and Pressure Ranges," (2001) *Langmuir*. 17:1950-55.

Bhatia et al. (2006) "Optimum Conditions for Adsorptive Storage," *Langmuir*. 22:1688-700.

Blanco et al. (2010) "A Study of the Pore Size Distribution for Activated Carbon Monoliths and their Relationship with the Storage of Methane and Hydrogen," *Colloids and Surfaces: Physicochemical and Engineering Aspects*. 357:74-83.

Candelaria et al. (2012) "Nanostructured Carbon for Energy Storage and Conversion," *Nano Energy*. 1:195-220.

Chakraborty et al. (2008) "Thermodynamic trends in the uptake capacity of porous adsorbents on methane and hydrogen," *Appl. Phys. Lett*. 92:201911.

Chung et al. (2008) "Synthesis of Microporous Boron-Substituted Carbon (B/C) Materials Using Polymeric Precursors for Hydrogen Physisorption," *J. Am. Chem. Soc*. 130:6668-6669.

Cracknell et al. (1993) "Influence of Pore Geometry on the Design of Microporous Materials for Methane Storage," *J. Phys. Chem*. 97:494-99.

EFree Center (publication date unknown) "Anomalous isosteric enthalpy of adsorption of methane on xeolite-templated carbon," *EFree Center Geophysical Laboratory*. Washington, DC. <https://efree.gl.ciw.edu/content/anomalous-isosteric-enthalpy-adsorption-methane-xeolite-templated-carbon>.

Gallego et al. (Aug. 5, 2011) "Hydrogen Confinement in Carbon Nanopores: Extreme Densification at Ambient Temperature," *J. Am. Chem. Soc*. 133:13794-13797.

Guan et al. (Oct. 13, 2010) "Methane Storage in Carbon Pellets Prepared via a Binderless Method," *Energy Conversion and Management*.

He et al. (2005) "Monte Carlo Simulation and Pore-Size Distribution Analysis of the Isosteric Heat of Adsorption of Methane in Activated Carbon," *Langmuir*. 25:8297-8301.

Himeno et al. (2005) "High-Pressure Adsorption Equilibria of Methane and Carbon Dioxide on Several Activated Carbons," *Journal of Chemical and Engineering Data*. 50(2):369-376.

Huang (1972) "The Temperature Dependence of Isosteric Heat of Adsorption on the Heterogeneous Surface," *Journal of Catalysis*. 25:131-138.

International Search Report with Written Opinion corresponding to International Patent Application No. PCT/US2013/064253, mailed Dec. 24, 2013.

Jin et al. (2010) "Solution-Phase Synthesis of Heteroatom-Substituted Carbon Scaffolds for Hydrogen Storage," *J. Am. Chem. Soc*. 132:15246-15251.

Jin et al. (Jan. 5, 2011) "Nano-Engineered Spacing in Graphene Sheets for Hydrogen Storage," *Chem. Mater*. 23:923-925.

Kiyobayashi et al. (2002) "Hydrogen adsorption in carbonaceous materials—how to determine the storage capacity accurately," *J. Alloys Compd*. 330-332:666-669.

Lemmon et al. (2007) "NIST standard reference database 23: reference fluid thermodynamic and transport properties—REFPROP," No. Version 8.0 in Standard Reference Data Program.

Li et al. (Aug. 13, 2013) "Ultrahigh Gas Storage both at Low and High Pressures in KOH-Activated Carbonized Porous Aromatic Frameworks," *Scientific Reports*. 3:2420 (2013).

Lozano-Castello et al. (2002) "Advances in the Study of Methane Storage in Porous Carbonaceous Materials," *Fuel*. 81:1777-1803.

Lozano-Castello et al. (2002) "Influence of the Pore Size Distribution on Methane Storage at Relatively Low Pressure: Preparation of Activated Carbon with Optimum Pore Size," *Carbon*. 40:989-1002.

Ma et al. (2000) "Preparation of a High Surface Area Microporous Carbon Having the Structural Regularity of Y Zeolite," *Chem. Commun*. pp. 2365-2366.

Matranga et al. (1992) "Storage of natural gas by adsorption on activated carbon," *Chem. Eng. Sci*. 47:1569-79.

McCusker et al. (2001) "Nomenclature of structural and compositional characteristics of ordered microporous and mesoporous materials with inorganic hosts (IUPAC Recommendations 2001)," *Pure Appl. Chem*. 73(2):381-394.

McCusker et al. (2005) "IUPAC Nomenclature for Ordered Microporous and Mesoporous Materials and its Application to Non-zeolite Microporous Mineral Phases," *Reviews in Mineralogy and Geochemistry*. 57:1-16.

McNicholas et al. (2010) "H2 storage in microporous carbons from PEEK precursors," *J. Phys. Chem. C*. 114:13902-08.

Mertens (2009) "Determination of absolute adsorption in highly ordered porous media," *Surf. Sci*. 603:1979-84.

Mosher (2011) "The Impact of Pore Size on Methane and $CO_2$ Adsorption in Carbon," Master's Thesis, Stanford University.

Myers et al. (1997) "Comparison of molecular simulation of adsorption with experiment," *Adsorption*. 3:107-15.

Nicholson (1998) "Simulation studies of methane transport in model graphite micropores," *Carbon*. 36:1511-1523.

Nishihara et al. (2009) "High-pressure hydrogen storage in zeolite-templated carbon," *J. Phys. Chem. C*. 113:3189-3196.

Nishihara et al. (Jul. 16, 2012) "Templated nanocarbons for energy storage," *Adv. Mater*. 24:4473-98.

Olsen (May 2011) "Investigations of novel hydrogen adsorption phenomena," Ph.D.thesis. University of Missouri—Columbia.

Ortiz (Dec. 2012) "Computational Studies of Methane Adsorption in Nanoporous Carbon," Master's Thesis. University of Missouri—Columbia.

(56) References Cited

OTHER PUBLICATIONS

Panella et al. (2005) "Hydrogen Adsorption in Different Carbon Nanostructures," *Carbon.* 43:2209-2214.

Poirier et al. (2001) "Hydrogen adsorption in carbon nanostructures," *Int. J. Hydrogen Energ.* 26:831-35.

Purewal et al. (2009) "Pore size distribution and supercritical hydrogen adsorption in activated carbon fibers," *Nanotechnology.* 20:204012.

Purewal et al. (Sep. 13, 2012) "Improved hydrogen storage and thermal conductivity in high-density MOF-5 composites," *J. Phys. Chem. C.* 116:20199-20212.

Saha et al. (2008) "Equilibrium, kinetics, and enthalpy of hydrogen adsorption in MOF-177," *Int. J. Hydrogen Energy.* 33:7479-88.

Sakintuna et al. (2004) "Templated Synthesis of Porous Carbons and Flower-Like Carbon Fluorides Using Natural Zeolite," *Prep. Pap.- Am. Chem. Soc., Div. Duel Chem.* 49(2):696-697.

Salem et al. (1998) "Thermodynamics of high-pressure adsorption of argon, nitrogen, and methane on microporous adsorbents," *Langmuir.* 14:3376-3389.

Sillar et al. (Sep. 12, 2012) "Ab initio prediction of adsorption isotherms for small molecules in metal-organic frameworks: the effect of lateral interactions for methane/CPO-27-Mg." *J. Am. Chem. Soc.* 134(44):18354-18365.

Sircar (1999) "Gibbsian surface excess for gas adsorption—revisited," *Ind. Eng. Chem. Res.* 38:3670-82.

Sircar et al. (1999) "Isosteric Heat of Adsorption: Theory and Experiment," *J. Phys. Chem. B.* 103:6539-46.

Stadie (Nov. 5, 2012) "Synthesis and thermodynamic studies of physisorptive energy storage materials," Ph.D. thesis, California Institute of Technology.

Stadie et al. (2010) "Measurements of hydrogen spillover in platinum doped superactivated carbon," *Langmuir.* 26:15481-85.

Stadie et al. (2012) "Zeolite-templated carbon materials for high-pressure hydrogen storage," *Langmuir.* 28:10057-10063.

Stadie et al. (Dec. 23, 2012) "Anomalous Isosteric Enthalpy of Adsorption of Methane on Zeolite-Templated Carbon," *J. Am. Chem. Soc.* 135:990-993.

Sun et al. (2009) "Principles of methane adsorption and natural gas storage," *Adsorption.* 15:133-37.

Tarazona et al. (1987) "Phase equilibria of fluid interfaces and confined fluids," *Mol. Phys.* 60:573-95.

Terrones et al. (1997) "Quasiperiodic icosahedral graphite sheets and high-genus fullerenes with nonpositive Gaussian curvature," *Phys. Rev. B.* 55:9969-9974.

Voskuilen et al. (2012) "Hydrogen adsorption on microporous materials at ambient temperatures and pressures up to 50 MPa," *Adsorption.* 18:239-49.

Wang et al. (Apr. 27, 2011) "Experimental and Theoretical Study of Methane Adsorption on Granular Activated Carbons," *AIChE Journal.* 58(3):782-788.

Xia et al. (2009) "Hydrogen storage in high surface area carbons: experimental demonstration of the effects of nitrogen doping," *J. Am. Chem. Soc.* 131:16493-99.

Xia et al. (2013) "Facile preparation of hierarchically porous carbons from metal-organic gels and their application in energy storage," *Scientific Reports.* 3:1935.

Xia et al. (Apr. 10, 2013) "Porous Carbon-Based Materials for Hydrogen Storage: Advancements and Challenges," *J. Mater. Chem. A.* 1:9365-9381.

Yang et al. (2007) "Enhanced hydrogen storage capacity of high surface area zeolite-like carbon materials," *J. Am. Chem. Soc.* 129:1673-1679.

Zhou et al. (2009) "Fundamentals of High Pressure Adsorption," *Langmuir.* 25:13461-13466.

\* cited by examiner

Pore cross-sectional dimension

Inter-pore spacing dimension

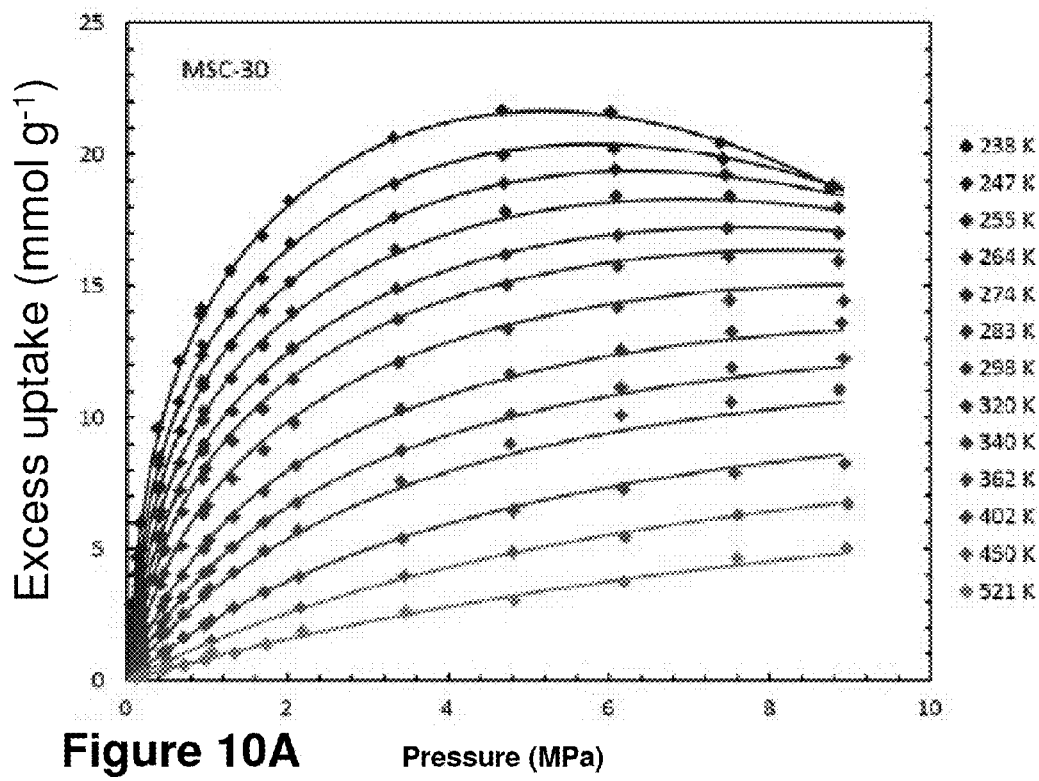
Figure 10A Pressure (MPa)
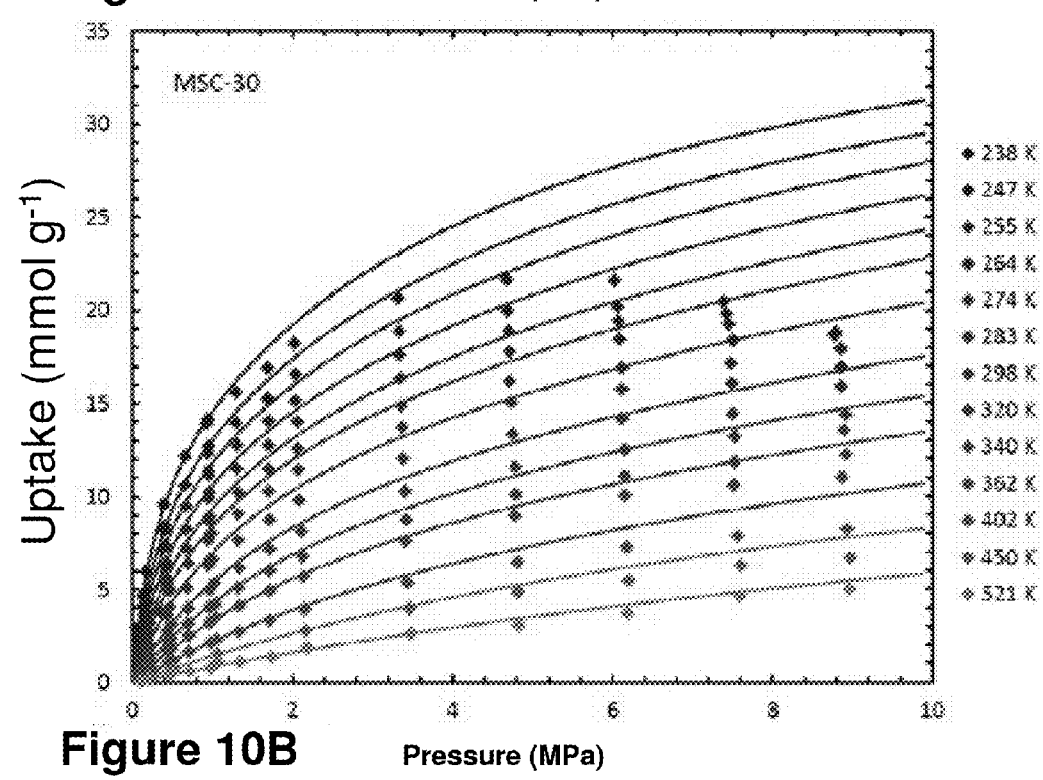
Figure 10B Pressure (MPa)

NANOSTRUCTURED CARBON MATERIALS FOR ADSORPTION OF METHANE AND OTHER GASES

CROSS REFERENCE TO RELATED APPLICATION

This application claims the benefit of and priority to U.S. Provisional Application 61/716,041, filed Oct. 19, 2012, which is hereby incorporated by reference in its entirety.

STATEMENT REGARDING FEDERALLY SPONSORED RESEARCH OR DEVELOPMENT

This invention was made with government support under Grant No. DE-SG0001057/T-105949 awarded by the Department of Energy. The government has certain rights in the invention.

BACKGROUND

This invention is in the field of gas storage technology. This invention relates generally to materials and methods for improved adsorption of methane and other gases on porous adsorbents.

Unlike that of liquids, which typically possess a relatively high density, the density of gases is relatively low. This provides a challenge for high-density storage of chemical species that possess a condensation temperature or critical temperature below common environmental temperatures.

Methods are available, however, for storage of gases at densities higher than at standard pressure and temperature conditions. For example, gases can be stored in a compressed state. Compressed gases, however, still do not possess a density as high as liquids and typically require heavy and bulky storage tanks.

Additionally, some gases can be compressed into a liquid state at standard temperature conditions. For example, propane and propane/butane mixtures are commonly compressed to a liquid state for storage and transport. Such a technique for liquefaction cannot generally be used for gases such as hydrogen and methane, however, because they have critical temperatures well below common environmental temperatures.

To overcome this limitation, gases are sometimes cooled to low or cryogenic temperatures to achieve liquefaction. For example, natural gas is commonly cooled to a liquid state for storage and transport, though this typically requires considerable insulation and cooling systems to maintain the cold temperatures for long periods of time.

Gas storage in compressed systems can also be enhanced by adsorption of the gas onto the surface of an adsorbent material. For example, Himeno et al., *Journal of Chemical and Engineering Data*, 50:2, 369-376 (2005), discloses the use of various microporous activated carbons for adsorption of gases such as methane and carbon dioxide.

More recently, U.S. Patent Application Publication US 2011/0052486 discloses microporous carbon materials for use in hydrogen and methane storage applications. Additionally, Stadie et al., *Langmuir*, 28, 10057 (2012) discloses zeolite-templated carbon materials for use in hydrogen storage applications. Also, Nishihara et al., *Advanced Materials*, 24, 4473-4498 (2012), discloses a variety of templated nanoporous carbon materials for use in hydrogen storage applications.

In *Scientific Reports* 3, 1935 (2013) and *Scientific Reports* 3, 2420 (2013), Xia et al. and Li et al. respectively disclose methods for forming porous carbon materials from metal-organic gel templates for hydrogen storage and carbonized porous aromatic frameworks for storage of methane, hydrogen and carbon dioxide.

There remains, however, a need for enhanced gas storage materials and methods.

SUMMARY

Inter-molecular interactions occur in gases at high pressures, when the ideal gas equation $n/V=P/RT$ is no longer an accurate predictor of the density, $n/V$ (P is pressure, T is temperature, R is the gas constant, n is the number of molecules/atoms and V is volume). Attractive inter-molecular interactions cause the density of the gas to be higher than predicted by the ideal gas equation, and in this regime surface adsorption can be altered by tailoring the inner geometry (porous structure) of the adsorbent. At high fractional coverages of gas molecules on the surface, the distances between molecules and characteristic intermolecular attractions alter the isosteric heat of adsorption, and therefore the capacity of the materials to adsorb the gas at a given temperature and pressure. Different types of gases have different intermolecular interactions, and different porous geometries can be selected to control the amount of gas adsorption at high adsorption densities, giving a rich set of design parameters for engineering service. In one embodiment, an adsorbent with a porous geometry and surface dimensions suited to a particular adsorbate is exposed to the gas at elevated pressures in the specific regime where $n/V$ is larger than predicted by the ideal gas equation by more than several percent, for example.

The invention provides methods, materials and systems for storing, releasing and/or providing a source of a gas or mixture of gases, for example, involving porous adsorbents having chemical and physical properties selected to achieve a large adsorptive uptake and efficient release of compressed gases. In some embodiments, for example, the methods, materials and systems of the invention include microporous and/or mesoporous adsorbents having a network of pore structures characterized by a pore size distribution providing thermodynamic properties useful for deliverable storage of compressed gases for industrial processes such as energy storage and production, gas separation and adsorption refrigeration. In some embodiments, for example, the invention provides methods of designing and/or characterizing adsorbent materials to achieve adsorptive properties useful for gas storage, for example, via classification of thermodynamic properties such as isosteric enthalpy of adsorption. In certain embodiments, methods, materials and systems of the invention include porous carbon materials having pore dimensions, ordering and physical properties selected to acheive adsorption of large amounts of gaseous fuels or mixtures of gaseous fuels and additives.

Provided are methods for storing a gas, for example for storing a gas on a porous adsorbent. In an embodiment, a method of this aspect comprises the steps of: selecting a porous adsorbent having a first chemical composition; determining a first pore size distribution for the porous adsorbent having the first chemical composition, wherein the first pore size distribution provides a constant or increasing isosteric enthalpy of adsorption as a function of uptake of the gas on an exposed surface of the porous adsorbent; providing the porous adsorbent having a first plurality of ordered pore structures characterized by the first pore size distribution; and contacting the porous adsorbent with the gas at a pressure sufficient to achieve adsorption of the gas on the porous adsorbent characterized by the constant or increasing isosteric enthalpy of adsorption as a function of uptake of the gas, thereby storing the gas on the porous adsorbent.

In embodiments, a constant or increasing enthalpy of adsorption, such as an isosteric enthalpy, as a function of uptake provides a number of advantages. For example, when the enthalpy of adsorption increases as a function of uptake, this results in an increased or sustained rate of uptake of the gas by the porous adsorbent. In some embodiments, an increasing enthalpy of adsorption as a function of uptake results in relatively lower pressures required to uptake the same amount of gas when compared to systems featuring a decreasing enthalpy of adsorption. In some embodiments, an increasing enthalpy of adsorption as a function of uptake is achieved by favorable interactions, such as an attractive interaction, between molecules or atoms of the gas adsorbed on the exposed surface of the porous adsorbent. In a specific embodiment, for example, the first pore size distribution provides the isosteric enthalpy of adsorption that increases as a function of uptake of the gas by at least 0.01 kJ mol$^{-1}$/mmol g$^{-1}$ or that increases a total amount of 1 kJ mol$^{-1}$ or more, for example, between two pressures or uptake amounts.

In an embodiment, for example the step of determining the first pore size distribution comprises steps of: providing the porous adsorbent; contacting the porous adsorbent with the gas at a pressure sufficient to achieve adsorption of the gas onto the exposed surface of the porous adsorbent; and measuring the isosteric enthalpy of adsorption of the gas as a function of uptake of the gas by the porous adsorbent to establish that the first pore size distribution provides the constant or increasing isosteric enthalpy of adsorption as a function of uptake of the gas on the exposed surface of the porous adsorbent.

Methods of this aspect optionally further comprise a step of determining a slope of the isosteric enthalpy of adsorption of the gas as a function of uptake of the gas by the porous adsorbent, a step of generating a plot of the isosteric enthalpy of adsorption of the gas as a function of uptake of the gas by the porous adsorbent or a step of computing a regression analysis of the isosteric enthalpy of adsorption of the gas as a function of uptake of the gas by the porous adsorbent, such as, for example, a linear regression or a quadratic regression. Such steps, for example, provide for determination of whether the porous adsorbent provides the constant or increasing isosteric enthalpy of adsorption as a function of uptake.

Optionally, the step of measuring the isosteric enthalpy of adsorption comprises measuring a plurality of gas adsorption isotherms for a plurality of selected temperatures. In an embodiment, for example, each gas adsorption isotherm is measured by exposing the porous adsorbent to a plurality of pressures and measuring an amount of uptake of the gas by the porous adsorbent after the porous adsorbent is allowed to come to thermal equilibrium to a selected temperature for each of the plurality of pressures.

In an exemplary embodiment, the isosteric enthalpy of adsorption is computed using the equation $$-\Delta H_{ads}(n_a) = -T\left(\frac{\partial P}{\partial T}\right)_{n_a}(\Delta v_{ads}),$$

where $-\Delta H_{ads}(n_a)$ is an isosteric enthalpy of adsorption at a specific uptake amount $n_a$, T is temperature, P is pressure, $$\left(\frac{\partial P}{\partial T}\right)_{n_a}$$

is a slope of a relationship between pressure and temperature for adsorption of the gas by the porous adsorbent evaluated at the specific uptake amount $n_a$ and $\Delta v_{ads}$ is a change in molar volume of the gas upon adsorption.

Optionally, the step of measuring the isosteric enthalpy of adsorption comprises steps of adsorbing a known uptake amount of the gas on the exposed surface of the adsorbent material and measuring a heat quantity released by the known uptake amount of the gas upon adsorption. For example, in an embodiment, the step of measuring a heat quantity comprises measuring a temperature change of the porous adsorbent upon adsorption of the known uptake amount of the gas.

In embodiments, for example, methods of this aspect further comprise a step of empirically characterizing isosteric enthalpy of adsorption values for a range of pore size distributions for the porous adsorbent. In embodiments, for example, methods of this aspect further comprise a step of empirically characterizing isosteric enthalpy of adsorption values for a range of porous adsorbents having different chemical compositions. Optionally, the step of empirically characterizing isosteric enthalpy of adsorption values further comprises measuring an X-ray diffraction pattern of the porous adsorbent or measuring an electron micrograph image of the porous adsorbent.

In embodiments, for example, methods of this aspect further comprise a step of determining the first pore size distribution. Optionally, the step of determining the first pore size distribution comprises calculating a density functional theory model (DFT) of the porous adsorbent for a number of candidate pore size distributions or calculating a Lennard-Jones potential for a system comprising the porous adsorbent and the gas; or wherein the step of determining the first pore size distribution or characterizing the porosity comprises using an empirical method selected from the group consisting of the MP (micropore) method, the $\alpha_s$-method, the DR (Dubinin-Radushkevich) or DA (Dubinin-Astakhov) method, the Dubinin-Stoekli method, the Horvah-Kawazoe method, the BJH method and the Nguyen-DO (ND) method and semi-empirical methods using non-localized DFT (NLDFT) or grand-canonical Monte Carlo (GCMC) simulations.

Optionally, the gas comprises one or more of: $CO_2$, CO, $H_2O$, natural gas, $H_2$, $CH_4$, $C_2H_4$, $C_2H_2$, $C_3H_8$, $C_3H_6$, $C_4H_{10}$, $C_5H_{12}$, $C_5H_{10}$, $C_6H_{14}$, $C_6H_{12}$, $C_6H_6$, $CH_3OH$, $C_2H_5OH$, $C_3H_7OH$, $CH_3Cl$, $CH_2Cl_2$, $CHCl_3$, $CCl_4$, HCl, HF, $BH_3$, $B_2H_6$, $BF_3$, $BCl_3$, HCOOH, $O_2$, $O_3$, HOOH, $H_2S$, any deuterated form of these, any partially deuterated form of these, $N_2$, CN, $N_2O$, Ne, Xe, Kr, $SiH_4$, $CF_4$, $CCl_4$, $SF_6$, $SiF_4$, $CS_2$. In a specific embodiment, the gas comprises methane ($CH_4$).

In embodiments, for example, the gas comprises a first gas and one or more additive gases. Optionally, adsorption of the one or more additive gases onto the exposed surface of the porous adsorbent provides the constant or increasing isosteric enthalpy of adsorption as a function of uptake of the gas. In various embodiments, the first gas comprises methane and the one or more additive gases are selected from the group consisting of $C_2H_6$, $C_2H_4$, $C_2H_2$, $C_3H_8$, $C_3H_6$, $C_4H_{10}$, $C_5H_{12}$, $C_5H_{10}$, $C_6H_{14}$, $C_6H_{12}$, $C_6H_6$, CO, $CO_2$, $H_2O$, $H_2$, Ne, Xe, Kr, $B_2H_6$, $SiH_4$, $CF_4$, $CCl_4$, $SF_6$, $SiF_4$, and $CS_2$.

In some embodiments, for example, the contacting step comprises contacting the exposed surface of the porous adsorbent to the gas at a temperature within in the range of −70° C. to 100° C. or within the range of −169° C. to 125° C.

In a specific embodiment, the contacting step comprises contacting the exposed surface of the porous adsorbent to the gas at a temperature greater than a critical temperature of the gas, at a pressure greater than the critical pressure of the gas or at both a temperature greater than a critical temperature of the gas and a pressure greater than the critical pressure of the gas. Optionally, the contacting step comprises contacting the exposed surface of the porous adsorbent to the gas at a pressure greater than atmospheric pressure. In embodiments, for example, the contacting step comprises contacting the exposed surface of the porous adsorbent to the gas at a pressure greater than or equal to 1 MPa, greater than or equal to 10 MPa, greater than or equal to 30 MPa, greater than or equal to 70 MPa or selected from the range of 0.1 MPa to 12 MPa.

In some embodiments, for example, the porous adsorbent has the first chemical composition comprising elements selected from the group consisting of hydrogen, boron, carbon, nitrogen, oxygen, a halogen, an alkali metal, an alkaline earth metal, a noble metal and any combination of these. Optionally, the first chemical composition comprises a carbonaceous material. Optionally, the first chemical composition comprises graphitic carbon, graphene, HOPG, amorphous carbon, carbon black, coke, carbon nanotubes, fullerenes, activated carbon, superactivated carbon, carbon aerogel, template carbon, intercalated graphite or any combinations of these. In a specific embodiment, for example, the first chemical composition comprises $sp^2$-hybridized carbon. In specific embodiments, the first chemical composition comprises zeolite templated carbon, porous aluminosilicate-templated carbon or mesoporous silica-templated carbon.

Optionally, the porous adsorbent comprises a microporous material. Optionally, the porous adsorbent comprises a mesoporous material. In embodiments, for example, the first pore size distribution comprises unimodal distribution with a mean pore cross sectional dimension selected from the range of 0.4 nm to 2.6 nm. Optionally, the first pore size distribution comprises a unimodal distribution with a pore cross sectional dimension standard deviation less than 0.5 nm. Optionally, the first pore size distribution comprises a mean inter pore spacing dimension selected from the range of 1 nm to 5 nm. Optionally, the first pore size distribution comprises an inter pore spacing dimension standard deviation less than 0.5 nm. A range of pore geometries are useful for porous adsorbents of the present invention including slits, cylinders, channels and grooves. In some embodiments, pores of adsorbent materials of the invention have a cross sectional shape selected from the group consisting of circular, ellipsoidal, rectangular, square, triangular, hexagonal, and combinations of these.

Optionally, the inter-pore spacing is regular, single mode or random. For example, in certain embodiments, the inter-pore spacing dimension is regular and single mode, such as provided by one or more zeolite-templated carbonaceous materials. In certain embodiments, the inter-pore spacing dimension is optimized to provide enhanced specific surface area to a porous adsorbent. For example, in embodiments, the inter-pore spacing dimension is minimized to provide for an increased total number of pores in a porous adsorbent.

In embodiments, the porous adsorbent has a specific surface area selected from the range of $100\ m^2\ g^{-1}$ to $6000\ m^2\ g^{-1}$ or selected from the range of $1000\ m^2\ g^{-1}$ to $4000\ m^2\ g^{-1}$. Optionally, the pore structures of the porous adsorbent are provided in an ordered network. For example, in embodiments, the ordered network is a connected (continuous) or unconnected lattice comprising channels in one or more of the following patterns: 1D (unconnected), 2D simple square, 2D hexagonal, 2D other, 3D simple cubic, 3D hexagonal, or 3D other, where the dimensionality refers to the connectedness of a channel network. For further example, in embodiments, the ordered network of pores is a connected (continuous) or unconnected lattice comprising slits in one or more of the following patterns: 1D (unconnected, as in layers of graphite) or 2D connected slits (as in pores between aligned pillars). In any of the above mentioned embodiments, slit pores or channels optionally exist in one or more ordered widths and/or are separated by one or more ordered widths. Optionally, ordered width slit pore and/or channel networks exist in disordered 1D, 2D or 3D arrays.

Optionally, at least a portion of the pore structure confines gas adsorbed onto the exposed surface of the porous adsorbent in one, two or three dimensions. For example, in an embodiment at least a portion of the pore structure comprises a channel structure, for example, providing confinement in one or two dimensions. In a specific embodiment, a carbon nanotube system provides a channel structure. In an embodiment, for example, at least a portion of the pore structure comprises, at least in part, a box structure, a cage or cage-like structure or a perforated spherical structure, for example, providing confinement in two or three dimensions. In an embodiment, for example, box structures, cages or cage-like structures are connected by channels. In an embodiment, for example, a box structure, a cage or cage-like structure or a perforated spherical structure provides a plurality of active adsorption sites, such as in the corners of a box, cage or cage-like structure. Optionally, openings are provided in the box, cage or cage-like structures providing a pathway for gas atoms or molecules to pass in, out and/or between the box, cage or cage-like structures, for example between adjacent structures. In a specific embodiment, a zeolite-templated carbon provides a cage or cage-like structure connected by channels. In a specific embodiment, a perforated fullerene provides a perforated cage-like structure.

In a specific embodiment, the first chemical composition comprises a zeolite-templated carbon, wherein the gas comprises methane and wherein the first pore size distribution comprises a mean pore cross sectional selected from the range of 0.8 nm to 1.4 nm and a pore cross sectional dimension standard deviation less than 0.3 nm.

Optionally, the constant or increasing isosteric enthalpy of adsorption varies between 2 kJ mol$^{-1}$ and 48 kJ mol$^{-1}$, between 10 kJ mol$^{-1}$ and 40 kJ mol$^{-1}$, between 16 kJ mol$^{-1}$ and 32 kJ mol$^{-1}$ or wherein the isosteric enthalpy exhibits an increase amount between 0.2 kJ mol$^{-1}$ and 6 kJ mol$^{-1}$. In a specific embodiment, for example, the constant or increasing isosteric enthalpy of adsorption as a function of uptake of the gas occurs at a fractional coverage of the exposed surface selected from the range of 0% to 60% or from the range of 10% to 50%. In a specific embodiment, for example, the constant or increasing isosteric enthalpy of adsorption as a function of uptake occurs for pressures of the gas selected from the range of 0.01 MPa to 10 MPa or for pressures of the gas selected from the range of 0.01 MPa to 3 MPa. Optionally, the constant or increasing isosteric enthalpy of adsorption as a function of uptake occurs for temperatures of the gas selected from the range of −70° C. to 0° C. or selected from the range of −50° C. to 25° C. The pressure and temperature range of optimal adsorption on the surface of a tuned porous adsorbent material is optionally determined by examining the real gas density of the pure gas or gas mixture of the desired adsorbate. In an embodiment, the temperature is fixed at a value that is suitable for the application (for example, near room temperature) but where non-ideal gas behaviour is significant. In embodiments, the density of the gas phase at this temperature, as a function of pressure, optimally has a pressure range over which the density is 0-50% or 20-200% that of the ideal gas in the same conditions. In an embodiment, pure methane is stored at −40° C. where the ideal pressure range of adsorption is 3-30 MPa.

In a specific embodiment, the constant or increasing isosteric enthalpy of adsorption provides for reversible uptake or release of the gas adsorbed onto the exposed surface as the pressure is varied.

Optionally, the gas is adsorbed onto the exposed surface to an absolute uptake amount selected from the range of 0.5 mmol g$^{-1}$ to 50 mmol g$^{-1}$. Optionally, the gas is adsorbed onto the exposed surface to an excess uptake amount selected from the range of 0.5 mmol g$^{-1}$ to 50 mmol g$^{-1}$. In an exemplary embodiment, a deliverable gravimetric gas capacity of the porous adsorbent material is selected from the range of 1 to 20 weight percent or selected from the range of 5 to 60 weight percent. In some embodiments, the term weight percent refers to the weight of gas stored by a gas storage system divided by the total weight of the adsorbent plus stored gas.

Exemplary method embodiments of this aspect further comprise a step of releasing the gas stored on the porous adsorbent. Optionally, the releasing step comprises reducing the pressure of the gas. Optionally, the releasing step comprises increasing a temperature of the porous adsorbent.

In an embodiment, for example, the step of providing the porous adsorbent comprises the steps of: providing a porous template material comprising a second plurality of ordered pore structures having a second pore size distribution; exposing the porous template material to a first chemical composition precursor to create a porous template material and first chemical composition precursor mixture; converting the first chemical composition precursor to the first chemical composition, thereby creating a porous template material and first chemical composition mixture; and removing the porous template material from the porous template material and first chemical composition mixture, thereby creating the porous adsorbent.

Optionally, the porous template material comprises a zeolite. In a specific embodiment, the first chemical composition comprises carbon and the first chemical composition precursor comprises a liquid organic compound. In specific embodiments, for example, the step of converting the first chemical composition precursor to the first chemical composition precursor comprises polymerizing and carbonizing the first chemical composition precursor. Optionally, the porous template material comprises silicon. Optionally, the porous template material comprises silica. In some embodiments, for example, the step of providing the porous template material comprises forming the second plurality of ordered pore structures in a template base material. Optionally, the template base material comprises a non-porous material and the step providing the porous template material comprises porating the non-porous material.

In another aspect, provided are methods of making a porous adsorbent, such as, for example, a porous adsorbent having a first chemical composition. A specific embodiment of this aspect comprises the steps of determining a first pore size distribution for the porous adsorbent, wherein the first pore size distribution provides a constant or increasing isosteric enthalpy of adsorption as a function of uptake of the gas on an exposed surface of the porous adsorbent; providing a porous template material comprising a first plurality of ordered pore structures having a second pore size distribution; exposing the porous template material to a first chemical composition precursor to create a porous template material and first chemical composition precursor mixture; converting the first chemical composition precursor to the first chemical composition, thereby creating a porous template material and first chemical composition mixture; and removing the porous template material from the porous template material and first chemical composition mixture, thereby creating the porous adsorbent.

In another embodiment, provided are stored gas compositions. In embodiments, a stored gas composition comprises a porous adsorbent and a gas adsorbed on an exposed surface of the porous adsorbent. In an embodiment, the porous adsorbent has a first chemical composition and a first plurality of ordered pore structures characterized by a first pore size distribution. In a specific embodiment, for example, the first pore size distribution provides a constant or increasing isosteric enthalpy of adsorption as a function of uptake of the gas on the exposed surface of the porous adsorbent for a pressure of the gas exposed to the porous adsorbent selected from the range of 0.1 MPa to 12 MPa and at a temperature the range of −169° C. to 125° C.

In an embodiment, the gas is adsorbed on the exposed surface of the porous adsorbent to an absolute uptake amount selected from the range of 2 mmol g$^{-1}$ to 50 mmol g$^{-1}$. Optionally, the gas is adsorbed on the exposed surface of the porous adsorbent to an excess uptake amount selected from the range of 2 mmol g$^1$ to 25 mmol g$^{-1}$ or to an absolute or excess uptake amount greater than 5 mmol g$^{-1}$. Optionally, the gas is adsorbed on the exposed surface of the porous adsorbent at a monolayer level or a sub-monolayer level. Optionally, the gas is adsorbed on the exposed surface of the porous adsorbent at a multilayer level. In specific embodiments, for example, a deliverable gravimetric amount of gas adsorbed on the exposed surface of the porous adsorbent is selected from the range selected from the range of 1 to 50 weight percent or selected from the range of 20 to 100 weight percent.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

BRIEF DESCRIPTION OF THE DRAWINGS

FIGS. 10A-10F illustrates adsorption data sets for various adsorbents fitted to a double-Langmuir equation as a function of pressure (MPa).

(FIG. 11A) with the ideal gas assumption, and (FIG. 11B) with the real gas density.

DETAILED DESCRIPTION

Figure 1A:
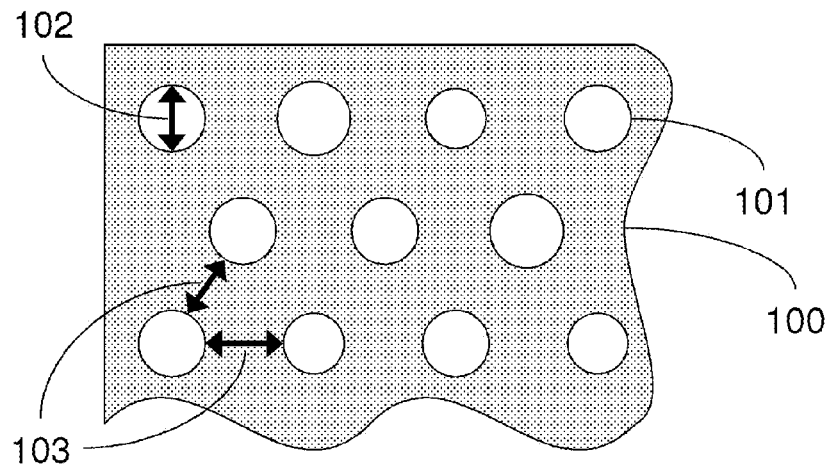
FIG. 1A provides a schematic illustration of a porous adsorbent showing various elements of a pore size distribution embodiment.

In general the terms and phrases used herein have their art-recognized meaning, which can be found by reference to standard texts, journal references and contexts known to those skilled in the art. The following definitions are provided to clarify their specific use in the context of the invention.

"Porous adsorbent" refers to a material comprising a plurality of pores which can support adsorption of an adsorbate material, such as a gas.

"Enthalpy of adsorption" refers to the change in heat of a system upon the adsorption of a gaseous molecule or atom onto the surface of an adsorbent. "Isosteric enthalpy of adsorption" refers to a specific enthalpy of adsorption expressed as a positive value when heat is released in the process of adsorption.

"Uptake" and "uptake amount" refer to an amount of adsorbate present on the surface of an adsorbent or in the adsorbed phase. "Absolute uptake" refers to a total amount of adsorbate present on the surface of an adsorbent or in the adsorbed phase. "Excess uptake" refers to an amount of adsorbate present on the surface of an adsorbent in excess of the gas density within the entire void volume of the volume containing the adsorbent. In an embodiment, excess uptake provides a quantitative measure of the ability of the adsorbent to adsorb gas onto a surface of the adsorbent beyond the concentration of gas that would present in the absence of the adsorbent.

"Deliverable gravi metric gas capacity" refers to the difference in the amount of gas contained by a gas storage system per unit mass or weight of the entire gas storage system between two pressures. For example, in embodiments, deliverable gravi metric gas capacity provides the amount of deliverable gas in a gas storage system between the minimum pressure required for the application (e.g., 0.3 MPa for delivery to a fuel cell) and the maximum pressure of the storage system, such as defined by the tank specifications.

"Adsorption" or "physisorption" refers to the physical phenomenon of atoms, ions or molecules becoming physically associated with (attracted to) a surface. In embodiments, adsorption of atoms, ions or molecules to a surface is characterized as such, where, for example, weak van der Waals forces are the primary driving force for the association with the surface. Adsorption contrasts with chemisorption, for example, where chemical bonding is the primary driving force for the association with the surface. Adsorption processes are characterized by a number of thermodynamic and kinetic parameters, including, but not limited to, an adsorption enthalpy.

"Gas adsorption isotherm" refers to a measurement of the amount of gas adsorbed to an adsorbent surface as a function of pressure at a single constant temperature. In embodiments, the amount of gas is expressed as a unit of number of gas molecules (e.g., mmol) per mass of the adsorbent, or as mass of gas per combined mass of the gas and the adsorbent (e.g., wt %).

"Pore size distribution" refers to statistical characteristics of a plurality of pores. In embodiments, a pore size distribution comprises a mean pore dimension, such as a pore cross sectional dimension or a pore diameter. In embodiments, a pore size distribution comprises a measure of the variability of a pore dimension, such as a standard deviation of the pore cross sectional dimension or the pore diameter. In embodiments, a pore size distribution comprises a measure of the distribution of the pores in space. For example, in embodiments, a pore size distribution comprises a mean inter pore spacing dimension and/or an inter pore spacing dimension variation, such as a standard deviation. The phrase "inter pore spacing dimension" refers to a measure of the length between two adjacent pores. In embodiments, the inter pore spacing dimension is the length between sidewalls of two adjacent pores. In embodiments, the inter pore spacing dimension is a center-to-center distance between two adjacent pores.

"Ordered network" refers to a spatial distribution in space of a plurality of pores. In embodiments, an ordered network of pores comprises a uniform array of pores. In embodiments, an ordered network of pores comprises a plurality of pores having a narrow cross sectional pore dimension and inter pore spacing dimension variation, such as a deviation of less than 0.5 nm in both quantities.

"Additive gas" refers to a minor component of a gas mixture. In embodiments, an additive gas is specifically included in a gas mixture for the purposes of impacting the adsorption thermodynamics or kinetics of adsorption of another component of the gas mixture.

"Carbonaceous material" refers to a composition or structure comprising carbon, for example graphitic carbon, graphene, amorphous carbon, carbon black, coke, carbon nanotubes, fullerenes, etc. In embodiments, a carbonaceous material comprises various other elements provided as dopants or impruities. In embodiments, a carbonaceous material comprises other elements, such as hydrogen, beryllium, boron, nitrogen, oxygen or phosphorus, for example substituted into the covalent bonding network of the carbonaceous material in place of a carbon atom or remaining as an additional functional group on the surface.

"Zeolite-templated carbon" refers to a carbonaceous material in which the structure is based on the structure of a zeolite. In embodiments, a zeolite-templated carbon comprises the remaining material after pores of a zeolite are filled with a carbonaceous material and then the zeolite material is removed. In embodiments, the pores of a zeolite material are filled with a carbonaceous material, for example, by first filling the pores with an organic compound and then polymerizing and/or carbonizing the organic compound to convert the organic compound into a carbonaceous material. In embodiments, a zeolite-templated carbon has a porous structure in which the network of pores are located at positions of the template zeolite where the zeolite material was originally located. In embodiments, zeolite-templated carbon has a porous structure in which the carbonaceous material is located at positions of the template zeolite where pores of the zeolite material were originally located.

"Zeolite" refers to an alumino-silicate porous material in which the pores are ordered in a characteristic arrangement or framework specific to the composition or crystal structure of the material. In a specific embodiment, a zeolite is a microporous material. Exemplary zeolite structures include, but are not limited to, those having a faujasite, sodalite, beta (BEA), Linde (LTA), mordenite, ferrierite, ZSM-5, A-type, X-type, Y-type, or L-type framework. In a specific embodiment, the zeolite has a specific $SiO_2/Al_2O_3$ ratio and/or cation type to lend the zeolite a desired structural property.

"Microporous" refers to porous materials in which the pores have a cross sectional dimension, such as a diameter, of less than 2 nm. "Mesoporous" refers to porous materials in which the pores have a cross sectional dimension, such as a diameter, between 2 nm and 50 nm. See, also *Pure Appl. Chem.*, Vol. 73, no. 2, pp. 381-394, 2001, and *Reviews in Mineralogy and Geochemistry*, Vol. 57, pp. 1-16, 2005, which are hereby incorporated by reference.

"Specific surface area" refers to a per mass measure of the total surface area of a material. In embodiments, the specific surface area of a material is measured by measuring a quantity of a known gas, such as nitrogen, that adsorbs onto the surface at a specific temperature and computing the required planar surface area necessary to adsorb the same quantity of gas at the same temperature. In an embodiment, a specific surface area is calculated using the Brenauer-Emmett-Teller (BET) model. In an embodiment, a surface area is calculated using the Langmuir model.

"Fractional coverage" refers to a measure of the percentage of active adsorption sites of an adsorbent which are occupied by an adsorbate. In an embodiment, fractional coverage refers to the fraction of active adsorption sites of the exposed surface of an adsorbent occupied by an adsorbate, optionally calculated by fitting uptake data with a multi-Langmuir model and determining the maximum uptake amount.

"Exposed surface" refers to the boundary of a material that is positioned in contact with a gas. In embodiments, the exposed surface of a porous material comprises surfaces which are exposed to a gas and otherwise are available for adsorption. In embodiments, the exposed surface of a porous material includes the exterior surface of the material exposed to a gas as well as the surface of any pores which are also exposed to the gas, for example pores possessing a sufficient cross sectional dimension to permit entry of the gas into the pore volume.

"Porous template" refers to a porous material used in the fabrication of another porous material. In an embodiment, a porous template is used as a pattern for another porous material, for example by filling pores of the porous template with a precursor material and then reacting or otherwise converting the precursor material to another species or structure.

"Non porous" refers to a substantial lack of a plurality of pores. In an embodiment, a non porous material comprises a material lacking an ordered or disordered pore structure.

The present invention provides methods for storing gases on porous adsorbents, methods for optimizing the storage of gases on porous adsorbents, methods of making porous adsorbents, and gas storage compositions, such as combinations including porous adsorbents and gas adsorbed on a surface of the porous adsorbent.

FIG. 1A illustrates a schematic depiction of a porous adsorbent 100 embodiment. Porous adsorbent 100 comprises an ordered pore structure comprising a plurality of pores 101. Each pore 101 has a cross sectional dimension, exemplified in the embodiment shown in FIG. 1A as a pore diameter 102. Additionally, adjacent pores are separated by an inter-pore spacing 103, exemplified in the embodiment shown in FIG. 1A as a wall-to-wall pore spacing.

Figure 1B:
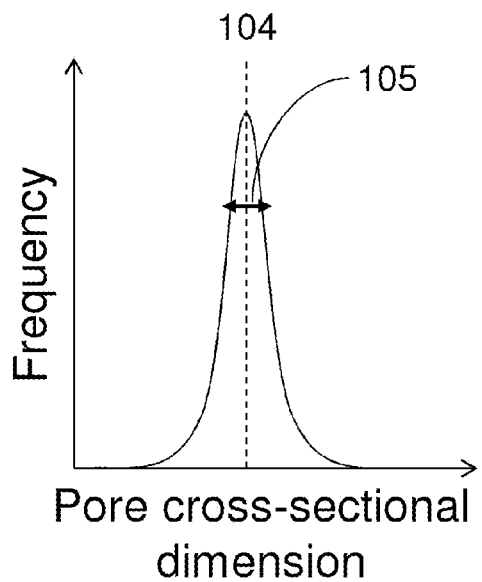
FIG. 1B illustrates an exemplary frequency distribution of pore cross sectional dimensions.
Figure 1C:
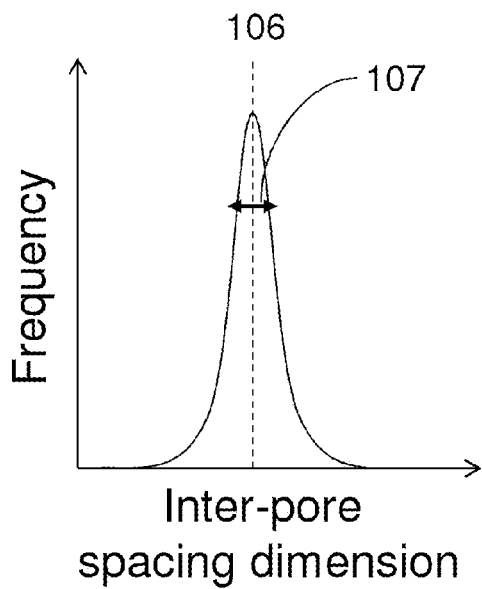
FIG. 1C illustrates an exemplary frequency distribution of inter-pore spacing dimensions.

FIG. 1B illustrates an exemplary pore size distribution, showing pore size mean 104 and variance 105. Similarly, FIG. 1C illustrates an exemplary inter-pore spacing dimension distribution, showing inter pore spacing mean 106 and variance 107.

Figure 2:
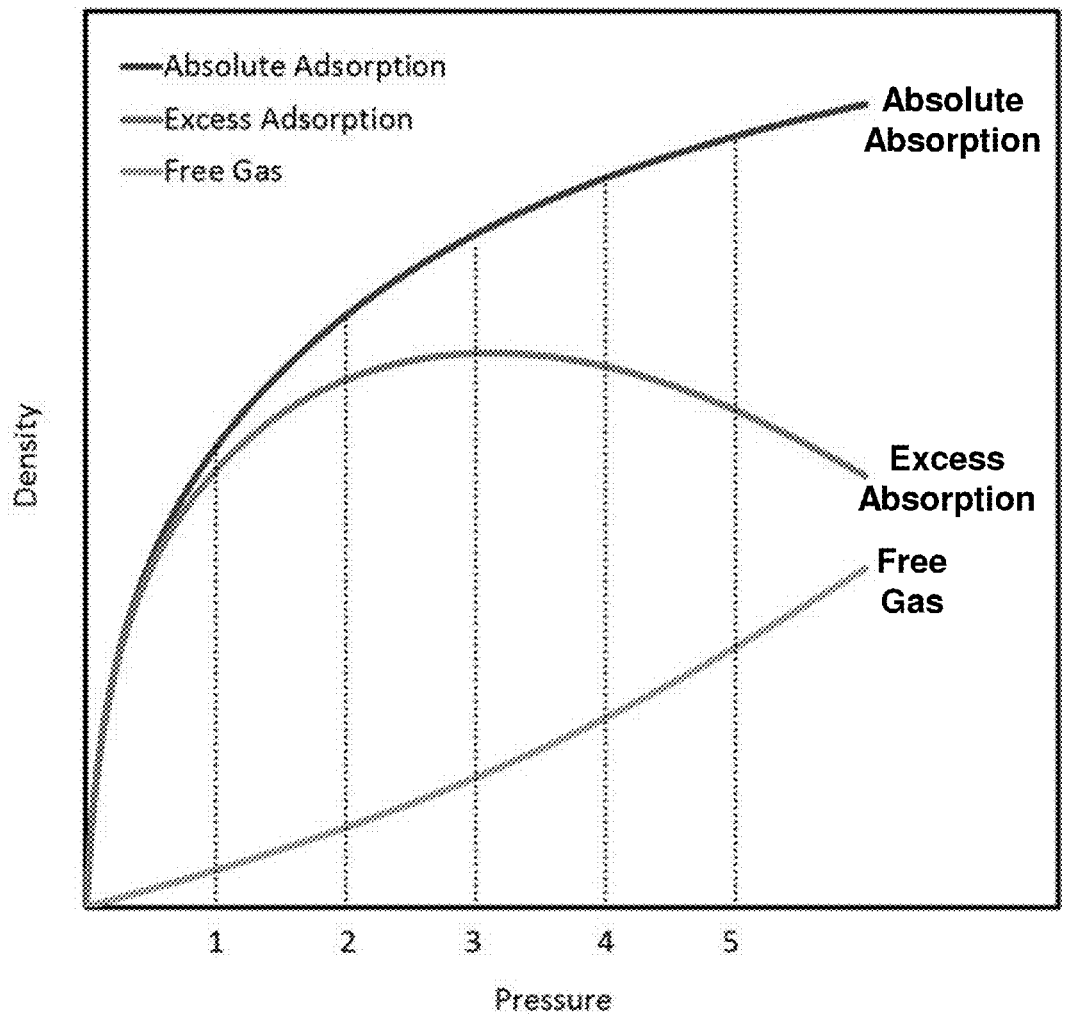
FIG. 2 provides a plot illustrating the excess adsorption and free gas contributions to absolute adsorption as a function of pressure.

FIG. 2 provides a hypothetical plot of the excess adsorption and free gas contributions to absolute adsorption as a function of pressure, shown to illustrate the important distinction between the excess (measured) and absolute (actual) adsorbed quantities at high pressure.

Figures 3A, 3B:
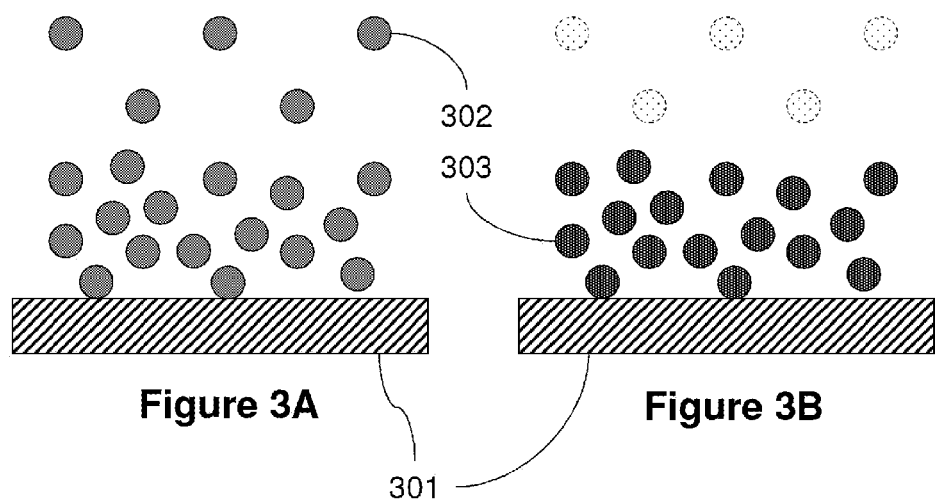
FIGS. 3A-3C provide schematic illustrations of a surface exposed to a gas, illustrating the various defined quantities of adsorbate molecules/atoms in the system.
Figure 3C:
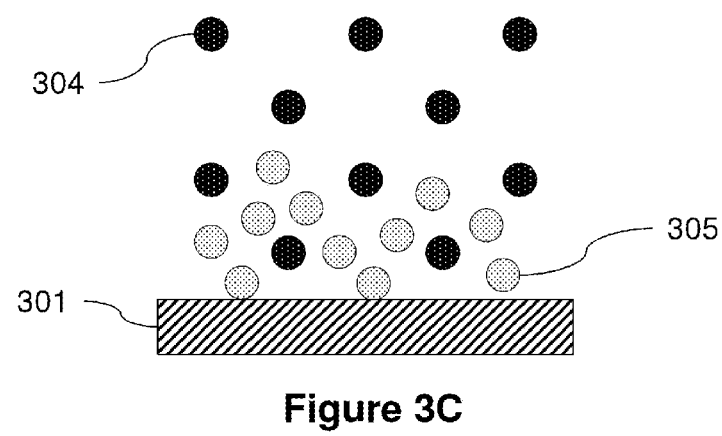

FIGS. 3A-3C provide a schematic depiction of an adsorbent-adsorbate system embodiment. In FIG. 3A, an adsorbent 301 is exposed to a gas such that an adsorbed layer forms on the surface of the adsorbent and shows the total amount of adsorbate 302 stored in the container, including both gaseous and adsorbed molecules/atoms which are in equilibrium. FIG. 3B highlights the portion of the gas adsorbed to the surface of the adsorbent (303, dark grey). In embodiments, the highlighted (dark grey) portion of the gas shown in FIG. 3B is referred to as the absolute uptake amount. The remaining gas is not adsorbed, and exists as a normal compressed gas. FIG. 3C differentiates between the gas that would be present in the volume surrounding the adsorbent if the adsorbent were not present (304, black). In embodiments, the remaining adsorbate molecules/atoms in the adsorption layer (305, light grey) are referred to as the excess adsorbed amount or excess uptake, the quantity measured in adsorption experiments.

The invention may be further understood by the following non-limiting examples.

Example 1

Nanostructured Carbon Materials for Adsorption of Methane and Other Gases

This Example describes new materials and design principles for improving the deliverable storage capacity of an adsorbent based compressed gas storage system by controlling the pore structure of the adsorbent material to achieve desirable thermodynamic properties. Results for methane storage are presented.

High-pressure adsorption is vital to numerous engineering processes and industrial applications and is a promising alternative for future energy storage solutions, such as for compact storage of methane and hydrogen fuels. Adsorption based technologies rely on the densification of the adsorbed species near the surface of the adsorbent material, a result of weak physical interactions between the adsorptive species and the adsorbing surface. Since adsorption is fundamentally a surface effect (molecules of gas do not enter the material below its surface), the uptake capacity of the sorbent material is proportional to its accessible surface area, but also dependent on the strength of the adsorbent-adsorbate binding interaction. While the accessible surface area dictates the total number of binding sites (and hence the maximum uptake capacity), the binding energy of each site influences the uptake at a given temperature and pressure in accordance with statistical thermodynamic distributions. If the distribution of binding energies is wide, high energy sites will be occupied first, followed by low energy sites—the details of this determine how much adsorbate remains in the storage container at low pressure (when it is effectively empty). The optimal sorbent material has a large number of binding sites and a narrow distribution of binding energies so that high energy sites continue to be filled at high site occupancy. The quantity of interest in estimating the binding energy of the adsorbent-adsorbate surface interaction is the differential enthalpy of adsorption, which can be measured directly (by calorimetry) or indirectly (by equilibrium adsorption measurements).

Carbon materials with a large specific surface area have been used in numerous applications such as gas storage, gas separation, and adsorption refrigeration. They benefit from light weight, abundance, complete reversibility, high cyclability, and fast kinetics of gas delivery. For the storage of gaseous fuels in mobile vehicles, a serious obstacle to realizing the mass introduction of alternative fuel powered vehicles, achieving a high volumetric density of deliverable fuel is critical. Material design is usually directed at increasing the relative number of binding sites and/or increasing the binding energy of adsorption, but little attention has been paid to the distribution of binding energies within the material. By optimizing this distribution, the thermodynamics of adsorption can be carefully tuned to maximize the performance of the adsorbent material.

Methane Storage.

Compact storage of methane by adsorption is a promising application for porous carbonaceous materials. The adsorption enthalpy of methane on carbon is typically 13-19 kJ mol$^{-1}$ at near ambient conditions, making room temperature applications very promising. Several methane adsorbents have been proposed, for example:

Baker, F. S.; Wando, S. C.; Low Pressure Methane Storage with Highly Microporous Carbons. U.S. Pat. No. 5,626,637, (1997).

Pfeifer, P. et al.; High Surface Area Carbon and Process for its Production. US Patent Application 20080207442, (2012).

Gas Separation and Purification.

Microporous adsorbents are widely used for gas separation and purification. Different adsorbent-adsorbate interactions for different gases on the same material lead to the selective adsorption of one gas more than another in a multi-component stream. For example:

Maurer, R. T.; Methane purification by pressure swing adsorption. U.S. Pat. No. 5,171,333, (1992).

Tonkovich, A. L. et al.; Process for separating nitrogen from methane using microchannel process technology. U.S. Pat. No. 7,250,074, B2 (2007).

Reyes, S. C. et al.; Separation of methane from higher carbon number hydrocarbons utilizing zeolitic imidazolate framework materials. U.S. Pat. No. 8,192,709, B2 (2012).

Adsorption Refrigeration.

Adsorption is an exothermic process, and cycling between the adsorbed and desorbed state entails an exchange of heat which can be used to drive/regenerate a refrigeration cycle. *When gas adsorbs to the surface of an adsorbent material, heat is released which can be used to evaporate a refrigerant and achieve cooling (analogous to the decompression phase in a compression refrigerator). An external source of heat must then be used to desorb the adsorbate, and the refrigerant condenses releasing heat into the environment. Adsorption refrigerators harness this cooling effect by undergoing discontinuous cycles, usually involving two parallel adsorption beds for "semi-continuous" cooling.

The cooling power is proportional to the heat of adsorption, a thermodynamic property of the sorbent material. There is no mechanical energy involved as the entire process is driven by heat energy making this process attractive for certain niche applications. Methane sorption on a carbon material is an attractive system due to its low toxicity and cost. The optimized tuning of thermodynamic properties is essential to maximizing performance of an adsorptive refrigerator.

Carruthers, J. D.; Component for solar adsorption refrigeration system and method of making such component. US Patent Application 20110048063 (2011).

Maier-Laxhuber et al.; Adiabatic heating and cooling process and portable devices in accordance with the adsorption principle. U.S. Pat. No. 4,752,310, (1988).

Yonezawa et al.; Adsorption refrigeration system. U.S. Pat. No. 4,881,376, (1989).

This Example discloses an improved adsorption-based gas storage system with tuned thermodynamic properties. The thermodynamic quantity of interest is the differential enthalpy of adsorption, a measure of the adsorption energy. It is usually derived from experimental adsorption data by the isosteric method, thus referred to as the isosteric enthalpy of adsorption, and is equal to the heat released upon adsorption at a constant state of uptake. The isosteric enthalpy of adsorption is dependent on the surface chemistry and the microstructure of the adsorbent. The nature of the surface chemistry gives a baseline for the adsorption energies available for interaction with the adsorbate; ideally, the surface is homogeneous and characteristic binding energies are relatively high.

New nanostructured materials allow for tuning the thermodynamic properties of the adsorbent. If the surface is a wall of a large, smooth pore or is external to the material, this is defined as having no effect from microstructure. However, if two opposing surfaces are close together, or form a concavity, the binding interaction can be altered. The optimal spacing between walls is on the order of a few molecular diameters of the adsorptive gas: this corresponds to ~1 nm for methane. To ensure the homogeneity of binding energies between sites, the pore-width must have a narrow distribution centered at the optimal distance for adsorption. If high homogeneity can be achieved in the microstructure and surface chemistry, an isosteric enthalpy that is constant as site occupancy increases can be achieved.

Further, and what is new in this disclosure, the nature of the adsorptive gas must be considered to determine the optimal conditions for enhanced binding interactions between the adsorbent and adsorbate. For methane, extremely strong intermolecular interactions occur near ambient temperature (e.g. −40° C.), making these conditions favorable for adsorption on a homogeneous surface. In fact, if the surface chemistry and microstructure of the adsorbent are well controlled, the attractive interactions between adsorbed methane molecules can bestow an increasing binding interaction as site occupancy increases. This is a highly desirable feature of a sorbent material since it is more important to have strong binding interactions in the regime of intended use (typically intermediate to high pressures) than at pressures below the "empty" system state (typically <3 bar for delivery to a fuel cell, for example).

Material and method of design of simple, cost-effective carbonaceous materials are described: they are predominantly microporous, contain a narrow distribution of pore-widths around a specific mean width, and are characterized by a highly homogeneous surface. The pore-width can be tuned for methane adsorption, as explained below, or adapted for other adsorptive gases to suit the given application. Most importantly, the material shows a constant or increasing isosteric enthalpy of adsorption across a wide range of surface coverage, lending the following advantageous properties depending on application:

1) an exceptional deliverable quantity of gas over a wide range of pressure (e.g. in the case of adsorbent-based energy storage), 2) a high selectivity of gas across a wider range of partial pressure (e.g. in the case of gas separation/purification), and/or 3) a significantly increased quantity of heat available during pressure cycling (e.g. for exchange with an evaporator/condenser during adsorptive refrigeration).

The effective design and synthesis approach is based on template-carbonization. The process involves impregnation of a silica-based template with a hydrocarbon precursor, polymerization and subsequently carbonization of the hydrocarbon at raised temperatures, and removal of the template via acid dissolution. A suitable template is chosen which has a periodic array of pores so that the resulting pure carbon analog will contain pores of the spacing desired. For methane adsorption, maximum binding energy is predicted for pores of 1.14 nm in width, corresponding to the typical channel-to-channel distances in NaY type zeolites (faujasite).

An example material, referred to in this Example as ZTC-3, contains a narrow pore-size distribution centered at ~1.2 nm and predominantly $sp^2$ hybridized carbon (ensuring maximum homogeneity of the surface). The isosteric enthalpy of adsorption as a function of methane uptake is constant or increasing at temperatures between 238-518 K, a range of particular interest for engineering applications (see FIG. 4). Deliverable methane capacity in ZTC-3 is increased by 23% over MSC-30 (a commercially available carbon of comparable surface area) at 238 K (see FIG. 5). Deliverable methane was even 6% higher than MSC-30 at room temperature where total adsorption was actually lower, a proof of concept of this design.

Figure 4:
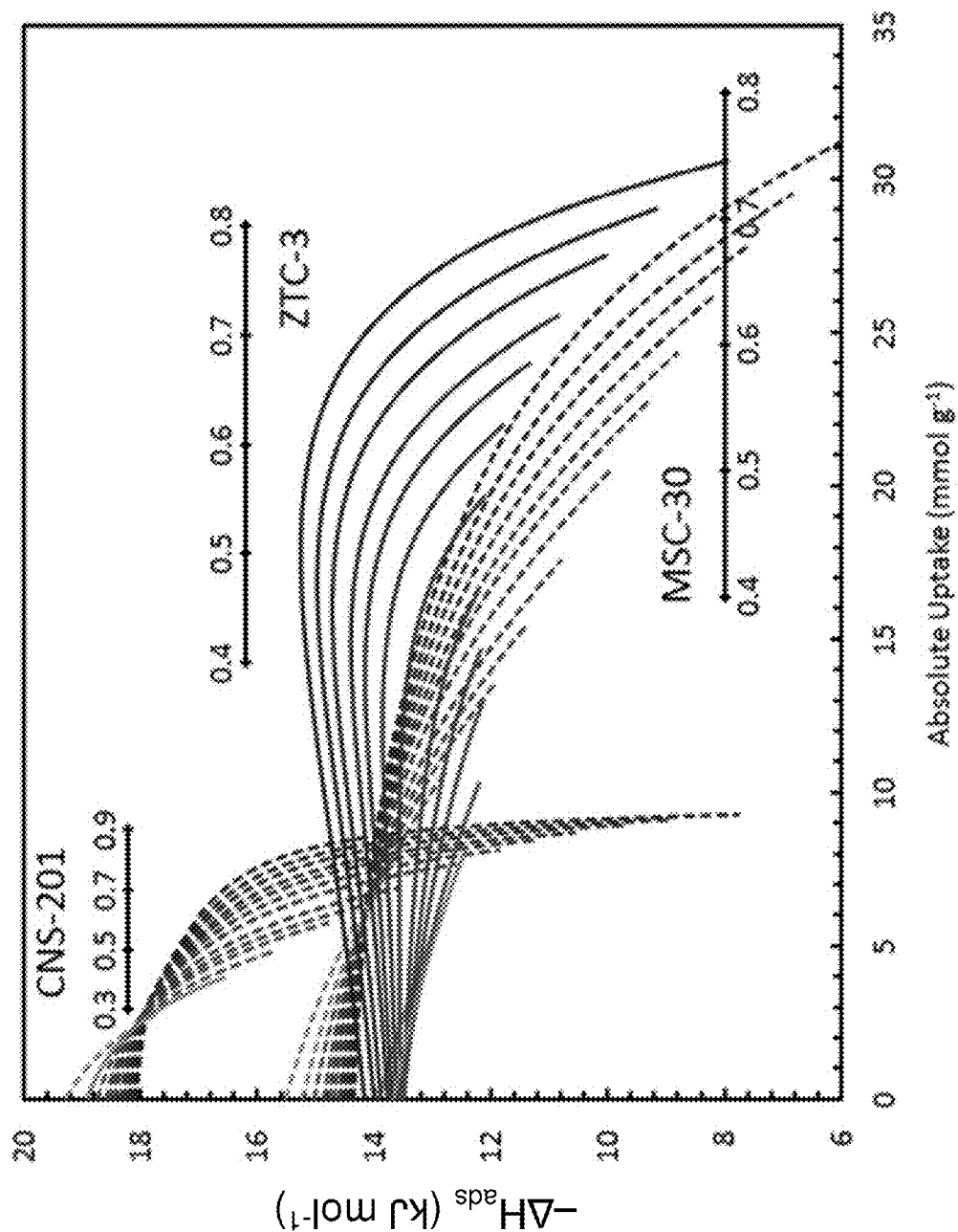
FIG. 4 provides data showing the enthalpy of adsorption of methane as a function of uptake on three materials: CNS-201 (a commercial activated carbon), MSC-30 (a high surface area commercial activated carbon), and ZTC-3 (an example zeolite-templated carbon material).

FIG. 4 provides data showing the enthalpy of adsorption (an experimentally accessible interpretation of the binding energy) of methane on three materials: CNS-201 (a standard commercial activated carbon), MSC-30 (a high surface area commercial activated carbon), and ZTC-3 (an example material). The binding energy typically decreases as a function of uptake in the material, as seen for the commercially available activated carbons. This results in a significantly decreased adsorptive performance in the regime of high uptake, which is precisely the regime of interest for applications. ZTC-3 shows an increase in binding energy as a function of uptake, a result of the tuned nanostructure which allows attractive methane-methane interactions to dominate the thermodynamics of adsorption in the regime of high uptake.

Figure 5:
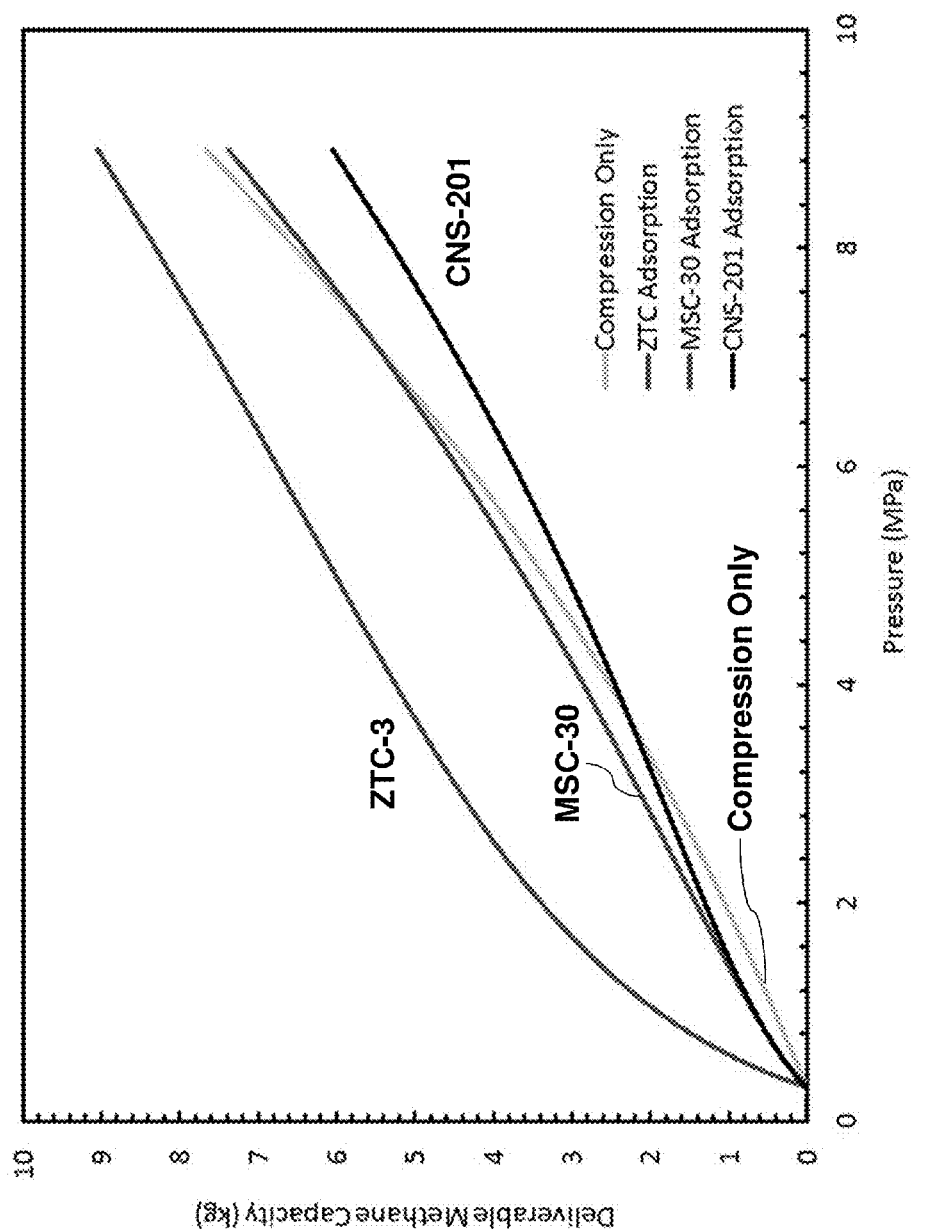
FIG. 5 provides data illustrating the calculated deliverable quantity of methane as a function of pressure for an empty storage tank and for a tank filled with various adsorbent materials.

Description of FIG. 5. The deliverable quantity of methane (in kg) is given for a typical high-pressure cylinder for on-board storage of methane in a light passenger vehicle at −40° C. The tank has an inner volume of 70 L. In the case of "compression only" (yellow line), the tank is empty until it is filled with methane. If the methane is delivered to a fuel cell, the minimum pressure required is 0.3 MPa (~3 atm). Thus, the deliverable quantity at this pressure is 0. If the inner volume of the tank is packed with an adsorbent material prior to filling with methane (ZTC-3, MSC-30, or CNS-201), the deliverable amount is increased due to densification of the gas near the sorbent surface. It may or may not benefit the tank over pure compression since the material takes up volume in the tank. However, for ZTC-3, deliverable methane is significantly higher at all pressures (e.g. 5.25 kg is delivered at 4 MPa with ZTC-3 vs. 2.5 kg in pure compression). Alternatively, the same quantity of methane could be delivered in a sorbent filled tank at a much lower pressure (e.g. 4 kg is delivered at 2.6 MPa in ZTC-3 vs. 5.7 MPa in pure compression).

Example 2

Anomalous Isosteric Enthalpy of Adsorption of Methane on Zeolite-Templated Carbon This example describes a thermodynamic study of the enthalpy of adsorption of methane on high-surface area carbonaceous materials that was carried out from 238-526 K. The absolute quantity of adsorbed methane as a function of equilibrium pressure was determined by fitting isotherms to a generalized Langmuir-type equation. The adsorption of methane on zeolite-templated carbon (ZTC), an extremely high surface-area material with a periodic arrangement of narrow micropores, shows an increase in isosteric enthalpy with methane occupancy; that is, binding energies are greater as adsorption quantity increases. The heat of adsorption rises from 14 to 15 kJ mol$^{-1}$ at near ambient temperature, then falls to lower values at very high loading (above a relative site occupancy of 0.7), indicating that methane-methane interactions within the adsorption layer become significant. The effect seems to be enhanced by a narrow pore-size distribution centered at 1.2 nm, approximately the width of two monolayers of methane, and reversible methane delivery increases by up to 20% over MSC-30 at temperatures and pressures near ambient.

High-pressure adsorption is vital to numerous engineering processes and industrial applications today, and is perhaps relevant to future systems for compact storage of methane and hydrogen fuels. Carbonaceous sorbent materials are particularly attractive because they are lightweight, abundantly available, simple to produce, and can effectively increase the volumetric density of stored gases. For effective energy storage by physical adsorption, a high total capacity (corresponding to a large number of binding sites) is necessary for high potential delivery. Additionally, the characteristic binding energies of the sorbent-adsorbate interactions are crucial to the practical deliverable capacity because the storage tank must be cycled between two finite pressures, and the amount stored in the system at the lower bound (e.g. 0.3 MPa) should be low. The optimal material for physisorptive energy storage has been assumed to have a high binding energy that is constant with increased loading. For hydrogen, the average enthalpy of adsorption across a wide variety of carbon materials (activated carbon, nanofibers, aerogels, templated-carbons, etc.) is 4-6 kJ (mol $H_2)^{-1}$, which is not significantly higher than the average thermal energy at 298 K and limits their effective use to cryogenic temperatures. Physical adsorption of methane is much stronger, typically 12-20 kJ $mol^{-1}$, and near-ambient temperature applications for methane storage are more promising.

In microporous carbonaceous materials, the pore structure and surface chemistry are the characteristics that offer the potential to adjust the thermodynamic properties of adsorption. Boron- and nitrogen-doped materials have shown promise in exhibiting higher enthalpies of adsorption of hydrogen. However, as in pure carbon-based materials, the enthalpy declines with loading. A more effective approach for tuning the thermodynamics of adsorption is by controlling the pore-size distribution and mean pore width to achieve optimal binding interactions. Theoretical models of adsorption in graphitic slit pores show that pore-widths corresponding to three molecular diameters of the adsorptive gas are ideal for maximizing adsorbate-adsorbate interactions and increasing the total energy of adsorption. However, adsorption measurements on engineered graphene-scaffolds and other microporous materials have never shown an appreciably increasing binding energy in the high surface coverage regime.

Template carbonization is an effective technique for producing carbonaceous materials with exceptionally large specific surface area and controlled porosity. Zeolite-templated carbons (ZTCs) are microporous, amorphous carbon materials with extremely high surface area and a periodic array of pores complementary to the structure of the zeolite used in the template-carbonization synthesis. The hydrogen storage capacities of ZTCs were reported to be exceptionally high at pressures between 10-34 MPa, but recent results showed that this capacity is simply proportional to specific surface area, typical of other materials.

The nature of the microstructure of carbonaceous materials has not been reported to have an effect on their adsorptive capacities for methane, but pore widths in these materials do approach the optimal value suggested to be 1.14 nm. Recent calculations of methane adsorption on metal-organic framework CPO-27-Mg, a crystalline material with well-characterized adsorption sites within small (~1.1 nm) cages, show that strong adsorbate-adsorbate interactions play an important role in the enthalpy, resulting in a 15% increase in excess capacity at near 298 K. The average binding energy, though, decreases with loading due to the sequential filling of binding sites corresponding to distinct, decreasing energies. Carbonaceous materials with controlled pore-widths such as templated carbons offer the potential for a more homogeneous distribution of sorption sites, but to date a material with constant isosteric enthalpy has been elusive.

This example describes an investigation of high-pressure methane sorption in a zeolite-templated carbon referred to as ZTC-3, a model zeolite-templated carbon material for methane storage, with a narrow pore-size distribution centered at 1.2 nm. ZTC-3 was synthesized by the impregnation of zeolite NaY with poly-furfuryl alcohol, undergoing a propylene CVD step at 700° C., and carbonization was performed at 900° C. The template was removed by dissolution in HF. Details of the synthesis, and the important steps for attaining high template fidelity, are described in Stadie, N. P.; Vajo, J. J.; Cumberland, R. W.; Wilson, A. A.; Ahn, C. C.; Fultz, B. *Langmuir* 2012, 28, 10057-63, which is hereby incorporated by reference. For comparison, two other commercial activated carbons were also investigated: CNS-201, a modest surface area carbon with extremely narrow micropores, and MSC-30, a superactivated carbon with extremely high surface area that is often measured as a standard. These materials were degassed at 250° C. under vacuum to <0.1 mPa before use.

Nitrogen adsorption/desorption isotherms at 77 K were collected to calculate surface areas, micropore volumes, and pore-size distributions of the materials. The Brunauer-Emmett-Teller (BET) surface areas of CNS-201, MSC-30, and ZTC-3 are 1095, 3244, and 3591 $m^2$ $g^{-1}$, respectively. The Dubinin-Radushkevich (DR) method was used to calculated their microporous volumes: 0.45, 1.54, and 1.66 mL $g^{-1}$. The pore-size distribution in CNS-201, obtained by the non-localized density functional theory (NLDFT) method, contains 3 peaks, at 0.54 nm, 0.80 nm, and 1.18 nm, with 50%, 20%, and 15% of the pore volume in each, respectively. MSC-30 contains a broad distribution of pore-widths between 0.6-3.5 nm and 40% of the pore volume is contained in pores >2.1 nm in width. The distribution of pores in ZTC-3 is characterized by a single sharp peak centered at 1.2 nm, with >90% of the pore volume having a pore width between 0.85-2.0 nm. This regularity of pore-size in ZTC-3 was confirmed by x-ray diffraction (XRD) with Cu Kα radiation, which shows a sharp peak centered at 2θ=6°, and transmission electron microscopy (TEM) which shows a periodic spacing of diffraction contrast corresponding to pores of width 1 nm (see FIG. 6).

Skeletal densities of the samples were measured by helium pycnometry; the activated carbons have 2.1 g $mL^{-1}$, consistent with a wide variety of carbonaceous materials, while ZTC-3 has a lower skeletal density (1.8 g $mL^{-1}$, consistent with other ZTCs) presumably due to increased hydrogen terminations (see below).

Methane adsorption isotherms at all temperatures were measured with a volumetric Sieverts apparatus, commissioned and verified for accurate measurements up to 10 MPa. Two adsorption runs using research-grade methane (99.999%) were performed at each temperature and the data were combined for thermodynamic analysis. Multiple adsorption/desorption cycles were also performed at various temperatures to assure full reversibility of methane physisorption in the complete temperature and pressure regime of study and to test the precision of the experiments. Error between cycles is <1% of the measured value (see below).

Figure 7A:
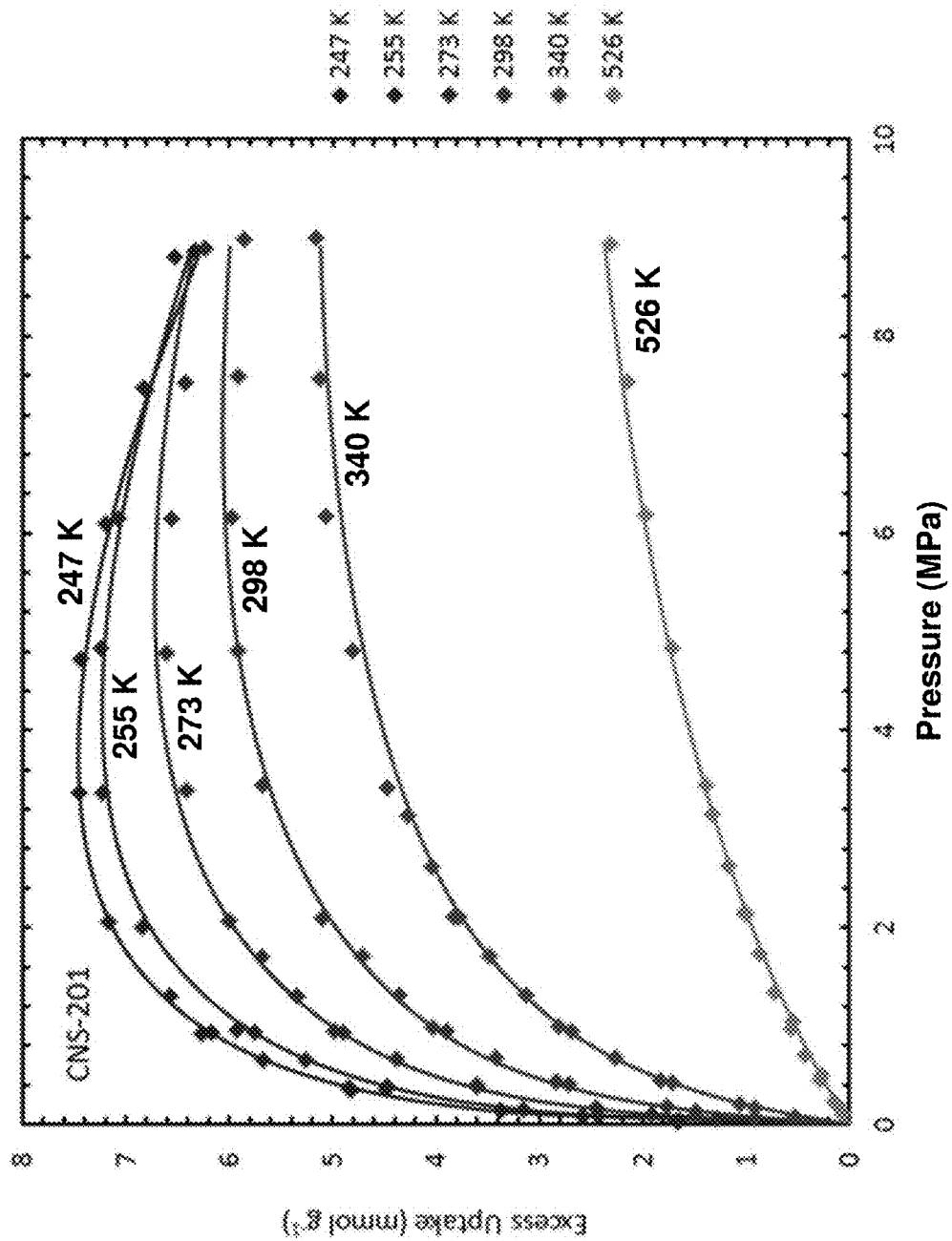
FIGS. 7A-7C provide data showing equilibrium excess adsorption isotherms of methane on various adsorbents and at various temperatures.
Figure 7B:
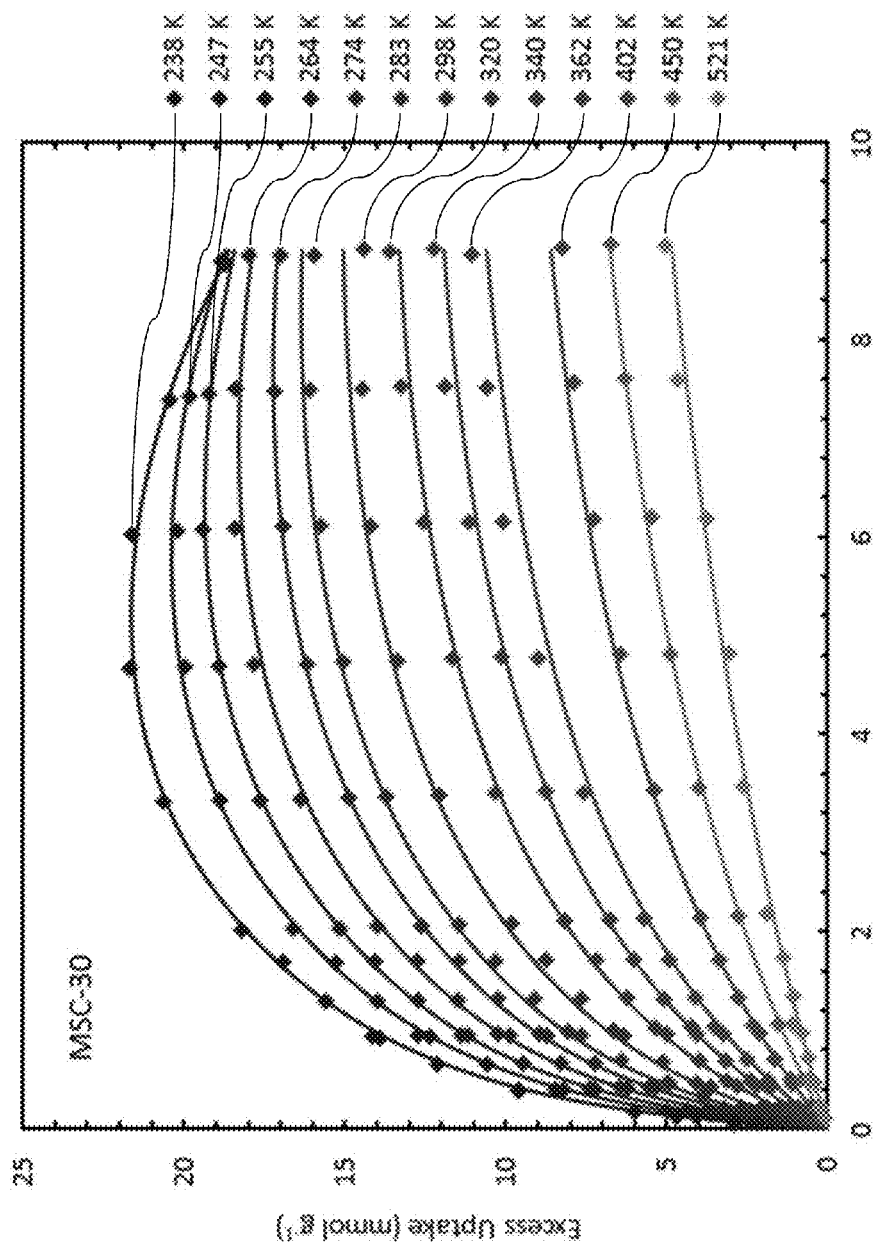
Figure 7C:
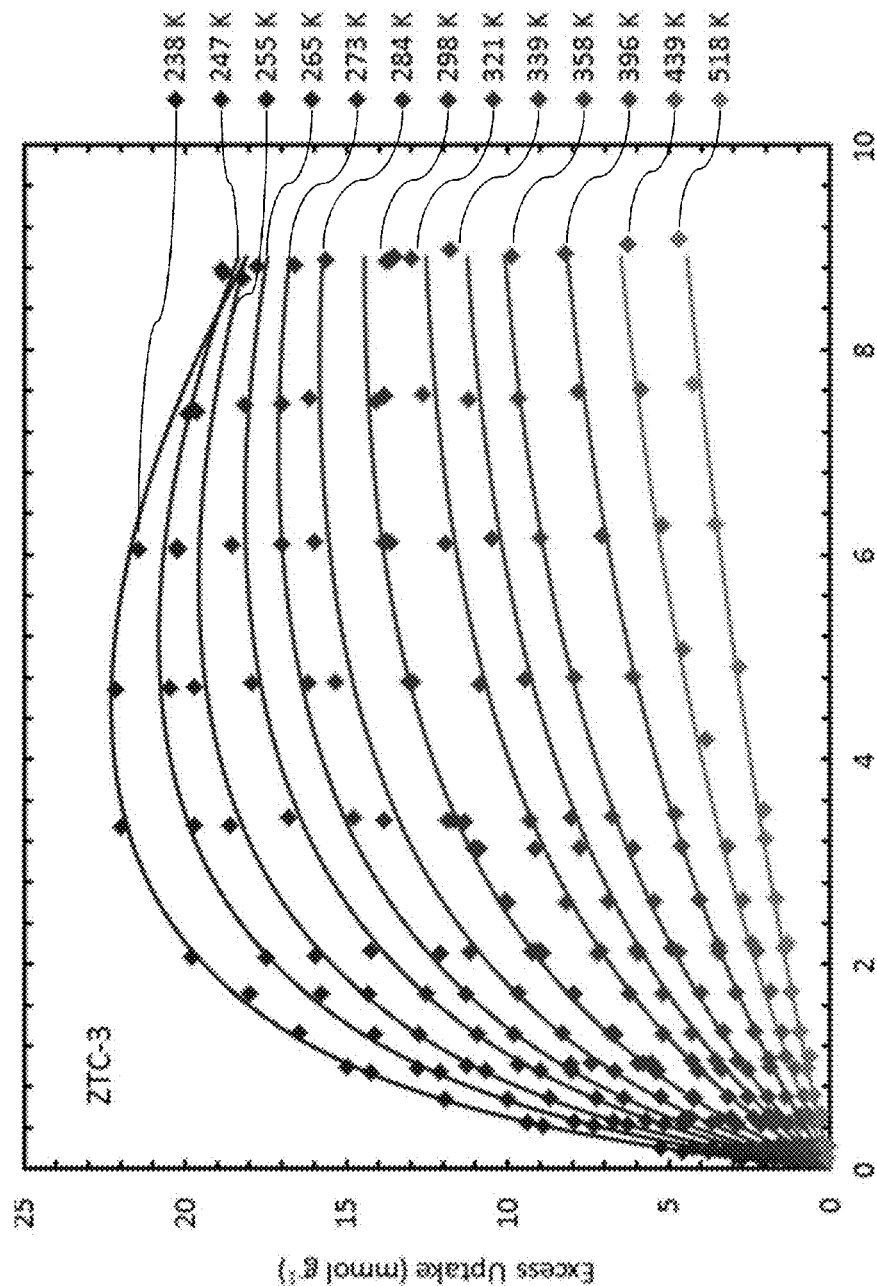

Equilibrium adsorption isotherms of methane are shown in FIGS. 7A-7C for CNS-201 (FIG. 7A), MSC-30 (FIG. 7B) and ZTC-3 (FIG. 7C). The experimental quantity of adsorption is the Gibbs surface excess, the amount of adsorbate in excess of the gas density within the entire void volume of the container; hence, the adsorption shows a surface excess maximum at high pressures. This maximum is a readily accessible figure of merit for the gravimetric performance of a material at a fixed temperature. The excess maximum is similar for ZTC-3 and MSC-30 at room temperature, but slightly higher for MSC-30: 14.5 mmol $g^{-1}$ at 8 MPa. While excess adsorption increases faster for MSC-30 at pressures between 0-0.8 MPa, uptake in ZTC-3 increases fastest between 0.8-5.7 MPa. Gravimetric uptake in CNS-201 is substantially less at all temperatures due to its low specific surface area. The highest measured excess uptake of this Example is for ZTC-3 at 238 K: 22.1 mmol $g^{-1}$ (26.2 wt %) at 4.7 MPa, despite a gentler initial increase at low pressure. Interestingly, the excess uptake in ZTC-3 is also greater than MSC-30 at high temperatures although neither reaches a maximum between 0-9 MPa. At all temperatures, methane uptake in ZTC-3 is characterized by a gradual initial rise and delayed increase at pressures between 0.2-2 MPa, leading to higher eventual methane capacity than MSC-30, a material of comparable specific surface area.

For thermodynamic calculations, interpolation of the data of FIGS. 7A-7C is necessary. It is common to proceed with the measured Gibbs excess quantities as an approximation of the actual (absolute) adsorbed amount, an acceptable practice for studies of adsorption well below the critical point (low pressure and temperature) where excess and absolute adsorption quantities are approximately equal. At temperatures and pressures near the critical point and above, however, thermodynamic calculations from excess adsorption data lead to well-documented errors, and quantities calculated by this method should be referred to as "isoexcess" quantities. A detailed investigation of the effects of different analysis methods of the data acquired in this Example is given below and in Stadie, N. P. PhD. thesis, California Institute of Technology, 2012, which is hereby incorporated by reference.

The Gibbs definition of the surface excess quantity, $n_e$, depends on the bulk gas density, $\rho$, as:

$$n_e = n_a - V_{ads}\rho(P,T)$$

To calculate the absolute adsorbed quantity, $n_a$, the remaining unknown is the volume of the adsorption layer, $V_{ads}$, and numerous methods have been suggested to estimate it. A general approach is to let the adsorption volume be an independent parameter of the fitting equation. The following fitting equation was adopted for Gibbs excess adsorption, $n_e$, as a function of pressure, P, and temperature, T, where $V_{ads}$ scales with coverage up to a maximum, $V_{max}$:

$$n_e(P, T) = (n_{max} - V_{max}\rho(P, T))\left(\sum_i \alpha_i \left(\frac{K_i P}{1 + K_i P}\right)\right)$$

$$K_i = \frac{A_i}{\sqrt{T}} e^{\frac{E_i}{RT}}$$

$$\sum_i \alpha_i = 1$$

A generalized-Langmuir equation (as above) has been shown to require a relatively small number of fitting parameters to achieve a satisfactory fit to the experimental data. The minimum number of independent parameters is desired, and it was found that i=2 yields satisfying results across a large number of materials in supercritical adsorption studies of both methane and hydrogen adsorption on carbon.

The maximum in excess adsorption measured in this example at 298 K scales linearly with the specific surface area of the materials studied, a relationship analogous to "Chahine's rule" for the surface excess maximum of hydrogen at 77 K, consistent with the reported linear trend for methane uptake at 3.5 MPa and 298 K. The fit parameters also generally correlate with the properties of the materials studied. The scaling parameter $n_{max}$ is proportional to the number of binding sites and is well approximated by the BET specific surface area. The maximum volume of the adsorbed layer, $V_{max}$, is also proportional to surface area for the activated carbons, but is limited (in the case of ZTC-3) by the pore-width, a direct result of complete pore-filling since this material has both molecular-sized pores and extremely high microporosity. The maximum volume of the adsorbed layer in ZTC-3, if taken to be proportional to surface area, corresponds to half of the mean pore diameter of the material: a thickness of 0.6 nm.

The thermodynamic quantity of interest for adsorbent materials is the differential enthalpy of adsorption, $\Delta H_{ads}$, often obtained by the isosteric method and reported as the positive value $q_{st}$, the isosteric heat of adsorption (in this work, "enthalpy" refers to the positive value):

$$q_{st} = -\Delta H_{ads}(n_a) = -T\left(\frac{\partial P}{\partial T}\right)_{n_a}(\Delta v_{ads})$$

It is necessary to use this general form of the Clausius-Clapeyron relationship for methane adsorption at high pressure because of the significant non-ideality of methane gas-state properties. Its derivation and explanation with respect to the usual ideal-gas form of the equation is given below. The only simplifying assumption made in this work is that the net change in molar volume of the system upon adsorption, $\Delta v_{ads}$, is approximately equal to that of the difference between the bulk gas and liquid methane. Variations on this approximation had little effect on the result. A modified Webb-Benedict-Rubin equation of state was used to calculate the bulk gas density, giving significantly different results than by assuming ideal gas density. The isosteric enthalpy of adsorption of methane on CNS-201, MSC-30, and ZTC-3 at the temperatures measured is shown in FIG. 4.

The Henry's law value of adsorption enthalpy, $\Delta H_0$, is calculated by extrapolation of the enthalpy of adsorption to zero pressure. The Henry's law values for CNS-201, MSC-30, and ZTC-3 are 18.1-19.3, 14.4-15.5, and 13.5-14.2 kJ mol$^{-1}$, respectively. The temperature dependence of $\Delta H_0$ for CNS-201 and MSC-30 is the same: +4.1 J mol$^{-1}$ K$^{-1}$. The Henry's law values from 238-518 K for ZTC-3 depend non-linearly on temperature, indicating significantly different thermodynamics of methane adsorption in this range. At low temperatures the trend is negative (−16 J mol$^{-1}$ K$^{-1}$ at 247 K), and then increases toward that of the activated carbons (reaching +3.0 J mol$^{-1}$ K$^{-1}$ at 450 K).

The characteristics of methane adsorption as a function of fractional site occupancy, $\theta$, in the activated carbons (CNS-201 and MSC-30) are typical of other carbon materials, with $q_{st}$ decreasing with $\theta$. In the range $0<\theta<0.6$, the more graphitic CNS-201 shows a more gradual decrease of $q_{st}$ than MSC-30, indicative of more heterogeneous site energies in the latter. Surprisingly, the isosteric enthalpy of adsorption in ZTC-3 increases to a maximum at $\theta$=0.5-0.6 at temperatures from 238-273 K. The enthalpy then declines rapidly at high coverage. Beyond $\theta$=0.7, however, the rapid decline is similar in all three materials due to very high density in the high pressure gas.

The increasing isosteric enthalpy of adsorption in ZTC-3 is anomalous compared to previous experimental reports of methane adsorption on carbon. The increase of 1.1 kJ mol$^{-1}$ at 238 K is an increase of 8%, a large effect. It is likely that this originates with intermolecular interactions between adsorbed methane molecules, as suggested by theoretical work. For gaseous methane, the chemical potential does not increase so rapidly with pressure as for an ideal gas, a characteristic of attractive intermolecular interactions. At intermediate e, the adsorbed methane molecules may find surface configurations that optimize intermolecular interactions. The average distance between adsorbed methane molecules (approximated as the square root of the BET surface area per molecule) at the surface excess maximum was the same in all three materials in this Example (e.g. 0.5 nm at 238 K), so the more attractive interactions in ZTC-3 are apparently a consequence of the confined pore geometry available for the adsorbed molecules. Alternatively, or perhaps in combination, the entropy of adsorption may increase with coverage more rapidly for ZTC-3 (the underlying changes in molecular dynamics could be studied with deuterated methane).

An accurate assessment of the contribution of intermolecular interactions to $q_{st}$ requires knowledge about the adsorption energies of the different surface sites. The most favorable sites contribute to the adsorption at low coverage in the Henry's law regime, but a heterogeneity of site energies as in MSC-30 is reflected in the relatively rapid decrease of $q_{st}$ with θ. The material properties of ZTC-3, such as a narrow distribution of pore-width, periodic pore-spacing, and high content of $sp^2$ hybridized carbon (as characterized by NMR and numerous other techniques), suggest a high homogeneity of binding site energies. It was expected that the increase of 1.1 kJ mol$^{-1}$ in $q_{st}$ at 238 K reflects most of the contribution from favorable intermolecular interactions, and in fact this increase is in good agreement with calculations of lateral interactions of methane molecules on a surface.

An isosteric enthalpy of adsorption that increases with θ over a large range of T and P is highly desirable for a methane adsorbent material. It benefits deliverable storage capacity because a large fraction of the maximum adsorption capacity occurs at pressures above the lower bound of useful storage rather than below it, as occurs for materials with a high initial binding energy that decreases with loading. Indeed, the deliverable gravimetric methane capacities of ZTC-3 at temperatures near ambient are the highest of any reported carbonaceous material (see below). The flexibility of the templatecarbonization synthesis allows pore-widths to be adapted to other adsorptive gases by simply changing the template, making this a promising approach for the design of adsorbent materials for other gases with attractive intermolecular interactions.

Figure Descriptions.

FIG. 4 provides data showing isosteric enthalpy of adsorption of methane on CNS-201, MSC-30, and ZTC-3 from 238-523 K (color indicates the temperature from low to high as blue to red). Scale bars of the fractional site occupancy, e, (specific to each material) are inset.

Figure 6:
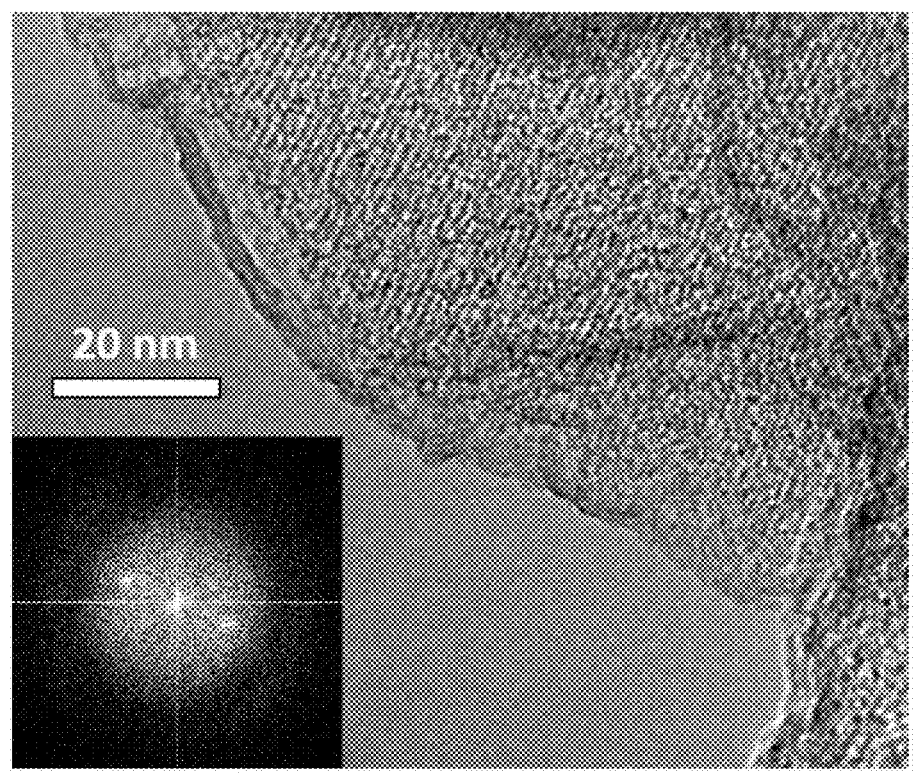
FIG. 6 depicts a TEM micrograph of a zeolite-templated carbon and a Fourier transform of the image (inset), showing the ordered pore size and inter-pore spacing.

FIG. 6 depicts a TEM micrograph of ZTC-3 confirming a pore-to-pore periodicity of 1.0 nm, and the Fourier transform of the image (inset).

FIGS. 7A-7C provides data showing Equilibrium excess adsorption isotherms of methane on CNS-201 (FIG. 7A), MSC-30 (FIG. 7B), and ZTC-3 (FIG. 7C) between 0-9 MPa at all temperatures measured: experimental data (diamonds) and fitted results (lines).

Figure 8:
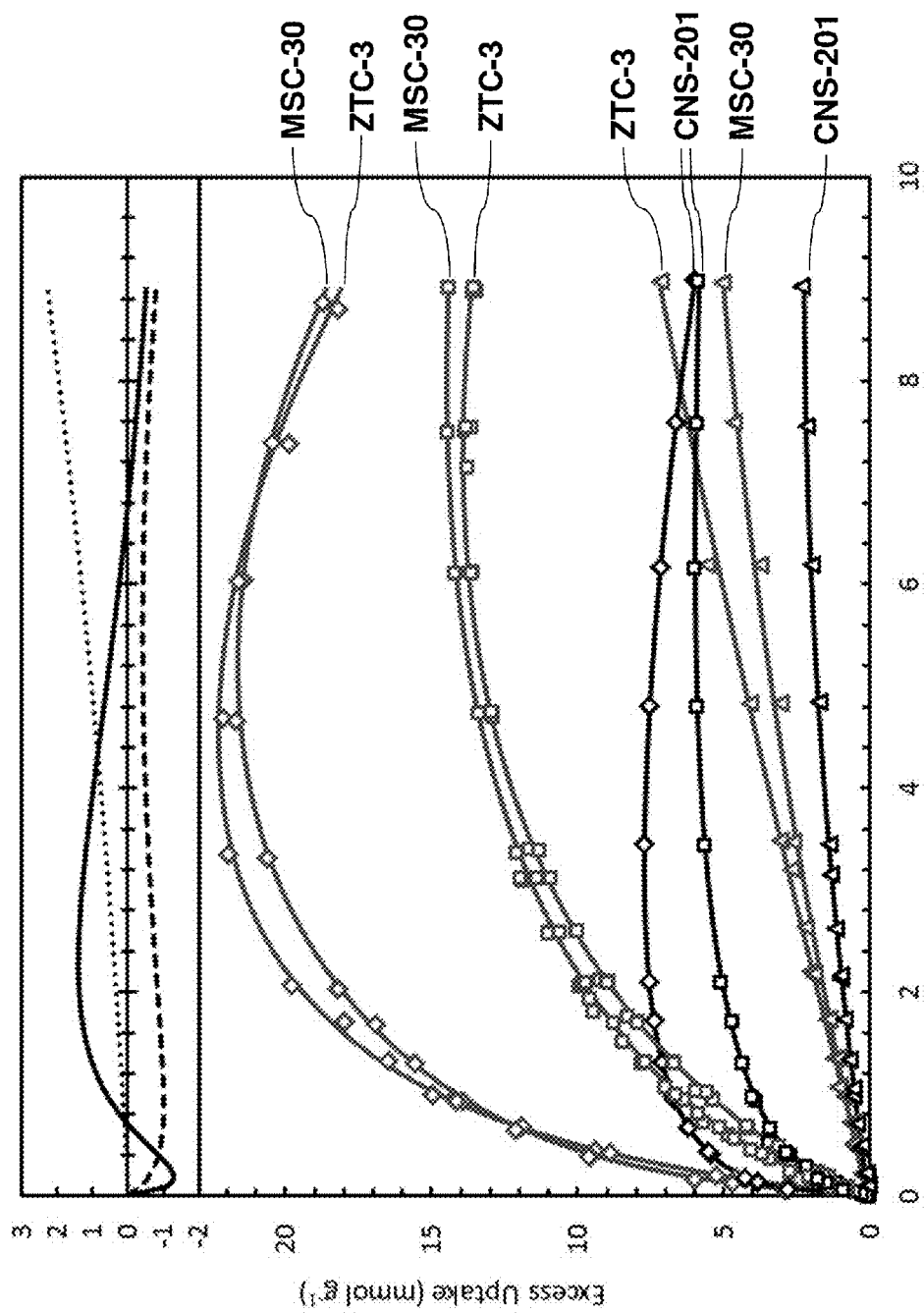
FIG. 8 provides data comparing equilibrium excess adsorption isotherms of methane between various adsorbents (the adsorbent type is indicated by color) at three specific temperatures relevant to storage (temperature is indicated by the open symbol type). The difference between two specific adsorbents with similar surface areas is shown at the top for the three corresponding temperatures, showing how the thermodynamic quantities play a more important role at the low (and high) temperature extremes while surface area (or number of sorption sites) plays a more important role at middle temperatures. It distinctly shows the advantage of ZTC-3 over MSC-30 at low temperatures where the deliverable capacity is dramatically improved.

FIG. 8 provides data showing a comparison of equilibrium excess adsorption isotherms of methane on CNS-201 (black), MSC-30 (red), and ZTC-3 (purple) at 238 K (diamond), 298 K (square), and ~523 (triangle). The actual temperatures near 523 K are as given in FIG. 7. The difference between ZTC-3 and MSC-30 is shown at the top: 238 K (full line), 298 K (dashed line), ~523 K (dotted line).

Figure 9A:
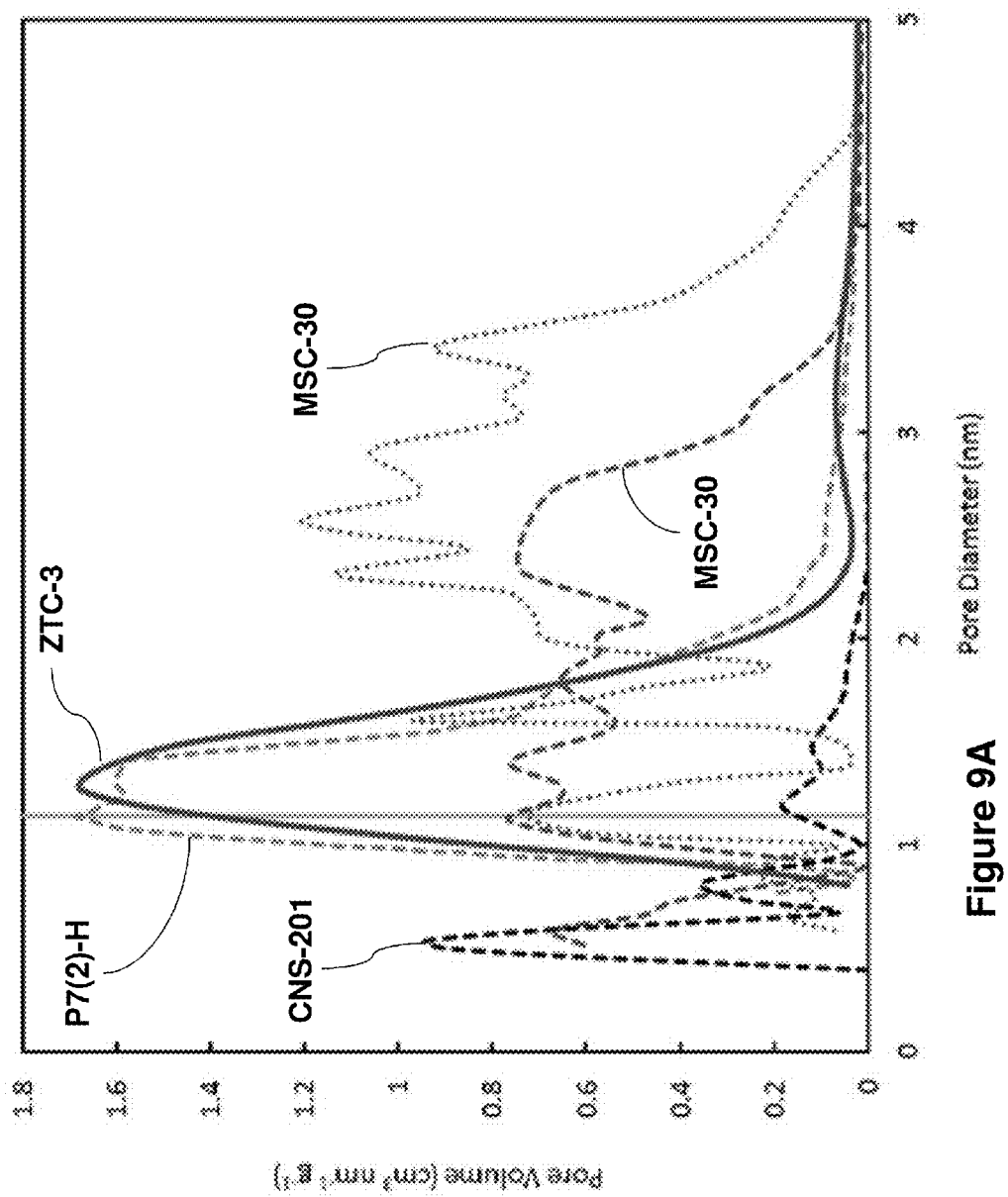
FIG. 9A provides data illustrating the pore-size distribution and FIG. 9B provides data illustrating the relative filling of various adsorbents.
Figure 9B:
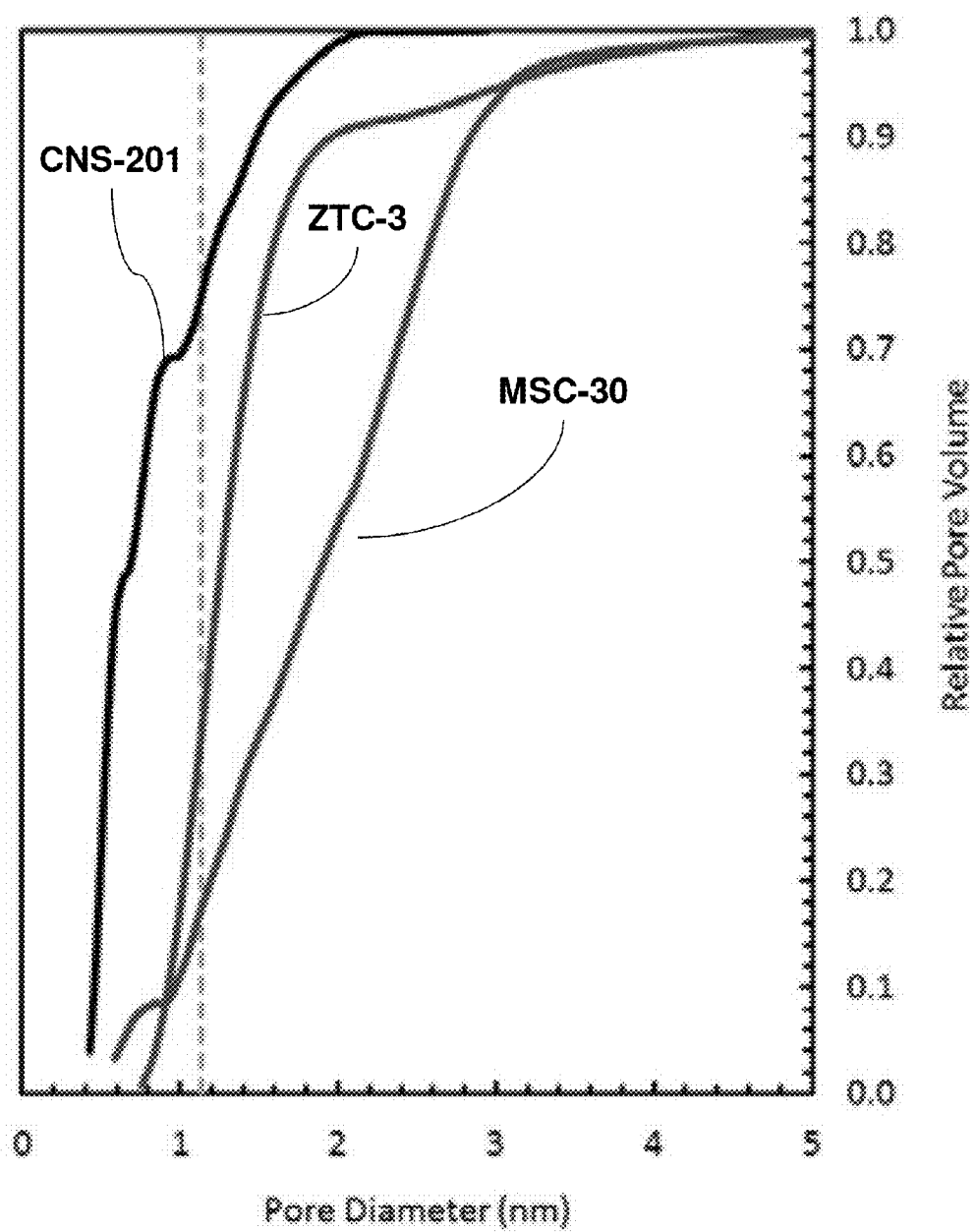
Figure 10C:
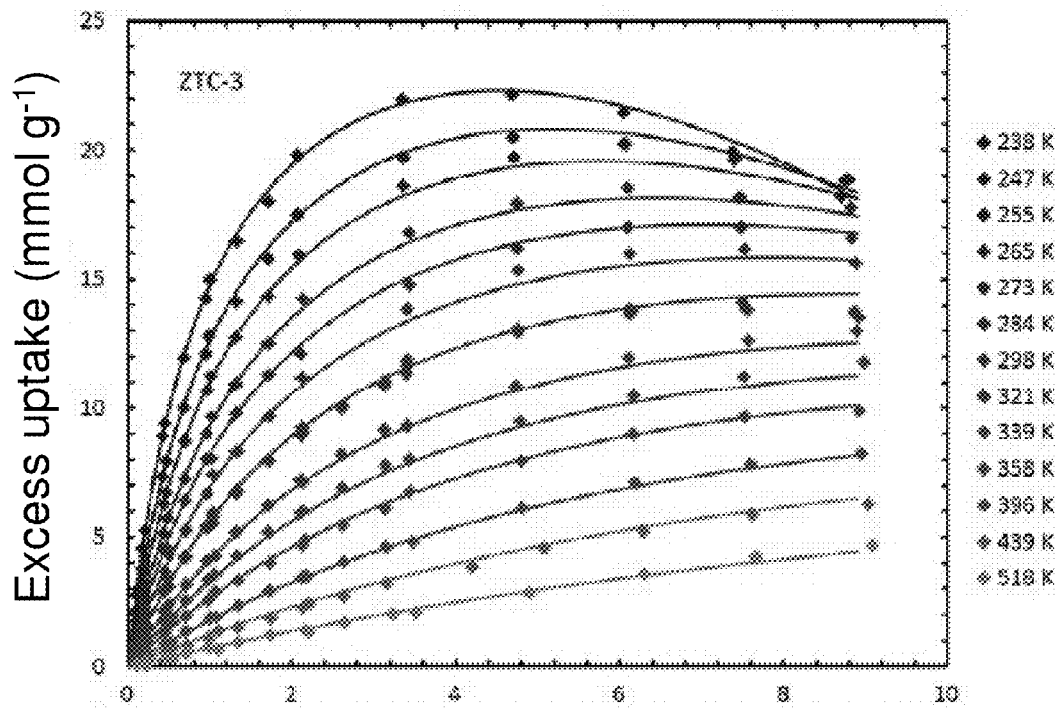
Figure 10D:
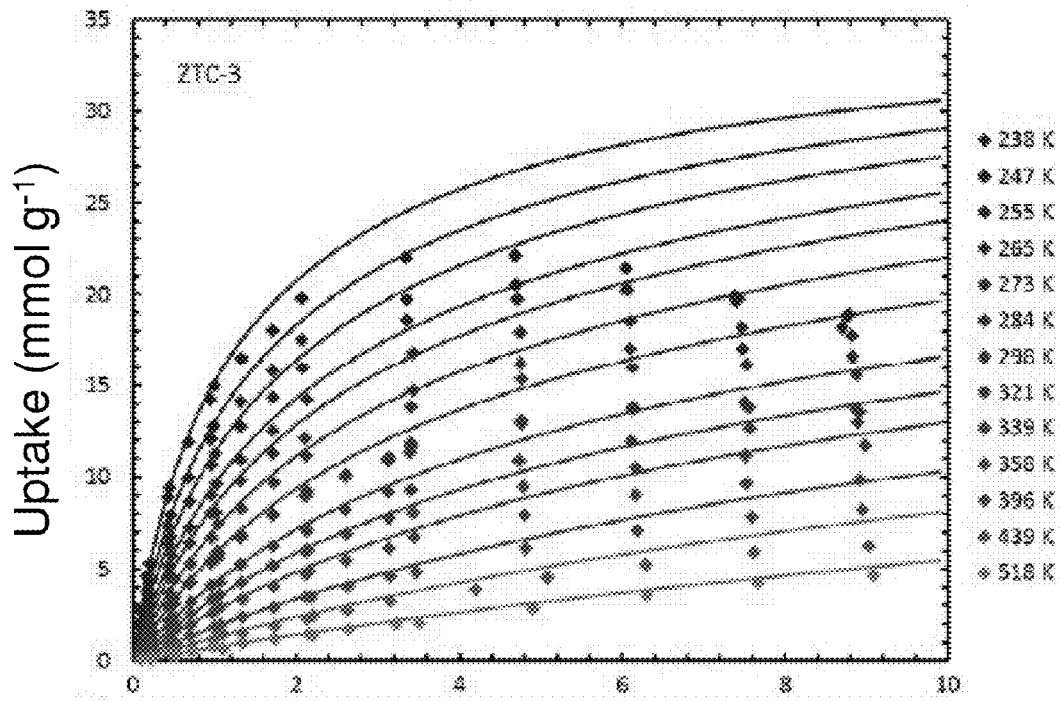
Figure 10E:
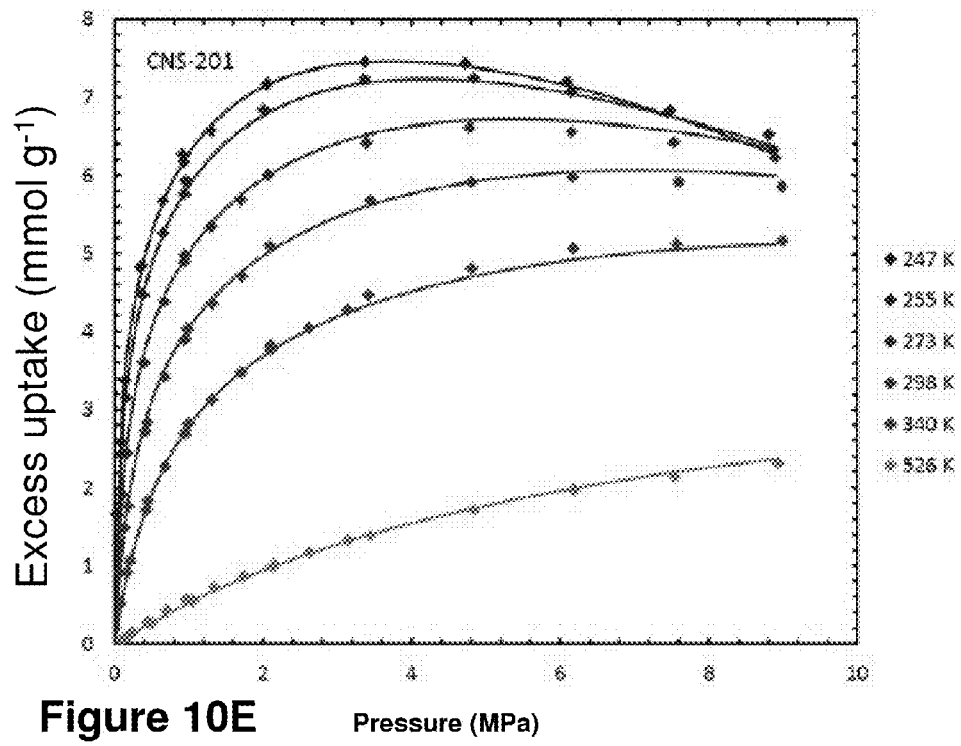
Figure 10F:
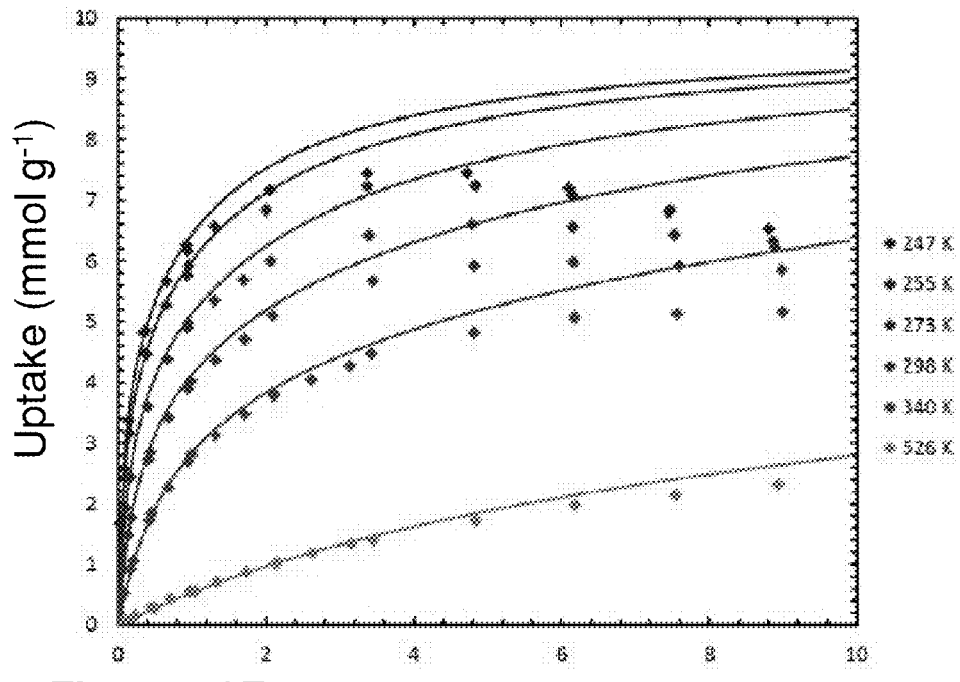

FIG. 9A provides data illustrating the pore-size distribution and FIG. 9B provides data illustrating relative filling of CNS-201 (black), MSC-30 (red), ZTC "P7(2)-H" (blue), and ZTC-3 (purple), calculated by the NLDFT method.

FIGS. 10A-10F. The complete set of experimental data, fitted to a double-Langmuir equation, of MSC-30 (FIGS. 10A and 10B), ZTC-3 (FIGS. 10C and 10D), and CNS-201 (FIGS. 10E and 10F): the fit results of excess uptake (FIGS. 10A, 10C and 10E) and absolute uptake (FIGS. 10B, 10D and 10F) at temperatures from 238-526 K (blue to orange—generally top to bottom) as a function of pressure (MPa). The diamonds are measured (excess) uptake.

Figure 11A:
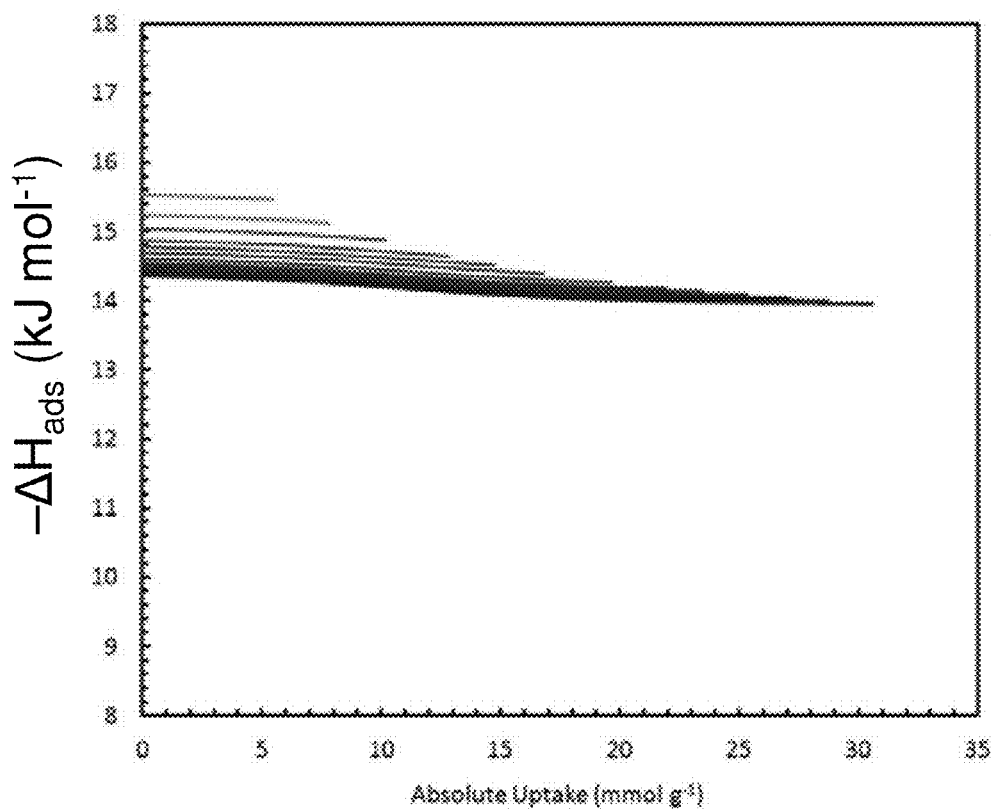
FIGS. 11A and 11B provide data showing isosteric enthalpy of adsorption, calculated using a double-Langmuir fit.
Figure 11B:
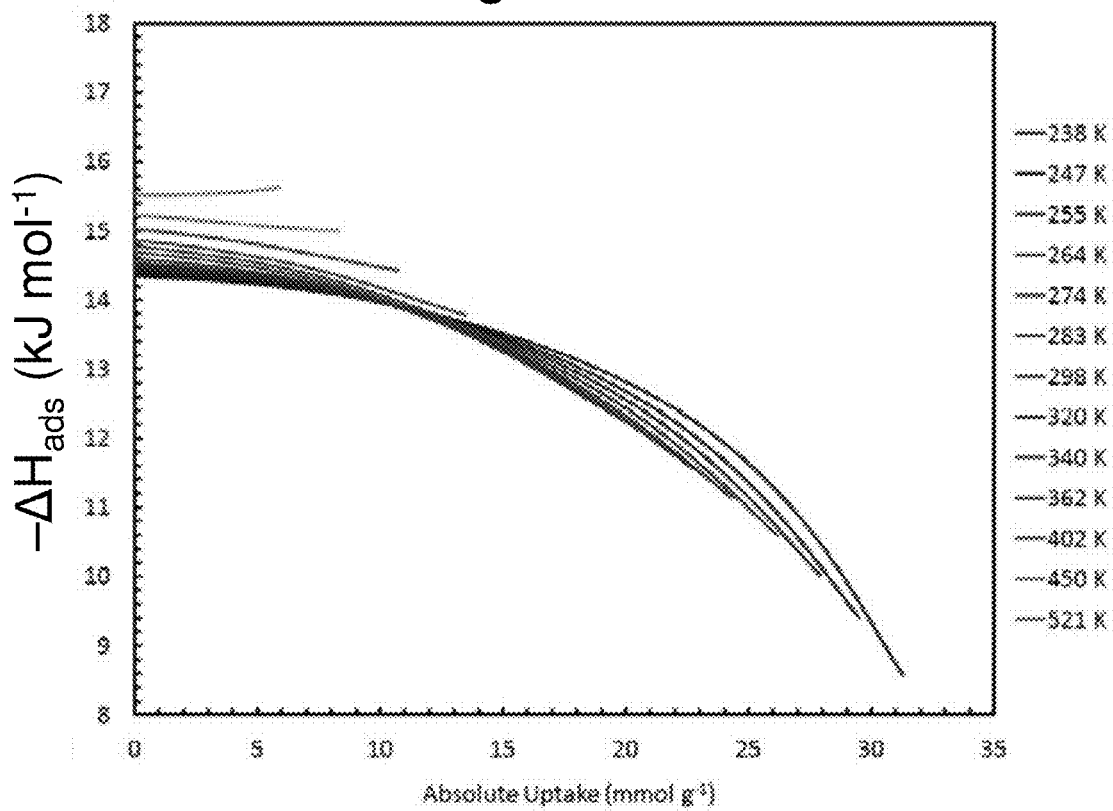

FIGS. 11A and 11B. Isosteric enthalpy of adsorption of methane, calculated using a double-Langmuir fit: (FIG. 11A) with the ideal gas assumption (Eq. 7), and (FIG. 11B) with the real gas density (Eq. 6), both employing the typical molar volume assumption.

Figure 12A:
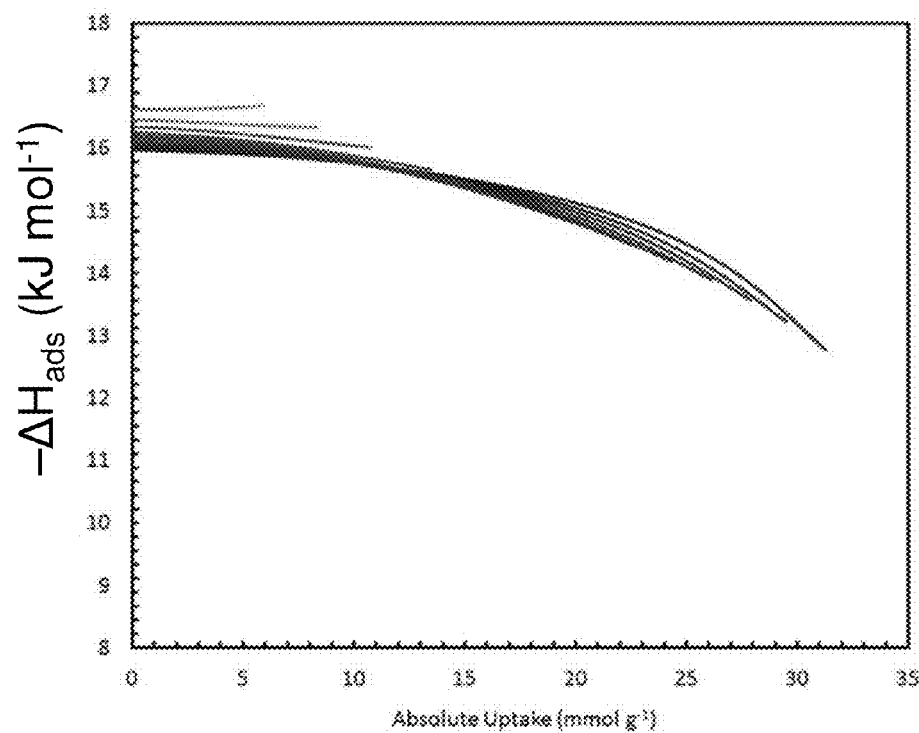
FIGS. 12A and 12B provide data showing isosteric enthalpy of adsorption, calculated using a double-Langmuir fit (FIG. 12A) and using a finite adsorbed phase molar volume equal to that of liquid methane (FIG. 12B).
Figure 12B:
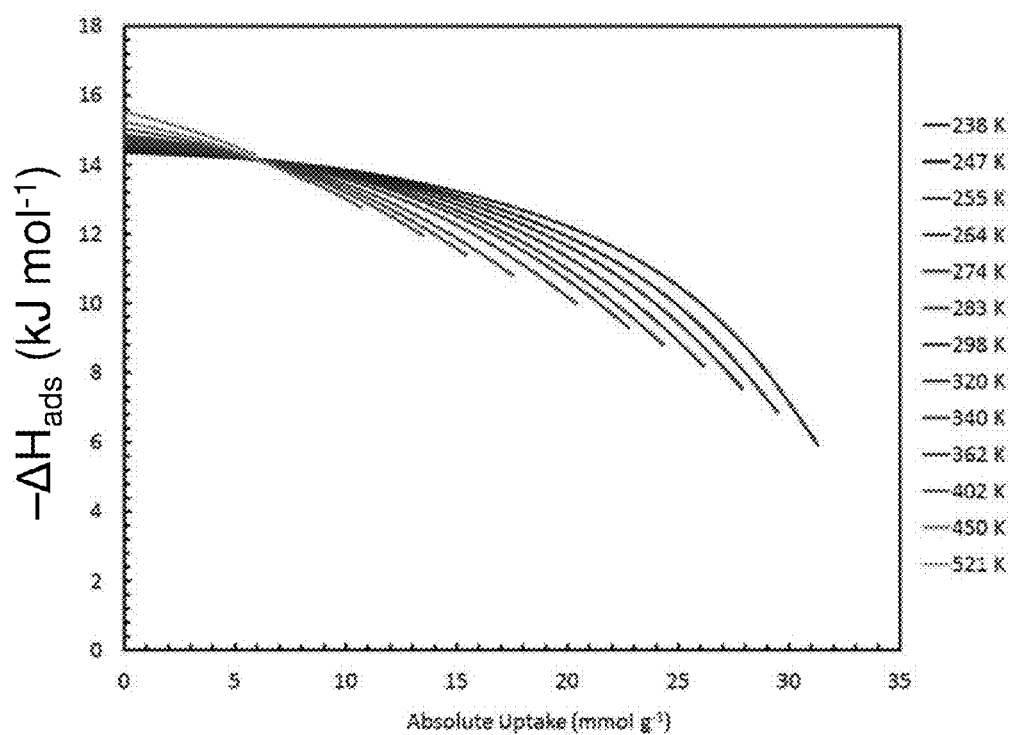
Figure 13:
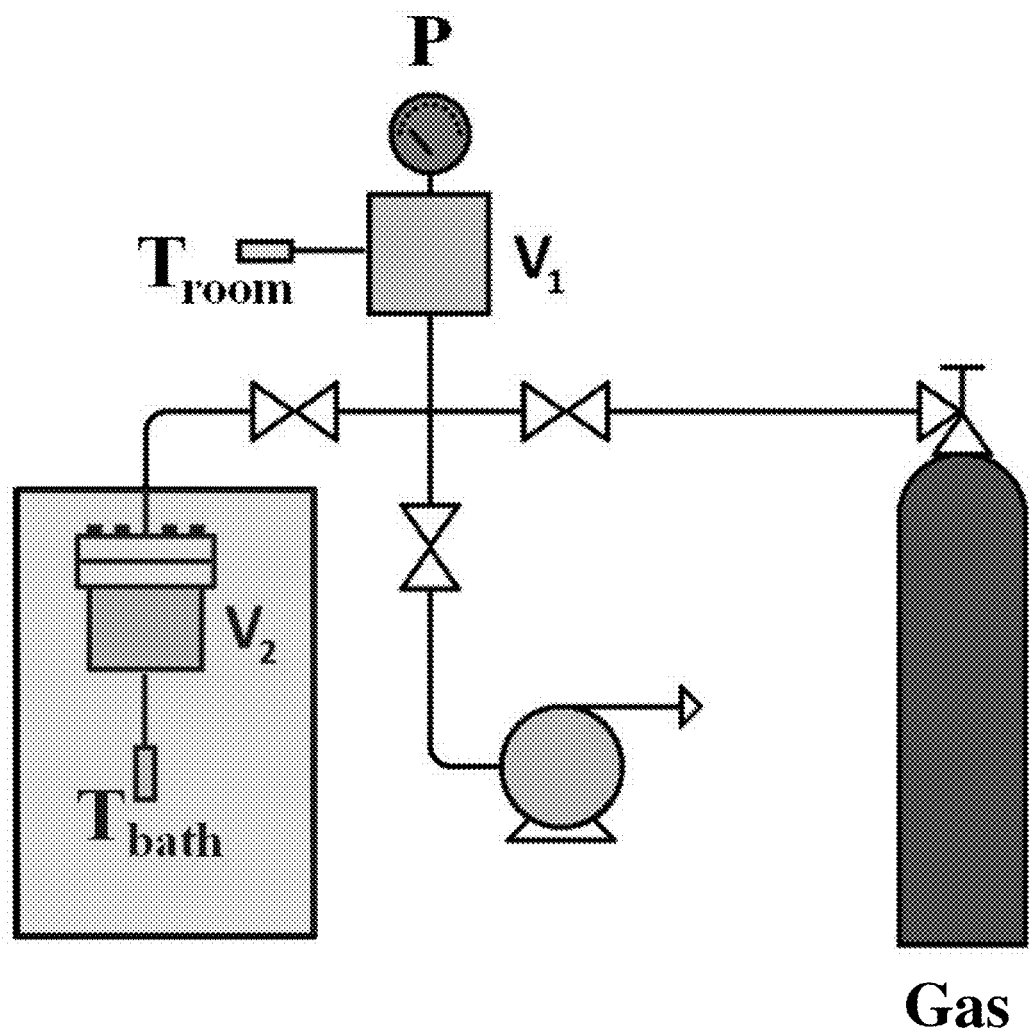
FIG. 13 provides a schematic illustration of an apparatus for volumetric adsorption measurements.
Figure 14A:
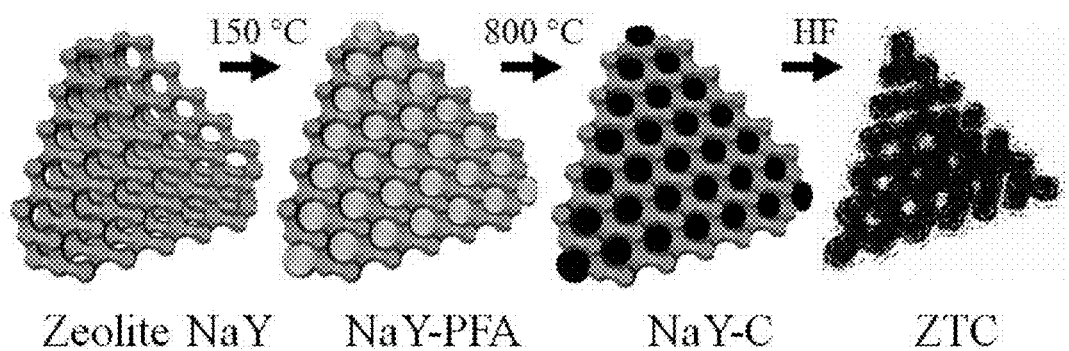
FIG. 14A depicts an overview of a method for creating a zeolite-templated carbon.
Figure 14B:
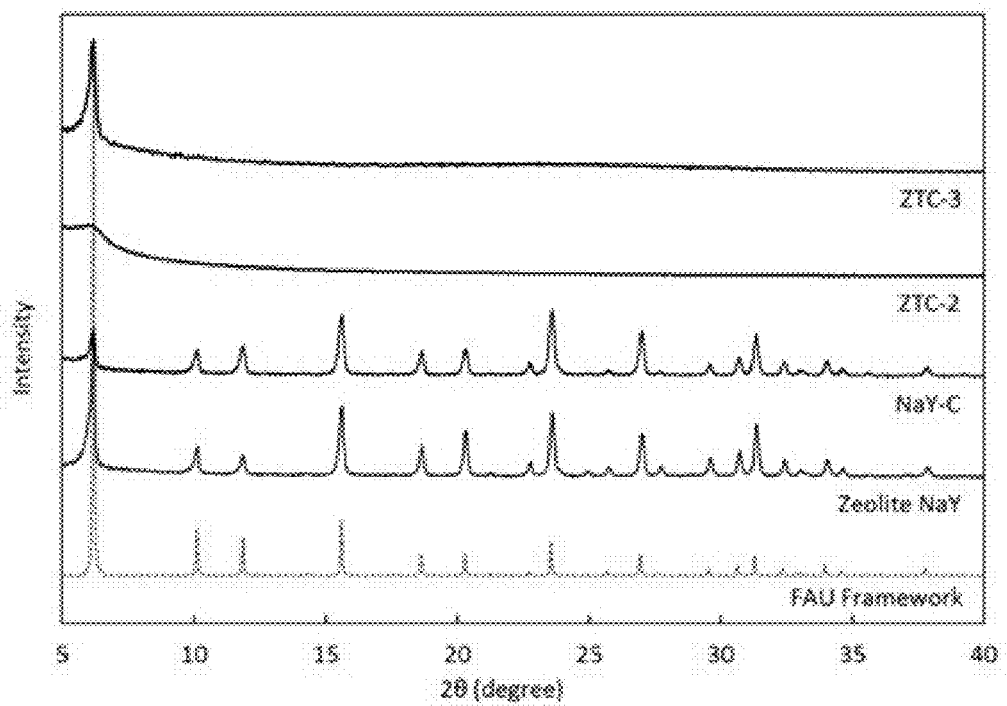
FIG. 14B depicts powder X-ray diffraction data of each material after the corresponding steps shown in FIG. 14A. The topmost diffraction pattern shows the long-range order between pores exhibited by ZTC-3.

FIGS. 12A and 12B. Isosteric enthalpy of adsorption of methane on MSC-30, calculated using a double-Langmuir fit: (FIG. 12A) with the common molar volume assumption (Eq. 6), and (FIG. 12B) using a finite adsorbed phase molar volume equal to that of liquid methane (Eq. 5), both using real gas density in the bulk gas phase.

Figure 15:
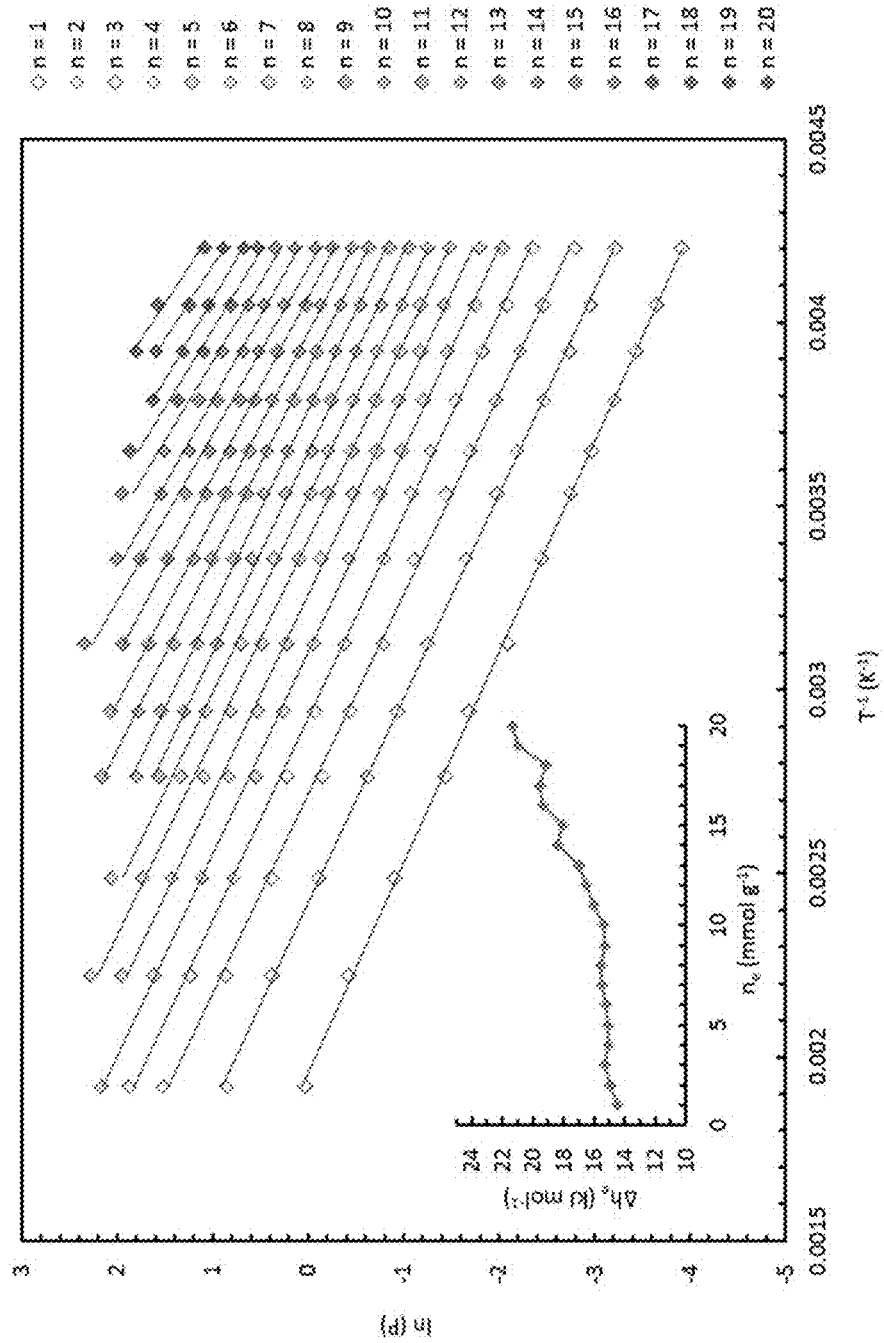
FIG. 15 provides data showing a van't Hoff plot of the pressure corresponding to a specific excess methane adsorption amount on MSC-30 as a function of inverse temperature.

FIG. 15 provides data showing a van't Hoff plot of the pressures corresponding to specific amounts of excess methane adsorption on MSC-30 as a function of inverse temperature, where the excess uptake amount was fitted with a simple linear interpolation. The linear regression fit of the van't Hoff plot gives a calculation of the isoexcess enthalpy of adsorption of methane on MSC-30 as a function of excess uptake (inset), a primitive method for approximating the actual isosteric enthalpy of adsorption.

Figure 16:
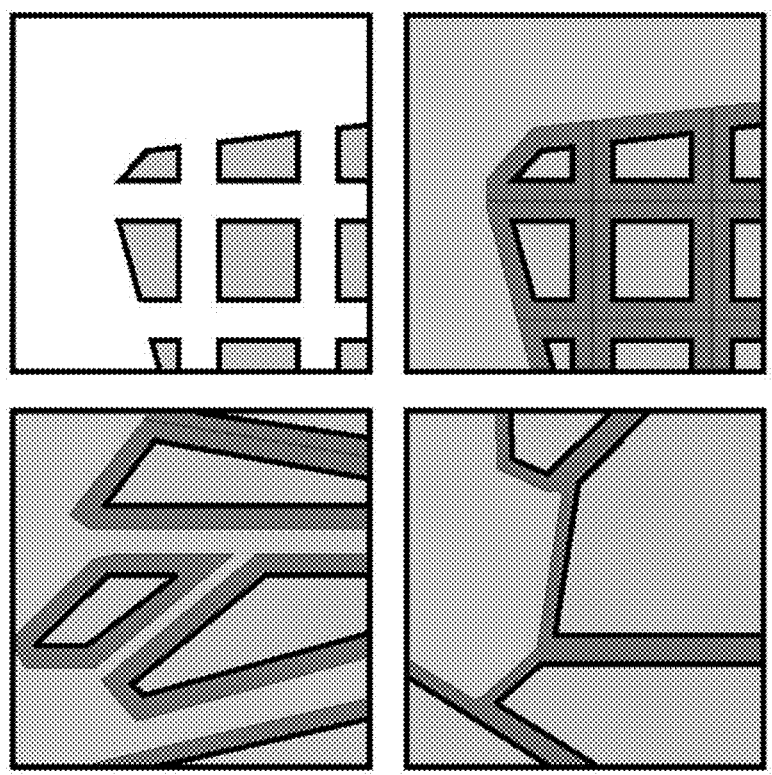
FIG. 16 provides a schematic illustration of surface adsorption in three archetypal adsorbent systems.

FIG. 16 provides a schematic illustration of surface adsorption in three archetypal adsorbent embodiment systems: (top right) a material with ordered, homogeneous pore widths each corresponding to twice the thickness of the adsorbed layer, with no adsorption on this material shown in the top left panel; (bottom left) a material with a distribution of pore widths mostly consisting of pores larger than twice the thickness of the adsorbed layer; and (bottom right) a material with a distribution of pore widths mostly consisting of pores smaller than twice the thickness of the adsorbed layer. The material in the top right is expected to have favorable thermodynamic characteristics of adsorption. In embodiments, the top right material is considered most representative of ZTC-3, the bottom left material is considered most representative of MSC-30, and the bottom right material is considered most representative of CNS-201.

Further Details for Example 2.

Additional materials characterization and data analysis were performed to supplement the results described above in this Example. They are discussed here along with experimental details related to the results presented above.

These additional results include cycling of methane adsorption in all three materials, verifying the full reversibility of methane uptake and exemplifying the precision between measurements. Relevant materials properties such as skeletal density, bulk density, and specific surface area are summarized. Elemental analysis experiments to determine the relative concentration of H in MSC-30 and ZTC-3 were performed, and the results are discussed in the context of the nature of the different skeletal density between the two materials. In specific embodiments, high relative concentrations of H in the carbonaceous adsorbent were desired for increasing the homogeneity of the surface, increasing the surface area, and/or decreasing the skeletal density of the material.

An important result reported in this Example is the increasing isosteric enthalpy of adsorption with increasing methane uptake in the zeolite-templated carbon, ZTC-3. This is an interesting deviation from expected behavior of high surface area carbon materials, that normally derive their properties from surface imperfections (edge terminations, defects, and surface roughness typically contribute to the extremely high surface area in carbons). There are numerous methods for determining the enthalpy of adsorption, and many common techniques lead to a perceived increase in enthalpy of adsorption even on materials for which an increase is unphysical. This is primarily because the interpolated data are subject to mathematical manipulation to calculate thermodynamic quantities of adsorption where small errors of the interpolated value lead to large deviations of the results. A robust procedure was employed for calculating the absolute adsorption quantities from experimental data which does not require any empirical knowledge of material properties (such as total pore volume or surface area) and is essentially model-independent. In this way, the isosteric enthalpy of adsorption was determined as a function of pressure and temperature, even at uptake quantities beyond the maximum in Gibbs surface excess where traditional methods show well-documented errors. Employing ideal-gas law assumptions or excess adsorption data instead of absolute both lead to incorrect interpretations of the isosteric thermodynamic quantities, and presented is a thorough comparison of the methods described herein to other methods to show that the increasing enthalpy of adsorption in ZTC-3 is a physical result and not an error of improper calculations.

The complete set of raw experimental data is included herein.

Materials Properties.

Maxsorb® MSC-30 superactivated carbon was obtained from Kansai Coke & Chemicals Company, Ltd. Activated carbon CNS-201 was obtained from A. C. Carbons Canada, Inc. All materials were degassed at 250° C. under vacuum to <0.1 mPa before use.

The details of material synthesis and principal materials properties of ZTC-3 were reported in N. P. Stadie, J. J. Vajo, R. W. Cumberland, A. A. Wilson, C. C. Ahn, and B. Fultz, 'Zeolite-templated carbon materials for high-pressure hydrogen storage', *Langmuir*, 28, 10057-63 (2012), hereby incorporated by reference, along with the details of materials characterization methods (nitrogen adsorption isotherms, transmission electron microscopy, x-ray diffraction, etc.). In summary, it was found that ZTC-3 has chemical properties similar to other ZTCs (being predominantly $sp^2$ hybridized carbon) and has very high template fidelity, having the structural traits of the best reported examples. Its hydrogen adsorption properties are among the highest of reported carbonaceous materials, but are proportional to surface area between 77-298 K as for other carbons. The narrow pore-size distribution centered at 1.2 nm is not optimized for hydrogen adsorption.

The materials properties relevant to the discussion of methane adsorption in this Example are summarized in Table 1. The skeletal densities are the average over 10 helium pycnometry measurements per sample, performed between 0-3 MPa and 298 K. The approximate bulk densities were measured at room temperature by packing a 1 mL volumetric flask over multiple trials. BET surface areas are reported. The excess methane capacities measured at 247, 298, and ~523 K from FIG. 8 are tabulated for comparison.

The skeletal density of ZTC-3, consistent with other ZTCs, is lower than the typical value expected for carbonaceous materials: 1.8 g mL$^{-1}$, 81% of the skeletal density of pure graphite. This can be explained by the significantly higher hydrogen content in ZTCs as determined by elemental analysis experiments. Elemental composition (CHN) of MSC-30 and ZTC-3 was determined by triplicate combustion experiments, using the Dumas method. Samples were prepared by degassing at 250° C. and sealed in foil packets in an argon glovebox with <1 ppm $H_2O$, a critical step for obtaining an accurate estimate of the H content since any adsorbed $H_2O$ would contribute to detected H. The results are summarized in Table 2. Average hydrogen content in ZTC-3 was 2.4 wt % H, approximately twice that in MSC-30:1.2 wt % H. If each atomic site where carbon is substituted for hydrogen retains its original skeletal volume, the difference in skeletal density would be 11%, a decrease from 2.1 to 1.9 g mL$^{-1}$. Additional decrease in skeletal density could be due to the presence of hanging C—H groups which have a larger atomic volume than a pair of $sp^2$ hybridized carbon atoms. This approximation gives a representative figure for the significance of increased H content to the skeletal density, an effect that is large enough to account for the difference between MSC-30 and ZTC-3.

TABLE 2

Elemental hydrogen concentration of MSC-30 and ZTC-3.

| Material | H (wt %) | Average (wt %) |
|---|---|---|
| MSC-30 | 0.74 | 1.16 |
|  | 1.32 |  |
|  | 1.42 |  |
| ZTC-3 | 2.78 | 2.44 |
|  | 2.47 |  |
|  | 2.08 |  |

DFT Pore-Size Comparison.

Nitrogen adsorption/desorption isotherms were measured at 77 K, and pore-size distributions were calculated by the non-local density functional theory (NLDFT) method using a carbon slit pore model and software provided by Micromeritics. A carbon cylindrical pore model was also analyzed, but did not fit the data as well as the slit pore model. The pore-size distributions in ZTC-3 and the commercial carbons are shown in FIG. 9A.

TABLE 1

Densities of, BET surface areas (SA) of, and excess uptake capacities of methane adsorption on CNS-201, MSC-30, and ZTC-3.

| Material | Skeletal Density$^\diamond$ (g mL$^{-1}$) | Bulk Density$^{\diamond\diamond}$ (g mL$^{-1}$) | BET Surface Area (m$^2$g$^{-1}$) | 247K CH$_4$ Capacity$^\dagger$ (mmol g$^{-1}$) | 298K CH$_4$ Capacity$^{\dagger\dagger}$ (mmol g$^{-1}$) | ~523K CH$_4$ Capacity$^{\dagger\dagger\dagger}$ (mmol g$^{-1}$) |
|---|---|---|---|---|---|---|
| CNS-201 | 2.1 | 0.50 | 1095 ± 8 | 7.45 | 5.98 | 2.48 |
| MSC-30 | 2.1 | 0.27 | 3244 ± 28 | 20.2 | 14.5 | 5.16 |
| ZTC-3 | 1.8 | 0.18 | 3591 ± 60 | 20.5 | 14.1 | 4.76 |

$^\diamond$Skeletal density measured using He at 298K between 0-3 MPa.

$^{\diamond\diamond}$Bulk density measured on maximum packing.

$^\dagger$Measured at 247K and Gibbs excess maximum pressure.

$^{\dagger\dagger}$Measured at 298K and Gibbs excess maximum pressure.

$^{\dagger\dagger\dagger}$Measured at 526, 521, and 518K for CNS-201, MSC-30, and ZTC-3, respectively, at 10 MPa.

It has been proposed that 1.14 nm is the optimal spacing between graphene layers for maximum adsorption uptake of methane. The pore-size distribution of ZTC-3 has a mean pore-width close to this value, shown as a gray line in FIG. 9A. The relative pore volume as a function of pore-width is shown in FIG. 9B, and ZTC-3 has the closest resemblance to an ideal step-function material with identical pores spaced at the optimal width.

Methane Adsorption Measurements and Cycling.

Methane adsorption isotherms at all temperatures were measured with a custom volumetric Sieverts apparatus, commissioned and verified for accurate measurements up to 10 MPa. The apparatus was equipped with a digital cold cathode pressure sensor (1-MAG, Series 423), a high-resolution pressure manometer (MKS Baratron, Model 120AA), a high pressure manometer (MKS Baratron, Model 833), and a molecular drag pump to achieve a measurable pressure range of $10^{-5}$ to $10^7$ Pa. Temperature was measured on the wall of the manifold and on the outer wall of the sample holder using K-type thermocouples and platinum resistance thermometers (PRTs). The sample was submerged in a chiller bath for sub-ambient temperature isotherms. For high temperatures, the sample was placed inside a cylindrical copper heat exchanger and wrapped with insulated fiberglass heating tape. A PID controller and K-type thermocouples were used to maintain a consistent temperature throughout measurement; fluctuations were less than ±0.1 K at low temperature and no higher than ±0.4 K at high temperatures. The system was leak tested up to 10 MPa and showed a maximum leak rate of $7.0 \times 10^{-6}$ mol h$^{-1}$ of $CH_4$. If fitted to an exponential decay function, $n(t)=n_0 \exp(-kt)$ where k is the leak rate, this corresponds to a maximum leak of k ~$10^{-8}$ s$^{-1}$ which is negligible for short time measurement. The total inner volume of the apparatus was 66 mL.

Research purity methane (99.999%), obtained from Matheson Tri-Gas Inc., was exposed to the sample at incrementally higher pressures over the course of each isotherm in regular equilibration steps, allowing 10-30 min between gas expansions to ensure thermal equilibration. The system was not returned to vacuum in between steps and the measured uptake was cumulative from step to step. Cumulative uptake at each step was corrected for background adsorption of the instrument by subtracting the amount of perceived uptake at the same pressure in an empty sample holder. Empty sample holder "adsorption" was measured at each temperature, and was <50% of total uptake (in grams) measured at all conditions in this Example, a value beyond which the accuracy of measurements was assumed to be compromised. Gas densities were determined from temperature and pressure using the REFPROP Standard Reference Database.

Prior to methane adsorption measurements, 0.3-1.5 g of sample was loaded and degassed at 250° C. under vacuum to <0.1 mPa for 12 h. Two adsorption runs were performed at each temperature and the combined data was tabulated for thermodynamic analysis. Complete adsorption/desorption cycles were also performed at various temperatures to assure full reversibility of methane physisorption in the complete temperature/pressure regime of study and to test the precision of the experiments. Error between cycles was <1% of the measured value.

Adsorption/desorption cycling in all materials was achieved without any loss of capacity after many cycles, as expected for pure physisorbent materials. For example, three independent (non-consecutive) hydrogen adsorption/desorption cycles in ZTC-3 at 298 K were measured. The sample was degassed once before cycling but was not further treated between cycles. Equilibrium adsorption isotherms at 238, 298, and ~523 K are shown in FIG. 8 for a direct comparison between the materials.

Isosteric and Isoexcess Equations of Adsorption.

The following is a derivation of the thermodynamic quantities of interest for studies of high pressure methane adsorption. The change in entropy upon adsorption, $\Delta S_{ads}$, can be calculated as a function of adsorption uptake, $n_a$, by the isosteric method (analogous to the Clausius-Clapeyron relation):

$$\left(\frac{dP}{dT}\right)_{n_a} = \frac{(s_a - s_g)}{(v_a - v_g)} \qquad \text{eq. 1}$$

A typical assumption that accurately describes many experimental systems sets the change in molar volume as that of the gas phase change alone:

$$v_a - v_g \approx v_g \qquad \text{eq. 2}$$

Rather, a more accurate approximation is suggested:

$$v_a - v_g \approx v_{liq} - v_g \qquad \text{eq. 3}$$

This becomes an important distinction at high pressure. Here, use the molar volume of methane at 0.1 MPa and 111.5 K, $v_{liq}=38$ mL mol$^{-1}$ is used. Then:

$$\left(\frac{dP}{dT}\right)_{n_a} = \frac{(s_a - s_g)}{v_{liq} - v_g} \qquad \text{eq. 4}$$

$$\Delta S_{ads}(n_a) = \left(\frac{dP}{dT}\right)_{n_a}(v_{liq} - v_g)$$

$$\Delta H_{ads}(n_a) = T\Delta S_{ads} = T\left(\frac{dP}{dT}\right)_{n_a}(v_{liq} - v_g) \qquad \text{eq. 5}$$

There are numerous approximations that can be used to simplify this expression. The most common is to assume the adsorbed molar volume is negligible relative to the gas. This gives:

$$\Delta H_{ads}(n_a) = T\left(\frac{dP}{dT}\right)_{n_a}(-v_g) = -T\left(\frac{dP}{dT}\right)_{n_a}(\rho_g)^{-1} \qquad \text{eq. 6}$$

In the ideal gas approximation (where the molar volume approximation is also kept):

$$\Delta H_{ads}(n_a) = -T\left(\frac{dP}{dT}\right)_{n_a}\left(\frac{RT}{P}\right) = -\left(\frac{RT^2}{P}\right)\left(\frac{dP}{dT}\right)_{n_a} \qquad \text{eq. 7}$$

This is commonly rearranged in the van't Hoff form:

$$\Delta H_{ads}(n_a) = R\left(\frac{d\ln P}{d\left(\frac{1}{T}\right)}\right)_{n_a} \qquad \text{eq. 8}$$

The isosteric heat of adsorption is given a positive value (and it is common to report the "enthalpy" in this way as well), equal to $-\Delta H_{ads}$. In summary:

| Assumptions: | Isosteric Method | "Isoexcess" Method ($n_a \approx n_e$) |
|---|---|---|
| Ideal Gas $\Delta v_{ads} \approx -v_g$ | $-\Delta H_{ads}(n_a) = -\left(\dfrac{RT^2}{P}\right)\left(\dfrac{dP}{dT}\right)_{n_a}$ | $-\Delta H_{ads}(n_e) = -R\left(\dfrac{d\ln P}{d\left(\dfrac{1}{T}\right)}\right)_{n_e}$ |
| Non-ideal Gas $\Delta v_{ads} \approx -v_g$ | $-\Delta H_{ads}(n_a) = T\left(\dfrac{dP}{dT}\right)_{n_a} \rho_g^{-1}$ | $-\Delta H_{ads}(n_e) = T\left(\dfrac{dP}{dT}\right)_{n_e} \rho_g^{-1}$ |
| Non-ideal Gas $\Delta v_{ads} \approx v_{liq} - v_g$ | $-\Delta H_{ads}(n_a) = T\left(\dfrac{dP}{dT}\right)_{n_a} (v_g - v_{liq})$ | $-\Delta H_{ads}(n_e) = T\left(\dfrac{dP}{dT}\right)_{n_e} (v_g - v_{liq})$ |

Another relevant set of equations are given for the "isoexcess" approximation, where the measured (excess) quantity of adsorption is used in the place of the absolute quantity. The limitations of each approximation, and the results from their analysis, are discussed below. The results were sensitive not only to the equation used above, but also to the fitting technique for data interpolation.

Thermodynamic Analysis of Adsorption Isotherm Data.

Adsorption isotherms are measured at a set of fixed temperatures. The resulting data gives a relationship between the equilibrium pressure and the excess uptake amount, $n_e$, at each temperature, and can be used in the above described equations to calculate the isoexcess enthalpy of adsorption. However, the uptake amount is not fixed, and interpolation of the data is necessary to determine the equilibrium pressure at an arbitrary uptake amount. A number of different methods were compared to interpolate the data measured in this Example:

1. No fitting, approximate isoexcess method
2. Linear interpolation, isoexcess method
3. Virial-type fitting equation, isoexcess method
4. Langmuir-type fitting equation, isoexcess method
5. Langmuir-type fitting equation, isosteric method A comparison was performed for the data of methane adsorption on CNS-201, MSC-30, and ZTC-3 to determine the effects of each method on the results, and a detailed description is given in N. P. Stadie, 'Synthesis and thermodynamic studies of physisorptive energy storage materials', thesis, California Institute of Technology (2012), hereby incorporated by reference. The data collected in this example is one of the largest sets available of methane adsorption on carbon. A summary of the results is given below, and a complete description of the method adopted follows.

The interpolation of adsorption data in the high pressure limit is very sensitive to the method used, and small deviations from the true value cause significant errors in the thermodynamic calculations. All methods give a visually good approximation to the experimental data at low pressure in this data set. The high pressure regime is where the methods differ significantly. The first distinction is made between using the excess adsorption data itself (the isoexcess approximation), and employing a model to determine the absolute adsorption. Using the excess adsorption quantity for thermodynamic calculations is an acceptable practice for studies of adsorption well below the critical point (low pressure and temperature) where excess and absolute adsorption quantities are approximately equal. However, at temperatures and pressures near the critical point and above, thermodynamic calculations from excess adsorption data lead to well-documented errors. The enthalpy of adsorption calculated in the high coverage regime often shows an unphysical steep increase that is associated with the use of the excess quantity. It is simple to show that if $n_e < n_a$, the slope of the excess isosteres in the van't Hoff plot will be more negative than that of the correct absolute isosteres (since the pressure necessary to achieve a given state of uptake will be underestimated), effecting an apparent increase in the calculated enthalpy of adsorption. Pitfalls such as these are either ignored, or the data beyond moderate quantities of surface coverage are discarded. In either case, the isosteric enthalpy is not accessible for high pressures, and quantities calculated using excess uptake data must be referred to as "isoexcess" quantities. Within the context of the isoexcess approximation, the four methods listed above perform satisfactorily for determining the average Henry's law value of the enthalpy of adsorption, and can be used as a standard for comparing the Henry's law result from the isosteric method detailed below. The only method that successfully determines the isoexcess enthalpy of adsorption beyond the Gibbs surface maximum is that using a monotonically increasing fitting function in the context of the Gibbs definition of surface excess. A generalized Langmuir equation is used in this Example, but other monotonically increasing fitting equations have also been employed with successful results.

To understand the true thermodynamic quantities of adsorption from experimentally measured adsorption data, a model is necessary to determine the absolute adsorption amount as a function of pressure. The necessary variable that remains unknown is the volume of the adsorption layer and numerous methods have been suggested to estimate it. Typical methods include fixing the volume of adsorption as the total pore volume of the sorbent material, using a volume proportional to the surface area (assuming fixed thickness), or deriving the volume by assuming the adsorbed layer is at liquid density. Some approaches are specific to graphite-like carbon materials, such as the Ono-Kondo model. The most general approach is to let the adsorption volume be an independent parameter of the fitting equation of choice. The generalized-Langmuir equation, the Langmuir-Freundlich equation, and the Unilan equation have been shown to be suitable fitting equations for determining absolute adsorption from excess uptake isotherms since they are monotonically increasing and contain a relatively small number of fitting parameters to achieve a satisfactory fit to the experimental data. This Example adopts a generalized-Langmuir fitting equation, and finds that two superimposed Langmuir equations are sufficient to fit the data for the materials in this Example.

Generalized-Langmuir Model of Adsorption.

The Gibbs definition of excess adsorption as a function of absolute adsorption, $n_a$, is:

$$n_e = n_a - V_{ads}\rho_g(P,T) \qquad \text{eq. 12}$$

An effective strategy is to choose a functional form for $n_a$ that is monotonically increasing with pressure, consistent with the physical nature of adsorption. The Langmuir isotherm is one example. If an arbitrary number of Langmuir isotherms are superpositioned, referred to as a generalized-Langmuir equation, the number of independent fitting parameters can be easily tuned to suit the data. In this method, absolute adsorption takes the form:

$$n_a(P, T) = n_{max} \sum_i \alpha_i \left( \frac{K_i P}{1 + K_i P} \right) \quad \text{eq. 13}$$

$$\sum_i \alpha_i = 1$$

The parameter $n_{max}$ is a scaling parameter, to convert the unitless quantity of adsorption to relevant units. The $\alpha_i$ are weights of the component Langmuir equations. The $K_i$ are the equilibrium constants of adsorption in the classical Langmuir model. They are constant with pressure but have a dependence on temperature. An Arrhenius equation is a simple and accurate description, also a form arrived at by statistical methods, to define the adsorption constants, $K_i$, as:

$$K_i = \frac{A_i}{\sqrt{T}} e^{\frac{E_i}{RT}} \quad \text{eq. 14}$$

The volume of the adsorbed layer in the Gibbs equation also has a pressure dependence that is fundamentally unknown, but which is generally accepted to be monotonically increasing in most systems. It too can be approximated by a generalized Langmuir equation, greatly simplifying the final fitting equation and keeping the number of fitting parameters low:

$$V_{ads}(P, T) = V_{max} \sum_i \alpha_i \left( \frac{K_i P}{1 + K_i P} \right) \quad \text{eq. 15}$$

The parameter $V_{max}$ is the volume of the adsorption layer at maximum adsorption occupancy. The excess adsorption data are then fitted to:

$$n_e(P, T) = n_{max} \sum_i \alpha_i \left( \frac{K_i P}{1 + K_i P} \right) - \left( V_{max} \sum_i \alpha_i \left( \frac{K_i P}{1 + K_i P} \right) \right) \rho(P, T) \quad \text{eq. 16}$$

$$n_e(P, T) = (n_{max} - V_{max} \rho(P, T)) \left( \sum_i \alpha_i \left( \frac{K_i P}{1 + K_i P} \right) \right)$$

The total number of fitting parameters ($n_{max}$, $V_{max}$, $\alpha_i$, $A_i$, and $E_i$) is 3i+1. If the ideal gas law applies to the pressure and temperature regime of interest, the equation simplifies:

$$n_e(P, T) = \left( n_{max} - V_{max} \frac{P}{RT} \right) \left( \sum_i \alpha_i \left( \frac{K_i P}{1 + K_i P} \right) \right) \quad \text{eq. 17}$$

The experimental data of methane adsorption on MSC-30 was fitted by a double-Langmuir isotherm (i=2) with the ideal gas assumption. For all but the highest pressures (P>6 MPa) at low temperatures, the data are well approximated by this method. The interpolation between points, even near or at the Gibbs excess maximum, is representative of the physical nature of the system, and the extrapolation to high pressures shows much improved behavior compared to that of a virial-type fitting equation. A limitation of the ideal gas assumption is that the excess uptake isotherms cannot cross at high pressure, the lowest temperature data decreasing proportionally with pressure. However, this is not consistent with experimental results where it frequently occurs that low temperature data falls significantly below higher temperature data at the same pressure. This is entirely due to non-ideal gas interactions from a nonlinear change in gas density, and can be accounted for by using the more general equation (Eq. 16).

The experimental data of methane adsorption on MSC-30 was fitted using one, two, and three superimposed Langmuir isotherms (with 4, 7, and 10 independent parameters, respectively) and using the real gas density for the bulk methane gas phase. A single Langmuir equation (i=1) does not accurately fit the data. The double-Langmuir fit is satisfactory in the logarithmic plot of $P/n_e$, and is the preferred method in this Example. The high pressure data are significantly better fitted by using the real gas density, and extrapolation of the low temperature data to pressures up to 15 MPa shows behavior consistent with that expected for excess adsorption at in these conditions. The triple-Langmuir fit is not a significant improvement, and cannot be justified for this data since a minimum number of independent parameters is desired. The reduced equation for i=2 is:

$$n_e(P, T) = (n_{max} - V_{max} \rho(P, T)) \left( (1 - \alpha) \left( \frac{K_1 P}{1 + K_1 P} \right) + \alpha \left( \frac{K_2 P}{1 + K_2 P} \right) \right) \quad \text{eq. 18}$$

The assumption that the total adsorption volume scales proportionally with site occupancy is robust in this Example, and this fitting equation has been previously shown to be successful for both carbonaceous and MOF materials. This Example refers to this method (using i=2) as the double-Langmuir method, and if the absolute quantity of adsorption is held constant, it yields the true isosteric quantities of adsorption. The absolute quantity, from the Gibbs definition, is:

$$n_a(P, T) = n_{max} \left( (1 - \alpha) \left( \frac{K_1 P}{1 + K_1 P} \right) + \alpha \left( \frac{K_2 P}{1 + K_2 P} \right) \right) \quad \text{eq. 19}$$

The fractional site occupancy, also called the surface coverage, is:

$$\theta(P, T) = (1 - \alpha) \left( \frac{K_1 P}{1 + K_1 P} \right) + \alpha \left( \frac{K_2 P}{1 + K_2 P} \right) \quad \text{eq. 20}$$

Least squares fits of all of the experimental data (on CNS-201, MSC-30, and ZTC-3) to the double-Langmuir equation are shown in FIGS. 10A-10F, the fitted excess adsorption (FIGS. 10A, 10C and 10E) and calculated absolute adsorption (FIGS. 10B, 10D and 10F) at all temperatures measured as a function of pressure (MPa). The goodness of fit was satisfactory across the entire range of temperature and pressure for all three samples, with a residual sum of squares less than 0.04 mmol g$^{-1}$ per data point. The optimal fitting parameters for each material are given in Table 3.

TABLE 3

Least-squares minimized fit parameters of the double-Langmuir equation for methane adsorption on CNS-201, MSC-30, and ZTC-3 from equilibrium excess adsorption data measured between 238-526 K.

| Material | $n_{max}$ (mmol g$^{-1}$) | $V_{max}$ (mL g$^{-1}$) | α | $A_1$ (K$^{1/2}$ MPa$^{-1}$) | $E_1$ (kJ mol$^{-1}$) | $A_2$ (K$^{1/2}$ Mpa$^{-1}$) | $E_2$ (kJ mol$^{-1}$) |
|---|---|---|---|---|---|---|---|
| CNS-201 | 9.77 | 0.49 | 0.58 | 0.061 | 17.2 | 0.0044 | 16.4 |
| MSC-30 | 41.0 | 2.30 | 0.70 | 0.068 | 13.4 | 0.0046 | 12.9 |
| ZTC-3 | 35.6 | 2.04 | 0.46 | 0.059 | 11.6 | 0.00018 | 20.4 |

To derive the isosteric enthalpy from the double-Langmuir equation, the derivative of pressure with respect to temperature is decomposed as follows:

$$\left(\frac{\partial P}{\partial T}\right)_{n_a} = \left(\frac{\partial \theta}{\partial P}\right)_{n_a}^{-1} \left(\frac{\partial \theta}{\partial K}\right)_{n_a} \sum_i \left(\frac{\partial K_i}{\partial T}\right)_{n_a} \quad \text{eq. 21}$$

From Eq. 14 and 20, the respective components of the derivative are given by:

$$\left(\frac{\partial \theta}{\partial P}\right)_{n_a} = \left(\frac{\partial}{\partial P}\right)_{n_a} \left((1-\alpha)\left(\frac{K_1 P}{1+K_1 P}\right) + \alpha\left(\frac{K_2 P}{1+K_2 P}\right)\right)$$

$$= \left((1-\alpha)\left(\frac{K_1}{(1+K_1 P)^2}\right) + \alpha\left(\frac{K_2}{1+K_2 P}\right)\right)$$

$$= X^{-1}$$

$$\left(\frac{\partial \theta}{\partial K}\right)_{n_a} = \left(\frac{\partial}{\partial K}\right)_{n_a} \left((1-\alpha)\left(\frac{K_1 P}{1+K_1 P}\right) + \alpha\left(\frac{K_2 P}{1+K_2 P}\right)\right)$$

$$= \left((1-\alpha)\left(\frac{P}{(1+K_1 P)^2}\right) + \alpha\left(\frac{P}{(1+K_2 P)^2}\right)\right)$$

$$= Y$$

$$\left(\frac{\partial K_i}{\partial T}\right)_{n_a} = \left(\frac{\partial}{\partial T}\right)_{n_a} \left(\frac{A_i}{\sqrt{T}} e^{\frac{E_i}{RT}}\right) = -\frac{\frac{1}{2}RT + E_i}{RT^2} \frac{A_i}{\sqrt{T}} e^{\frac{E_i}{RT}}$$

$$\sum_i \left(\frac{\partial K_i}{\partial T}\right)_{n_a} = -\frac{\frac{1}{2}RT + E_1}{RT^2} K_1 - \frac{\frac{1}{2}RT + E_2}{RT^2} K_2 = -Z$$

These are combined to arrive at the isosteric enthalpy of adsorption, in Eq. 5-7:

$$-\left(\frac{\partial P}{\partial T}\right)_{n_a} = XYZ \quad \text{eq. 22}$$

The isosteric enthalpy of adsorption of methane on MSC-30 was determined using the most common approximations: the ideal gas law for the density in the gas phase, and the negligible molar volume of the adsorbed methane compared to the gas. The results are consistent with reported results for numerous sorbent systems and show a reasonable dependence of the isosteric enthalpy on both uptake and temperature. The Henry's law value is between 14.5-15.5 kJ mol$^{-1}$, consistent with the isoexcess results calculated without a fitting equation, and the enthalpy declines with uptake to 14 kJ mol$^{-1}$. Due to the ideal dependence of the gas density with pressure, the enthalpy reaches a plateau at high values of absolute uptake. This is a similar result as for hydrogen adsorption as well, since hydrogen is well approximated as an ideal gas in the typical ranges of temperature and pressure. However, methane is well known to deviate from ideality at conditions near ambient.

When the real gas data is used, the calculation of isosteric enthalpy changes significantly at high pressures (see FIGS. 11A and 11B). Non-ideality of methane in the gas phase is substantial under these conditions and must be taken into account for the most accurate description of adsorption thermodynamics. The tendency of the isosteric heat to a constant value at high uptake is commonly reported as evidence of proper calculation procedures; however this was not observed when ideal gas assumptions were omitted from the calculations in this example. It is suggested that a general exception be made for adsorption in the significantly non-ideal gas regime where there is no reason that the isosteric enthalpy of adsorption would persist to a plateau value.

Secondly, the change in molar volume on adsorption must also be carefully considered at high pressure, where the molar volume in the gas phase approaches that of liquid methane. The usual approximation, treating the adsorbed phase volume as negligible compared to that of the gas phase, holds in the low pressure limit, but becomes invalid beyond 1 MPa where the difference in isosteric heat calculated with or without the approximation is >1%, as shown in FIG. 12. To approximate the molar volume of the adsorbed phase, it is suggested to use that of liquid methane, a value that can be easily determined and which is seen as a reasonable approximation in numerous gas-solid adsorption systems. Specifically used was $v_a = v_{liq} = 38$ mL mol$^{-1}$, the value for pure methane at 111.5 K and 0.1 MPa, as shown in Eq. 5. In this case, the difference between the molar volume of the gas and the adsorbed phases becomes significant at all temperatures in this Example since $v_a$ is 5-30% the magnitude of $v_g$ at 10 MPa. The variation of the liquid molar volume with temperature and pressure was ~20% of that change, and so was considered to be a negligible complication within the error of the proposed assumption, and a fixed molar volume of the adsorbed phase was used throughout all temperatures and pressures.

In summary, the method used to determine the pressure dependence of the enthalpy of adsorption of methane on MSC-30 had a significant effect on the results. In every case utilizing the excess adsorption data, the enthalpy diverged at high uptake where the isoexcess assumption is not valid. A double-Langmuir-type equation derived from the definition of Gibbs surface excess was a satisfactory fitting equation in both the model-independent case, and also when used to determine the absolute quantity of adsorption in the isosteric analysis. In the latter case, the enthalpy of adsorption showed reasonable characteristics and conformed to our physical understanding of adsorption at all pressures and temperatures measured. It also gave a Henry's law value closest to that for a model-free analysis of the low pressure data. All simplifying approximations within the derivation of the isosteric enthalpy of adsorption were found to be extremely limited in validity for methane adsorption within the pressure and temperature range of study. Therefore, real gas equation of state data was used and a simple, effective approximation of the finite molar volume of the adsorbed phase was proposed.

Dependence of Optimized Parameters on Surface Area.

The optimized fit parameters from the double-Langmuir equation for all three materials were compared to their BET surface area as calculated from $N_2$ adsorption at 77 K. As expected, the scaling parameter $n_{max}$ showed a linear trend with BET surface area, in addition to the maximum adsorption volume $V_{max}$.

Dependence of Measured Uptake Capacity on Surface Area.

A rule of thumb for hydrogen storage in physisorbent materials is "Chahine's rule" which predicts 1 wt % Gibbs excess maximum uptake per 500 $m^2 g^{-1}$ of BET surface area at 77 K. A similar trend has been shown for methane uptake in physisorbent materials at 298 K, and the carbons in this Example are consistent with previous reports. The relationship for methane is 4.4 mmol $g^{-1}$ (6.6 wt %) Gibbs excess maximum uptake per 1000 $m^2 g^{-1}$ of BET surface area at 298 K.

Volumetric Storage Capacity.

Using the equilibrium excess uptake quantities and the bulk and skeletal densities of the materials studied, summarized in Table 1, the deliverable gravimetric capacity for each material can be determined for a model storage system. The bulk density values are not optimized by any means, and potential for improvement is highest for ZTC-3 (due to its extremely low bulk density) which proved to be the most difficult material to pack by simple means. The bulk densities are therefore a lower bound and are used for approximate comparison purposes only.

The gravimetric deliverable capacity of methane from a 70 L storage vessel weighing 77 kg is shown in FIG. 5 for all three materials compared to that from pure gas compression at 238 K. The deliverable amount is taken to be the difference between the amount in the tank at the pressure plotted and that at the "empty" pressure, which is a finite pressure determined by the desired application. For combustion, the empty pressure is expected to be low, but for delivery to a fuel cell, the gaseous fuel must be delivered at pressures above 0.3 MPa which is the value used in FIG. 5.

The increasing isosteric heat of adsorption on ZTC-3 in the range of pressure associated with methane delivery (>0.3 MPa) is seen to have a dramatic effect on the deliverable quantity stored in a fixed volume of a fixed system mass. If cycled between 0.3-9 MPa, the deliverable storage capacity of a 70 L tank containing ZTC-3 is 20% greater than that for pure compression, and 25% greater than that for a tank containing MSC-30. By improving the compaction of ZTC-3, this figure would increase. Cycling between 0.3-5 MPa, the improvement of a tank containing ZTC-3 over pure compression is 80%.

Data Tables.

The equilibrium methane adsorption data collected here represents one of the largest data sets of high pressure adsorption on carbon materials, and is of value for testing theoretical models of excess and absolute adsorption in the supercritical regime. The following are the experimentally collected isotherm data at all thirteen temperatures (for MSC-30 and ZTC-3) and six temperatures (for CNS-201).

All quantities of uptake are excess adsorption (in mmol $g^{-1}$) and pressure is given in MPa.

TABLE 4

Equilibrium excess uptake ($n_e$) of methane on CNS-201 between 0-9 MPa and 247-526 K.

| 247 K | | 255 K | | 273 K | | 298 K | | 340 K | | 526 K | |
|---|---|---|---|---|---|---|---|---|---|---|---|
| P | $n_e$ | P | $n_e$ | P | $n_e$ | P | $n_e$ | P | $n_e$ | P | $n_e$ |
| 0.03152 | 1.67257 | 0.04229 | 1.64637 | 0.05228 | 1.27878 | 0.06334 | 0.91254 | 0.07967 | 0.5274 | 0.097819 | 0.069506 |
| 0.07239 | 2.5821 | 0.08481 | 2.43702 | 0.10549 | 1.92069 | 0.13445 | 1.4835 | 0.16547 | 0.91903 | 0.19719 | 0.112226 |
| 0.13591 | 3.37671 | 0.15681 | 3.15692 | 0.16653 | 2.44753 | 0.1796 | 1.7654 | 0.19926 | 1.05814 | 0.226741 | 0.152351 |
| 0.36776 | 4.85045 | 0.38306 | 4.46709 | 0.39171 | 3.60815 | 0.40425 | 2.71515 | 0.42178 | 1.72127 | 0.452856 | 0.288719 |
| 0.34336 | 4.82206 | 0.35991 | 4.47964 | 0.38473 | 3.61107 | 0.43023 | 2.83989 | 0.45299 | 1.83435 | 0.501249 | 0.277787 |
| 0.65027 | 5.67962 | 0.65664 | 5.26539 | 0.66169 | 4.38914 | 0.67356 | 3.41782 | 0.67962 | 2.2663 | 0.708568 | 0.430165 |
| 0.93424 | 6.16763 | 0.93808 | 5.76141 | 0.93794 | 4.89898 | 0.94514 | 3.89866 | 0.95054 | 2.69296 | 0.97468 | 0.563666 |
| 1.30435 | 6.56888 | 0.95561 | 5.92503 | 1.30697 | 5.34975 | 0.98043 | 4.03178 | 0.99905 | 2.81603 | 1.05145 | 0.551184 |
| 0.92459 | 6.26662 | 2.00844 | 6.83832 | 0.95148 | 4.97657 | 1.31377 | 4.36175 | 1.31544 | 3.12939 | 1.338117 | 0.719586 |
| 2.05602 | 7.17087 | 3.37154 | 7.23226 | 1.70387 | 5.6841 | 1.71307 | 4.71663 | 1.70861 | 3.48582 | 1.730618 | 0.867242 |
| 3.37154 | 7.4546 | 4.83805 | 7.23898 | 2.07256 | 6.00209 | 2.09945 | 5.09704 | 2.10884 | 3.77314 | 2.126852 | 1.004889 |
| 4.72222 | 7.44093 | 6.1453 | 7.0695 | 3.38808 | 6.41418 | 3.44393 | 5.67153 | 2.10566 | 3.81896 | 2.160127 | 1.019048 |
| 6.09772 | 7.19462 | 7.4753 | 6.83372 | 4.78841 | 6.60544 | 4.81323 | 5.91865 | 2.61693 | 4.0482 | 2.623078 | 1.175894 |
| 7.45047 | 6.80867 | 8.79495 | 6.52202 | 6.14323 | 6.55984 | 6.16598 | 5.98388 | 3.14155 | 4.27859 | 3.149701 | 1.334875 |
| 8.86735 | 6.32538 | | | 7.52701 | 6.43028 | 7.58596 | 5.92181 | 3.42325 | 4.47431 | 3.448758 | 1.390724 |
| | | | | 8.88803 | 6.23452 | 8.98008 | 5.85881 | 4.80909 | 4.81467 | 4.840809 | 1.719674 |
| | | | | | | | | 6.17219 | 5.06671 | 6.191492 | 1.972601 |
| | | | | | | | | 7.56631 | 5.12316 | 7.544243 | 2.147271 |
| | | | | | | | | 8.99352 | 5.16602 | 8.923884 | 2.320326 |

TABLE 5

Equilibrium excess uptake ($n_e$) of methane on MSC-30 between 0-9 MPa and 238-521 K. Excess uptake is in units of mmol $g^{-1}$, and pressure is in MPa.

| 238 K | | 247 K | | 255 K | | 264 K | | 274 K | |
|---|---|---|---|---|---|---|---|---|---|
| P | $n_e$ | P | $n_e$ | P | $n_e$ | P | $n_e$ | P | $n_e$ |
| 0.05833 | 2.9238 | 0.06403 | 2.45831 | 0.06851 | 2.11609 | 0.07259 | 1.78676 | 0.07857 | 1.53347 |
| 0.11997 | 4.69747 | 0.13031 | 4.10954 | 0.13858 | 3.6424 | 0.14893 | 3.16232 | 0.15306 | 2.57795 |
| 0.16659 | 5.99416 | 0.17429 | 5.02072 | 0.18157 | 4.34218 | 0.19018 | 3.7357 | 0.19962 | 3.20815 |
| 0.38337 | 9.58601 | 0.39147 | 8.2111 | 0.40169 | 7.2246 | 0.40603 | 6.23223 | 0.41481 | 5.37494 |

TABLE 5-continued

Equilibrium excess uptake ($n_e$) of methane on MSC-30 between 0-9 MPa and 238-521 K. Excess uptake is in units of mmol g$^{-1}$, and pressure is in MPa.

| 0.38886 | 9.60792 | 0.40127 | 8.44362 | 0.41162 | 7.38545 | 0.42403 | 6.45678 | 0.42816 | 5.57936 |
|---|---|---|---|---|---|---|---|---|---|
| 0.64855 | 12.1436 | 0.65332 | 10.6203 | 0.6606 | 9.45941 | 0.66548 | 8.29874 | 0.67052 | 7.241 |
| 0.92612 | 13.9381 | 0.92823 | 12.3509 | 0.94684 | 11.1896 | 0.93906 | 9.90769 | 0.93956 | 8.71834 |
| 1.29423 | 15.5909 | 1.2942 | 13.9885 | 1.30041 | 12.7407 | 1.30609 | 11.5053 | 1.31153 | 10.254 |
| 0.93286 | 14.1493 | 0.94734 | 12.7338 | 0.94734 | 11.3984 | 0.96389 | 10.2582 | 0.95975 | 8.96193 |
| 1.68779 | 16.9261 | 1.6907 | 15.3031 | 1.69771 | 14.0657 | 1.69753 | 12.7683 | 1.6995 | 11.4799 |
| 2.02292 | 18.2268 | 2.03533 | 16.5959 | 2.03533 | 15.1829 | 2.05188 | 13.9954 | 2.04981 | 12.6185 |
| 3.31569 | 20.6412 | 3.3343 | 18.8821 | 3.33637 | 17.6298 | 3.34672 | 16.3614 | 3.35292 | 14.8886 |
| 4.6643 | 21.6807 | 4.68499 | 19.9797 | 4.69947 | 18.9025 | 4.70153 | 17.8168 | 4.71188 | 16.1946 |
| 6.0274 | 21.6092 | 6.05842 | 20.1924 | 6.0667 | 19.4372 | 6.08738 | 18.4286 | 6.106 | 16.9328 |
| 7.39049 | 20.4545 | 7.41945 | 19.8207 | 7.44427 | 19.2498 | 7.50012 | 18.4075 | 7.47943 | 17.1863 |
| 8.76599 | 18.7465 | 8.78875 | 18.8379 | 8.77634 | 18.6868 | 8.85287 | 17.978 | 8.8508 | 16.9893 |

| 283 K | | 298 K | | 320 K | | 340 K | | 362 K | |
|---|---|---|---|---|---|---|---|---|---|
| P | $n_e$ | P | $n_e$ | P | $n_e$ | P | $n_e$ | P | $n_e$ |
| 0.08102 | 1.26426 | 0.08583 | 0.99576 | 0.08681 | 0.72106 | 0.09239 | 0.54439 | 0.094979 | 0.430147 |
| 0.16547 | 2.36311 | 0.17582 | 1.90399 | 0.1903 | 1.50583 | 0.19857 | 1.06281 | 0.196501 | 0.875872 |
| 0.20274 | 2.70332 | 0.20382 | 2.0854 | 0.20706 | 1.55225 | 0.21438 | 1.19026 | 0.214036 | 0.909031 |
| 0.33033 | 3.89333 | 0.42207 | 3.66646 | 0.43104 | 2.82131 | 0.4361 | 2.20365 | 0.439484 | 1.723959 |
| 0.44471 | 4.95187 | 0.45712 | 4.06506 | 0.48194 | 3.14552 | 0.49022 | 2.38996 | 0.490217 | 1.849482 |
| 0.47045 | 4.99361 | 0.67952 | 5.12491 | 0.68889 | 4.01374 | 0.69328 | 3.19194 | 0.697329 | 2.53159 |
| 0.69177 | 6.40959 | 0.94723 | 6.33031 | 0.95273 | 5.02437 | 0.95659 | 4.06614 | 0.960241 | 3.260971 |
| 0.94548 | 7.68997 | 0.99698 | 6.66047 | 1.32764 | 6.212 | 1.31962 | 5.08994 | 1.322611 | 4.131244 |
| 0.9825 | 8.07819 | 1.32053 | 7.66942 | 1.01973 | 5.36591 | 1.03421 | 4.22971 | 1.034214 | 3.515799 |
| 1.30932 | 9.12433 | 1.70637 | 8.76495 | 1.70974 | 7.21361 | 1.71626 | 6.02772 | 1.715512 | 4.943074 |
| 1.70035 | 10.3131 | 2.08497 | 9.83784 | 2.10773 | 8.19921 | 2.12221 | 6.78673 | 2.128412 | 5.737387 |
| 2.06739 | 11.4622 | 3.37981 | 12.0743 | 3.40256 | 10.3124 | 3.42532 | 8.76072 | 3.410836 | 7.611534 |
| 3.36533 | 13.7431 | 4.74084 | 13.3635 | 4.77186 | 11.6409 | 4.78014 | 10.1134 | 4.765656 | 8.982563 |
| 4.72842 | 15.0664 | 6.11634 | 14.1824 | 6.14323 | 12.5508 | 6.14943 | 11.1424 | 6.145297 | 10.07682 |
| 6.11634 | 15.7619 | 7.49598 | 14.4775 | 7.52494 | 13.2593 | 7.52494 | 11.8791 | 7.518733 | 10.61905 |
| 7.48564 | 16.0976 | 8.91492 | 14.4206 | 8.8901 | 13.6037 | 8.91078 | 12.2573 | 8.867347 | 11.06398 |
| 8.85287 | 15.9519 | | | | | | | | |

| 402 K | | 450 K | | 521 K | |
|---|---|---|---|---|---|
| P | $n_e$ | P | $n_e$ | P | $n_e$ |
| 0.095312 | 0.264322 | 0.206843 | 0.312932 | 0.100032 | 0.096919 |
| 0.21098 | 0.516237 | 0.504696 | 0.802983 | 0.208911 | 0.257445 |
| 0.219435 | 0.577949 | 1.056966 | 1.547822 | 0.223222 | 0.202398 |
| 0.44715 | 1.100658 | 2.161506 | 2.802391 | 0.457736 | 0.419764 |
| 0.500559 | 1.168727 | 3.456342 | 4.001805 | 0.506765 | 0.563646 |
| 0.707795 | 1.645824 | 4.811162 | 4.905019 | 0.710382 | 0.622786 |
| 0.966574 | 2.132081 | 6.199076 | 5.49889 | 0.97396 | 0.810212 |
| 1.328544 | 2.775085 | 7.599401 | 6.312641 | 1.345529 | 1.092771 |
| 1.048693 | 2.319473 | 8.962495 | 6.740001 | 1.06524 | 1.107253 |
| 1.716512 | 3.365324 | | | 1.732164 | 1.375554 |
| 2.142891 | 3.947574 | | | 2.175985 | 1.892646 |
| 3.435658 | 5.410322 | | | 3.468752 | 2.647447 |
| 4.804956 | 6.461805 | | | 4.827709 | 3.077738 |
| 6.170118 | 7.287202 | | | 6.188734 | 3.767925 |
| 7.560101 | 7.917329 | | | 7.589059 | 4.672123 |
| 8.925263 | 8.275128 | | | 8.958358 | 5.060649 |

TABLE 6

Equilibrium excess uptake ($n_e$) of methane on ZTC-3 between 0-9 MPa and 238-518 K.

| 238 K | | 247 K | | 255 K | | 265 K | | 273 K | |
|---|---|---|---|---|---|---|---|---|---|
| P | $n_e$ | P | $n_e$ | P | $n_e$ | P | $n_e$ | P | $n_e$ |
| 0.08851 | 2.74035 | 0.08679 | 2.13278 | 0.08785 | 1.7617 | 0.08958 | 1.3912 | 0.09042 | 1.19214 |
| 0.16961 | 4.59656 | 0.17168 | 3.77235 | 0.18202 | 3.26497 | 0.18616 | 2.77652 | 0.18823 | 2.0028 |
| 0.2029 | 5.27133 | 0.20612 | 4.2689 | 0.20957 | 3.63528 | 0.21157 | 2.90978 | 0.21121 | 2.51615 |
| 0.42155 | 8.91232 | 0.4269 | 7.35128 | 0.43062 | 6.29889 | 0.43635 | 5.16111 | 0.43412 | 4.5226 |
| 0.45092 | 9.40485 | 0.45505 | 7.93782 | 0.46333 | 6.73821 | 0.46953 | 5.71611 | 0.47574 | 4.58662 |
| 0.6774 | 11.9303 | 0.68328 | 9.99992 | 0.68526 | 8.70216 | 0.6898 | 7.23912 | 0.69237 | 6.41887 |
| 0.94884 | 14.2414 | 0.95019 | 12.0991 | 0.95218 | 10.6767 | 0.95497 | 8.99989 | 0.95595 | 8.03245 |
| 1.32374 | 16.4732 | 1.31149 | 14.1354 | 1.31361 | 12.7497 | 1.31735 | 10.9502 | 1.31765 | 9.80274 |
| 0.99078 | 14.992 | 0.97837 | 12.7874 | 1.00319 | 11.2714 | 1.0156 | 9.66277 | 1.01767 | 8.04942 |

TABLE 6-continued

Equilibrium excess uptake ($n_e$) of methane on ZTC-3 between 0-9 MPa and 238-518 K.

| | | | | | | | | | |
|---|---|---|---|---|---|---|---|---|---|
| 1.70425 | 18.0077 | 1.71079 | 15.7958 | 1.70465 | 14.3496 | 1.70998 | 12.5064 | 1.70749 | 11.3014 |
| 2.06843 | 19.806 | 2.06843 | 17.5107 | 2.08291 | 15.9724 | 2.13255 | 14.2609 | 2.10359 | 12.1293 |
| 3.34465 | 21.9819 | 3.35499 | 19.719 | 3.35085 | 18.615 | 3.42945 | 16.8004 | 3.43359 | 14.7722 |
| 4.68085 | 22.1343 | 4.69533 | 20.5004 | 4.70153 | 19.7399 | 4.7429 | 17.9216 | 4.74704 | 16.2179 |
| 6.04188 | 21.4464 | 6.05015 | 20.2592 | 6.06877 | 20.2461 | 6.09359 | 18.5297 | 6.10393 | 16.9999 |
| 7.37394 | 19.9073 | 7.4029 | 19.6406 | 7.41945 | 19.7629 | 7.45668 | 18.1864 | 7.4753 | 16.9993 |
| 8.70394 | 18.2061 | 8.74945 | 18.8376 | 8.78461 | 18.8635 | 8.81977 | 17.7636 | 8.83218 | 16.6217 |

| 284 K | | 298 K | | 321 K | | 339 K | | 358 K | |
|---|---|---|---|---|---|---|---|---|---|
| P | $n_e$ | P | $n_e$ | P | $n_e$ | P | $n_e$ | P | $n_e$ |
| 0.09123 | 0.88433 | 0.093912 | 0.767091 | 0.0953 | 0.54893 | 0.10247 | 0.43382 | 0.096459 | 0.323046 |
| 0.1965 | 2.06013 | 0.198569 | 1.525807 | 0.20271 | 1.18196 | 0.20684 | 0.88951 | 0.21098 | 0.78299 |
| 0.21736 | 2.00538 | 0.216702 | 1.623577 | 0.21582 | 1.15255 | 0.22593 | 0.92303 | 0.218849 | 0.698188 |
| 0.44294 | 3.68469 | 0.441884 | 2.959302 | 0.4386 | 2.14771 | 0.44498 | 1.72043 | 0.445363 | 1.315477 |
| 0.50056 | 4.35259 | 0.494354 | 3.082729 | 0.49642 | 2.38748 | 0.52331 | 1.91015 | 0.506765 | 1.647565 |
| 0.69745 | 5.27895 | 0.696663 | 4.262035 | 0.69725 | 3.17345 | 0.69882 | 2.54586 | 0.700142 | 1.953702 |
| 0.96076 | 6.70279 | 0.961174 | 5.421924 | 0.96203 | 4.09233 | 0.9732 | 3.35164 | 0.97132 | 2.576551 |
| 1.04042 | 7.4082 | 1.036282 | 5.813822 | 1.0549 | 4.28315 | 1.05697 | 3.56373 | 1.054898 | 2.89235 |
| 1.32366 | 8.28589 | 1.323678 | 6.789015 | 1.32066 | 5.19525 | 1.32517 | 4.27993 | 1.33449 | 3.339732 |
| 1.72003 | 9.6975 | 1.713379 | 7.996622 | 1.71103 | 6.26021 | 1.71527 | 5.17057 | 1.721525 | 4.032177 |
| 2.12014 | 11.1833 | 2.126343 | 9.241572 | 2.10913 | 7.19584 | 2.11204 | 5.97504 | 2.116959 | 4.708681 |
| 3.40463 | 13.8392 | 3.412905 | 11.66409 | 2.12841 | 7.11606 | 2.14496 | 6.00636 | 2.153233 | 4.899497 |
| 4.75531 | 15.3532 | 4.753246 | 12.94425 | 2.60936 | 8.20323 | 2.61 | 6.90677 | 2.614118 | 5.477988 |
| 6.12875 | 16.0017 | 6.124613 | 13.83233 | 3.13225 | 9.16678 | 3.14116 | 7.77021 | 3.143808 | 6.124452 |
| 7.53114 | 16.1515 | 7.506322 | 14.0912 | 3.4129 | 9.30043 | 3.43359 | 8.0335 | 3.441863 | 6.760846 |
| 8.88389 | 15.6163 | 8.869416 | 13.75196 | 4.73877 | 10.8634 | 4.78634 | 9.4703 | 4.794614 | 7.933946 |
| 0.09123 | 0.88433 | 0.093912 | 0.767091 | 6.11427 | 11.9473 | 6.15771 | 10.5049 | 6.159776 | 9.011308 |
| | | | | 7.55803 | 12.6389 | 7.51873 | 11.2003 | 7.529075 | 9.661693 |
| | | | | 8.89631 | 12.9869 | 8.98525 | 11.7674 | 8.914921 | 9.868008 |

| 396 K | | 439 K | | 518 K | |
|---|---|---|---|---|---|
| P | $n_e$ | P | $n_e$ | P | $n_e$ |
| 0.098045 | 0.220005 | 0.100858 | 0.120166 | 0.102765 | 0.079153 |
| 0.221102 | 0.467406 | 0.223382 | 0.27326 | 0.22339 | 0.061015 |
| 0.22339 | 0.461032 | 0.235801 | 0.281368 | 0.225827 | 0.164918 |
| 0.450016 | 0.903976 | 0.455363 | 0.547338 | 0.454869 | 0.336001 |
| 0.523312 | 0.943054 | 0.533654 | 0.709964 | 0.531586 | 0.291516 |
| 0.705995 | 1.367028 | 0.713208 | 0.829307 | 0.711581 | 0.530536 |
| 0.998505 | 1.849129 | 0.979053 | 1.119917 | 0.977226 | 0.727606 |
| 1.075582 | 1.916965 | 1.100403 | 1.398448 | 1.094198 | 0.657902 |
| 1.341676 | 2.362146 | 1.340223 | 1.504728 | 1.342663 | 0.953889 |
| 1.726711 | 2.926605 | 1.730591 | 1.875245 | 1.733964 | 1.207439 |
| 2.122545 | 3.443224 | 2.126825 | 2.263501 | 2.15193 | 1.415868 |
| 2.186328 | 3.473505 | 2.20908 | 2.44604 | 2.211149 | 1.343479 |
| 2.623971 | 4.042535 | 2.63105 | 2.705292 | 2.63669 | 1.697484 |
| 3.152194 | 4.616633 | 3.154074 | 3.219059 | 3.232508 | 2.017694 |
| 3.470821 | 4.831019 | 4.19477 | 3.866671 | 3.503916 | 2.077024 |
| 4.815298 | 6.115046 | 5.082126 | 4.5686 | 4.893899 | 2.84219 |
| 6.186666 | 7.102554 | 6.283882 | 5.230203 | 6.306634 | 3.552917 |
| 7.591128 | 7.807846 | 7.61388 | 5.890184 | 7.665591 | 4.243635 |
| 8.943879 | 8.214734 | 9.024548 | 6.265714 | 9.086601 | 4.682551 |

REFERENCES

US Patent Application Publication Nos. 2002/0023539, 2008/0207442, 2009/0273106, 2011/0048063, 2011/0052486, 2011/0092362, 2011/0240491.

U.S. Pat. Nos. 4,716,736, 4,752,310, 4,881,376, 5,171,333, 5,626,637, 7,250,074, 8,192,709.

J. Alcañiz-Monge, D. Lozano-Castelló, D. Cazorla-Amorós, and A. Linares-Solano, 'Fundamentals of methane adsorption in microporous carbons', *Microporous Mesoporous Mater.*, 124, 110-16 (2009).

Al-Muhtaseb, S. A.; Ritter, J. A. *J. Phys. Chem. B* 1999, 103, 2467-79.

G. L. Aranovich and M. D. Donohue, 'Adsorption isotherms for microporous adsorbents', *Carbon*, 33, 1369-75 (1995).

G. Aranovich and M. Donohue, 'Determining surface areas from linear adsorption isotherms at supercritical conditions', *J. Colloid Interface Sci.*, 194, 392-97 (1997).

Bénard, P.; Chahine, R. *Langmuir* 2001, 17, 1950-55.

Bhatia, S. K.; Myers, A. L. *Langmuir* 2006, 22, 1688-700.

A. Chakraborty, B. B. Saha, S. Koyama, K. C. Ng, and S.-H. Yoon, 'Thermodynamic trends in the uptake capacity of porous adsorbents on methane and hydrogen', *Appl. Phys. Lett.*, 92, 201911-3 (2008).

Chung, T. C. M.; Jeong, Y.; Chen, Q.; Kleinhammes, A.; Wu, Y. *J. Am. Chem. Soc.* 2008, 130, 6668-69.

Cracknell, R. F.; Gordon, P.; Gubbins, K. E. *J. Phys. Chem.* 1993, 97, 494-99.

J. B. Dumas, 'A method of estimating nitrogen in organic material', *Ann. Chim. et Phys.*, 58, 171 (1833).

Jin, Z.; Lu, W.; O'Neill, K. J.; Parilla, P. A.; Simpson, L. J.; Kittrell, C.; Tour, J. M. *Chem. Mater.* 2011, 23, 923-25.

Jin, Z.; Sun, Z. Z.; Simpson, L. J.; O'Neill, K. J.; Parilla, P. A.; Li, Y.; Stadie, N. P.; Ahn, C. C.; Kittrell, C.; Tour, J. M. *J. Am. Chem. Soc.* 2010, 132, 15246-51.

C. Kittel, *Thermal physics*, John Wiley, New York (1969).

T. Kiyobayashi, H. T. Takeshita, H. Tanaka, N. Takeichi, A. Züttel, L. Schlapbach, and N. Kuriyama, 'Hydrogen adsorption in carbonaceous materials—how to determine the storage capacity accurately', *J. Alloys Compd.*, 330-332, 666-69 (2002).

E. W. Lemmon, M. L. Huber, and M. O. McLinden, 'NIST standard reference database 23: reference fluid thermodynamic and transport properties—REFPROP', Number Version 8.0 in Standard Reference Data Program (2007).

Li et al., *Scientific Reports* 3, 2420 (2013).

Lozano-Castello, D.; Cazorla-Amoros, D.; Linares-Solano, A.; Quinn, D. F. *Carbon* 2002, 40, 989-1002.

K. R. Matranga, A. L. Myers, and E. D. Glandt, 'Storage of natural gas by adsorption on activated carbon', *Chem. Eng. Sci.*, 47, 1569-79 (1992).

T. P. McNicholas, A. Wang, K. O'Neill, R. J. Anderson, N. P. Stadie, A. Kleinhammes, P. Parilla, L. Simpson, C. C. Ahn, Y. Wang, Y. Wu, and J. Liu, 'H2 storage in microporous carbons from PEEK precursors', *J. Phys. Chem. C*, 114, 13902-08 (2010).

F. O. Mertens, 'Determination of absolute adsorption in highly ordered porous media', *Surf. Sci.*, 603, 1979-84 (2009).

A. L. Myers, J. A. Calles, and G. Calleja, 'Comparison of molecular simulation of adsorption with experiment', *Adsorption*, 3, 107-15 (1997).

D. Nicholson, 'Simulation studies of methane transport in model graphite micropores', *Carbon*, 36, 1511-23 (1998).

H. Nishihara, P. X. Hou, L. X. Li, M. Ito, M. Uchiyama, T. Kaburagi, A. Ikura, J. Katamura, T. Kawarada, K. Mizuuchi, and T. Kyotani, 'High-pressure hydrogen storage in zeolite-templated carbon', *J. Phys. Chem. C*, 113, 3189-96 (2009).

Nishihara, H.; Kyotani, T. *Adv. Mater.* 2012, 24, 4473-98.

R. J. Olsen, 'Investigations of novel hydrogen adsorption phenomena', thesis, University of Missouri (2011).

S. Ono and S. Kondo, Molecular theory of surface tension in liquids, Springer-Verlag, Berlin (1960).

Panella, B.; Hirscher, M.; Roth, S. *Carbon* 2005, 43, 2209-14.

E. Poirier, R. Chahine, and T. K. Bose, 'Hydrogen adsorption in carbon nanostructures', *Int. J. Hydrogen Energ.*, 26, 831-35 (2001).

J. J. Purewal, H. Kabbour, J. J. Vajo, C. C. Ahn, and B. Fultz, 'Pore size distribution and supercritical hydrogen adsorption in activated carbon fibers', *Nanotechnology*, 20, 204012 (2009).

J. Purewal, D. Liu, A. Sudik, M. Veenstra, J. Yang, S. Maurer, U. Müller, and D. J. Siegel, 'Improved hydrogen storage and thermal conductivity in high-density MOF-5 composites', *J. Phys. Chem. C*, 116, 20199-212 (2012).

Rouquerol, F.; Rouquerol, J.; Sing, K. S. W. Adsorption by powders and porous solids: principles, methodology, and applications; Academic Press: San Diego, 1999.

D. Saha, Z. Wei, and S. Deng, 'Equilibrium, kinetics, and enthalpy of hydrogen adsorption in MOF-177', *Int. J. Hydrogen Energy*, 33, 7479-88 (2008).

Salem, M. M. K.; Braeuer, P.; Szombathely, M.; Heuchel, M.; Harting, P.; Quitzsch, K.; Jaroniec, M. *Langmuir* 1998, 14, 3376-89.

Sillar, K.; Sauer, J. *J. Am. Chem. Soc.* 2012, doi: 10.1021/ja307076t.

S. Sircar, 'Gibbsian surface excess for gas adsorption—revisited', *Ind. Eng. Chem. Res.*, 38, 3670-82 (1999).

Sircar, S.; Mohr, R.; Ristic, C.; Rao, M. B. *J. Phys. Chem. B* 1999, 103, 6539-46.

N. P. Stadie, 'Synthesis and thermodynamic studies of physisorptive energy storage materials', Ph.D. thesis, California Institute of Technology (2012).

N. P. Stadie, J. J. Purewal, C. C. Ahn, and B. Fultz, 'Measurements of hydrogen spillover in platinum doped superactivated carbon', *Langmuir*, 26, 15481-85 (2010).

N. P. Stadie, J. J. Vajo, R. W. Cumberland, A. A. Wilson, C. C. Ahn, and B. Fultz, 'Zeolite-templated carbon materials for high-pressure hydrogen storage', *Langmuir*, 28, 10057-63 (2012).

Y. Sun, C. Liu, W. Su, Y. Zhou, and L. Zhou, 'Principles of methane adsorption and natural gas storage', *Adsorption*, 15, 133-37 (2009).

P. Tarazona, U. M. B. Marconi, and R. Evans, 'Phase equilibria of fluid interfaces and confined fluids', *Mol. Phys.*, 60, 573-95 (1987).

Terrones et al., Phys. Rev. B., 55:15, 9969-9974 (1997).

T. Voskuilen, T. Pourpoint, and A. Dailly, 'Hydrogen adsorption on microporous materials at ambient temperatures and pressures up to 50 MPa', *Adsorption*, 18, 239-49 (2012).

Xia, Y.; Walker, G. S.; Grant, D. M.; Mokaya, R. *J. Am. Chem. Soc.* 2009, 131, 16493-99.

Xia et al., *Scientific Reports* 3, 1935 (2013).

Z. Yang, Y. Xia, and R. Mokaya, 'Enhanced hydrogen storage capacity of high surface area zeolite-like carbon materials', *J. Am. Chem. Soc.*, 129, 1673-79 (2007).

Zhou, Y.; Zhou, L. *Langmuir* 2009, 25, 13461-66.

Example 3

Pore Structure Geometries for Confinement in One or More Dimension

In some aspects, the invention provides a materials-level approach to engineering and using porous adsorbents to achieve efficient and reversible uptake for a range of industrial processes including energy storage and delivery. Design and selection of adsorbents having pore structures with physical dimensions, shapes and/or ordering that confines adsorbed species in one or more spatial dimensions is useful in some embodiments to achieve enhanced uptake and release properties relative to conventional adsorbents. For example, materials having a network of pores structures with nanoscale lengths, diameters and/or widths in one, two or three spatial dimensions is useful in some embodiments to achieve energetic and/or thermodynamic properties resulting in enhanced reversible uptake of compressed gases. A wide range of pore geometries are useful for providing such confinement along one or more physical dimensions including, slits, channels, cages, grooves, passages, cavities, cylinders, boxes, chambers, perforated structures, etc.

Experimental studies demonstrate that ZTC enhances methane-methane interactions due to its proper pore size (around 11-12 angstroms). This result indicates that there is a beneficial interaction between molecules confined on either side of the pore that should not be present for graphene. Accordingly, engineering the pore structure of adsorbent materials so as to confine the adsorbed molecules at the proper distance for more than one spatial dimension provides a means to achieve greater enhancement of interactions and, thus more efficient reversible uptake.

Figure 17A:
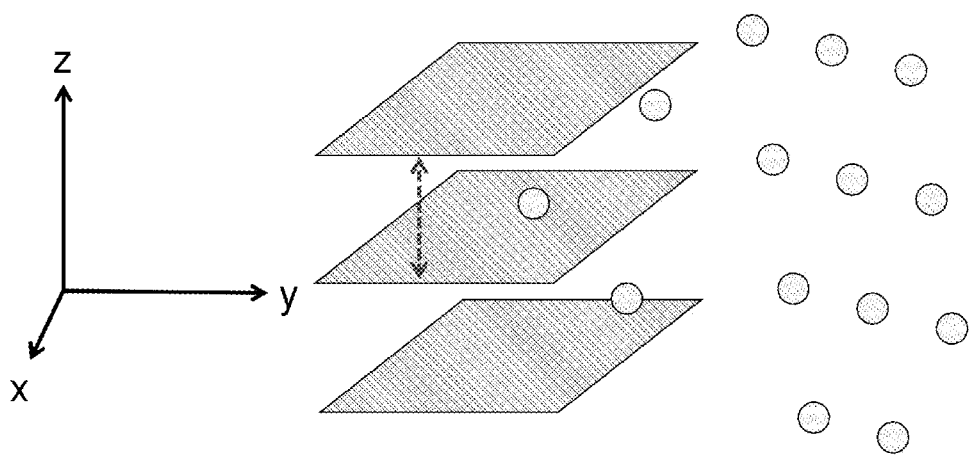
FIGS. 17A-17C provides a series of schematic diagrams illustrating confinement of an adsorbed species, such as methane, in one or more spatial dimensions within a pore structure of a porous adsorbent.
Figure 17B:
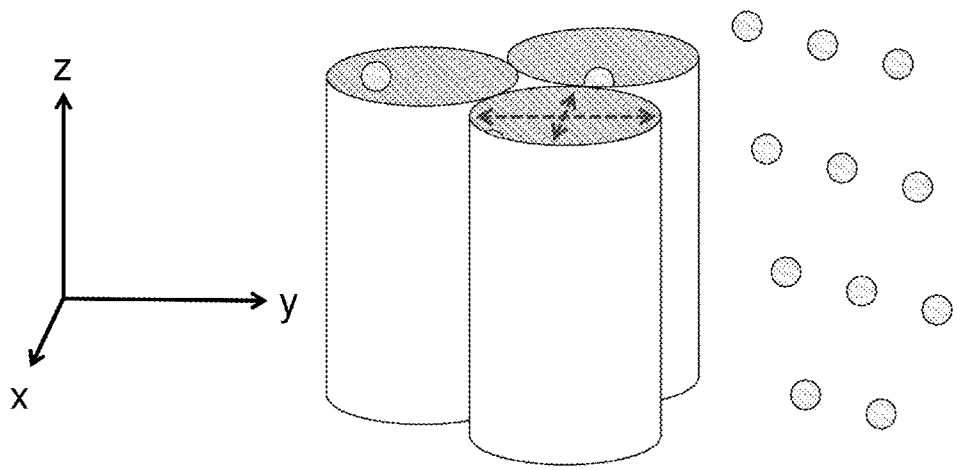
Figure 17C:
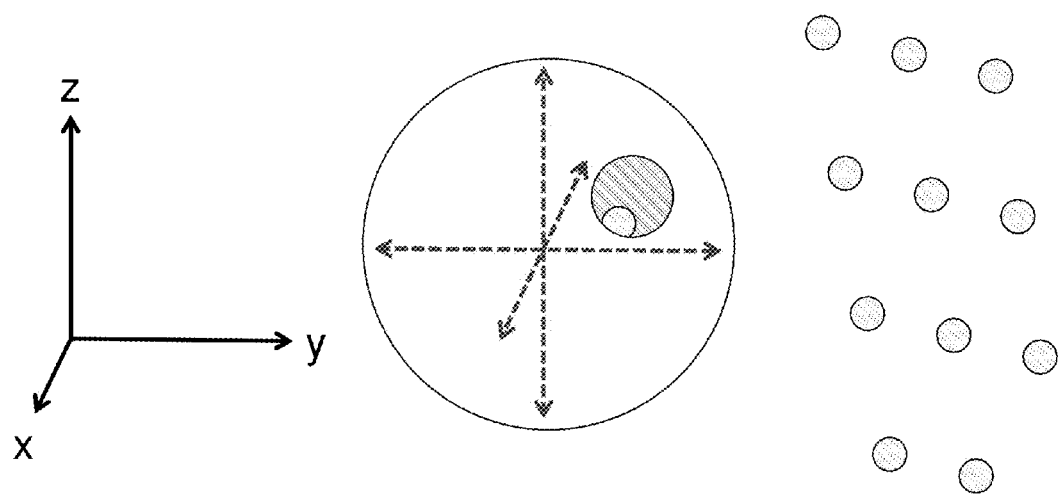

As an example of this engineering concept, FIGS. 17A-17C provide a series of schematic diagrams illustrating confinement of an adsorbed species, such as methane, along one or more spatial dimensions within a pore structure of a porous adsorbent.

FIG. 17A provides a schematic showing an adsorbed species on the surface of an adsorbent, "confined" in one dimension (z), as indicated by the arrow. The adsorbed species, is still free to move along the surface in two dimensions, and is in equilibrium with the gas phase which exists in three spatial dimensions. FIG. 17B provides a schematic showing an adsorbed species on the surface of an adsorbent, "confined" in two dimensions (x and y), as indicated by the arrows. The adsorbed species is free to sample adsorption sites along one dimension and is in equilibrium with the gas in three dimensions. FIG. 17C provides a schematic showing an adsorbed species on the surface of an adsorbent, such as a perforated spherical shaped adsorbent, where the adsorbed species is "confined" in three dimensions, as indicated by the arrows. The adsorbed species is in equilibrium with the gas phase in three dimensions.

Examples of pore geometries such as grooves, cavities, channels, boxes, cages, and perforations are capable of confinement in one, two, or three dimensions, with unlimited combinatorial varieties.

In some embodiments, for example, a porous adsorbent has pores characterized by a channel type geometry. Some embodiments of channel-type porous structures are characterized by square, circular or hexagonal cross sectional geometries and confine adsorbed species in two dimensions, though the adsorbed species are still free to move along the length of the channel.

In some embodiments a porous adsorbent has pores that incorporate a cage-like pore geometry, where the dimensional distances are optimized with respect to the adsorbed species. Some embodiments of cage-type pore networks are characterized by spherical, cube, or other 3D polygonal structures that confine the adsorbed species in three spatial dimensions. In a specific embodiment optimized for methane, the cage geometry of the pore structure is characterized by spatial dimensions of 12×12×12 Angstroms.

Figure 17D:
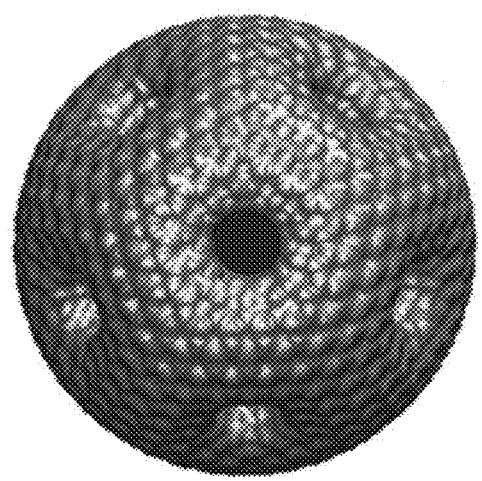
FIG. 17D provides a depiction of a perforated fullerene.

In conjunction with FIG. 17C, FIG. 17D shows a perforated fullerene pore geometry, an example of an adsorbent providing confinement in three spatial dimensions. Various perforated fullerenes are described in Terrones et al., Phys. Rev. B., 55:15, 9969-9974 (1997), which is hereby incorporated by reference.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups and classes that can be formed using the substituents are disclosed separately. When a Markush group or other grouping is used herein, all individual members of the group and all combinations and subcombinations possible of the group are intended to be individually included in the disclosure. As used herein, "and/or" means that one, all, or any combination of items in a list separated by "and/or" are included in the list; for example "1, 2 and/or 3" is equivalent to "'1' or '2' or '3' or '1 and 2' or '1 and 3' or '2 and 3' or '1, 2 and 3'".

Every formulation or combination of components described or exemplified can be used to practice the invention, unless otherwise stated. Specific names of materials are intended to be exemplary, as it is known that one of ordinary skill in the art can name the same material differently. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method for storing a gas on a porous adsorbent, the method comprising the steps of:

selecting said porous adsorbent having a first chemical composition;

determining a first pore size distribution for the porous adsorbent having the first chemical composition, wherein the first pore size distribution provides a constant or increasing isosteric enthalpy of adsorption as a function of uptake of the gas on an exposed surface of the porous adsorbent;

providing the porous adsorbent having a first plurality of ordered pore structures characterized by the first pore size distribution; and contacting the porous adsorbent with the gas at a pressure sufficient to achieve adsorption of the gas on the porous adsorbent characterized by the constant or increasing isosteric enthalpy of adsorption as a function of uptake of the gas, thereby storing the gas on the porous adsorbent.

2. The method of claim 1, wherein the first pore size distribution provides the isosteric enthalpy of adsorption that increases as a function of uptake of the gas by at least 0.01 kJ mol$^{-1}$/mmol g$^{-1}$.

3. The method of claim 1, wherein the step of determining the first pore size distribution comprises steps of:

providing the porous adsorbent;

contacting the porous adsorbent with the gas at a pressure sufficient to achieve adsorption of the gas onto the exposed surface of the porous adsorbent; and measuring the isosteric enthalpy of adsorption of the gas as a function of uptake of the gas by the porous adsorbent to establish that the first pore size distribution provides the constant or increasing isosteric enthalpy of adsorption as a function of uptake of the gas on the exposed surface of the porous adsorbent.

4. The method of claim 3, further comprising a step of determining a slope of the isosteric enthalpy of adsorption of the gas as a function of uptake of the gas by the porous adsorbent or further comprising a step of computing an isosteric enthalpy of adsorption of the gas as a function of uptake of the gas by the porous adsorbent by fitting or regression analysis of gas uptake data or further comprising a step of generating a plot of the isosteric enthalpy of adsorption of the gas as a function of uptake of the gas by the porous adsorbent.

5. The method of claim 3, wherein the step of measuring the isosteric enthalpy of adsorption comprises measuring a plurality of gas adsorption isotherms for a plurality of selected temperatures or comprises steps of adsorbing a known uptake amount of the gas on the exposed surface of the adsorbent material and measuring a heat quantity released by the known uptake amount of the gas upon adsorption or comprises measuring a temperature change of the porous adsorbent upon adsorption of a known uptake amount of the gas.

6. The method of claim 5, wherein each gas adsorption isotherm is measured by exposing the porous adsorbent to a plurality of pressures and measuring an amount of uptake of the gas by the porous adsorbent after the porous adsorbent is allowed to come to thermal equilibrium to a selected temperature for each of the plurality of pressures.

7. The method of claim 6, wherein the isosteric enthalpy of adsorption is computed using the equation $$-\Delta H_{ads}(n_a) = -T\left(\frac{\partial P}{\partial T}\right)_{n_a} (\Delta v_{ads}),$$

where $-\Delta H_{ads}(n_a)$ is an isosteric enthalpy of adsorption at a specific uptake amount $n_a$, T is temperature, P is pressure, $$\left(\frac{\partial P}{\partial T}\right)_{n_a}$$

is a slope of a relationship between pressure and temperature for adsorption of the gas by the porous adsorbent evaluated at the specific uptake amount $n_a$ and $\Delta v_{ads}$ is a change in molar volume of the gas upon adsorption.

8. The method of claim 1, further comprising a step of empirically characterizing isosteric enthalpy of adsorption values for a range of pore size distributions for the porous adsorbent or further comprising a step of empirically characterizing isosteric enthalpy of adsorption values for a range of porous adsorbents having different chemical compositions.

9. The method of claim 1, wherein the step of determining the first pore size distribution comprises calculating a density functional theory model of the porous adsorbent for a number of candidate pore size distributions or calculating a Lennard-Jones potential for a system comprising the porous adsorbent and the gas; or wherein the step of determining the first pore size distribution comprises using an empirical method selected from the group consisting of MP (micropore) method, $\alpha_s$-method, DR (Dubinin-Radushkevich) method, DA (Dubinin-Astakhov) method, Dubinin-Stoekli method, Horvah-Kawazoe method, BJH method and Nguyen-DO (ND) method and any combination thereof.

10. The method of claim 1, wherein the gas comprises one or more of: $H_2O$, $H_2$, $CH_4$, $C_2H_4$, $C_2H_2$, $C_3H_8$, $C_3H_6$, $C_4H_{10}$, $C_5H_{12}$, $C_5H_{10}$, $C_6H_{14}$, $C_6H_{12}$, $C_6H_6$, $CH_3OH$, $C_2H_5OH$, $C_3H_7OH$, $CH_3Cl$, $CH_2Cl_2$, $CHCl_3$, $CCl_4$, HCl, HF, $BH_3$, $B_2H_6$, $BF_3$, $BCl_3$, HCOOH, $O_2$, $O_3$, HOOH, $H_2S$, any deuterated form of these, any partially deuterated form of these, $CO_2$, CO, $N_2$, CN, $N_2O$, Xe, Kr, $SiH_4$, $CF_4$, $CCl_4$, $SF_6$, $SiF_4$, $CS_2$, natural gas and any combination of these.

11. The method of claim 1, wherein the gas comprises a first gas and one or more additive gases and wherein adsorption of the one or more additive gases onto the exposed surface of the porous adsorbent provides the constant or increasing isosteric enthalpy of adsorption as a function of uptake of the gas.

12. The method of claim 11, wherein the first gas comprises methane and the one or more additive gases are selected from the group consisting of $C_2H_6$, $C_2H_4$, $C_2H_2$, $C_3H_8$, $C_3H_6$, $C_4H_{10}$, $C_5H_{12}$, $C_5H_{10}$, $C_6H_{14}$, $C_6H_{12}$, $C_6H_6$, CO, $CO_2$, $H_2O$, $H_2$, Xe, Kr, $B_2H_6$, $SiH_4$, $CF_4$, $CCl_4$, $SF_6$, $SiF_4$ and $CS_2$.

13. The method of claim 1, wherein the contacting step comprises contacting the exposed surface of the porous adsorbent to the gas at a temperature within the range of −169° C. to 125° C.; or wherein the contacting step comprises contacting the exposed surface of the porous adsorbent to the gas at a temperature greater than a critical temperature of the gas, at a pressure greater than the critical pressure of the gas or at both a temperature greater than a critical temperature of the gas and a pressure greater than the critical pressure of the gas; or wherein the contacting step comprises contacting the exposed surface of the porous adsorbent to the gas at a pressure greater than atmospheric pressure; or wherein the contacting step comprises contacting the exposed surface of the porous adsorbent to the gas at a pressure greater than or equal to 1 MPa.

14. The method of claim 1, wherein the porous adsorbent has the first chemical composition comprising elements selected from the group consisting of hydrogen, beryllium, boron, carbon, nitrogen, oxygen, a halogen, an alkali metal, an alkaline earth element, a noble metal and any combination of these.

15. The method of claim 1, wherein the first chemical composition comprises a carbonaceous material.

16. The method of claim 1, wherein the first chemical composition comprises graphitic carbon, graphene, HOPG, amorphous carbon, carbon black, coke, carbon nanotubes, fullerenes, activated carbon, superactivated carbon, carbon aerogel, template carbon, intercalated graphite, $sp^2$-hybridized carbon, zeolite templated carbon, porous aluminosilicate-templated carbon, mesoporous silica-templated carbon or any combinations of these.

17. The method of claim 1, wherein the porous adsorbent comprises a microporous material or a mesoporous material.

18. The method of claim 1, wherein the first pore size distribution comprises a unimodal distribution with a mean pore cross sectional dimension selected from the range of 0.4 nm to 2.6 nm or wherein the first pore size distribution comprises a unimodal distribution with a pore cross sectional dimension standard deviation less than 0.5 nm.

19. The method of claim 1, wherein the first pore size distribution comprises a mean inter pore spacing dimension selected from the range of 1 nm to 5 nm or wherein the first pore size distribution comprises an inter pore spacing dimension standard deviation less than 0.5 nm.

20. The method of claim 1, wherein the porous adsorbent has a specific surface area selected from the range of 100 $m^2$ $g^{-1}$ to 6000 $m^2$ $g^{-1}$.

21. The method of claim 1, wherein the pore structures of the porous adsorbent are provided in an ordered network, wherein the ordered network is a connected or unconnected lattice comprising channels in one or more of the following patterns: 1D (unconnected), 2D simple square, 2D hexagonal, 2D other, 3D simple cubic, 3D hexagonal, 3D other, a connected or unconnected lattice of slits in one or more patterns selected from the group consisting of 2D (unconnected) and 3D regularly connected slits.

22. The method of claim 1, wherein the first chemical composition comprises a zeolite-templated carbon, wherein the gas comprises methane and wherein the first pore size distribution comprises a mean pore cross sectional selected from the range of 0.8 nm to 1.4 nm and a pore cross sectional dimension standard deviation less than 0.3 nm.

23. The method of claim 1, wherein at least a portion of the pore structures confine gas adsorbed onto the exposed surface of the porous adsorbent in two dimensions or wherein at least a portion of the pore structures confine gas adsorbed onto the exposed surface of the porous adsorbent in three dimensions; and wherein at least a portion the pore structures comprise a channel structure or wherein at least a portion the pore structures comprise, at least in part, a box structure, a cage structure or a perforated spherical structure.

24. The method of claim 1, wherein the constant or increasing isosteric enthalpy of adsorption varies between 2 kJ $mol^{-1}$ and 48 kJ $mol^{-1}$, or wherein the isosteric enthalpy exhibits an increase amount between 0.2 kJ $mol^{-1}$ and 6 kJ $mol^{-1}$.

25. The method of claim 1, wherein the constant or increasing isosteric enthalpy of adsorption as a function of uptake of the gas occurs at a fractional coverage of the exposed surface selected from the range of 10% to 50% or from the range of 0% to 60% or wherein the constant or increasing isosteric enthalpy of adsorption as a function of uptake occurs for pressures of the gas selected from the range of 0.01 MPa to 10 MPa or wherein the constant or increasing isosteric enthalpy of adsorption as a function of uptake occurs for temperatures of the gas selected from the range of −70° C. to 0° C. or selected from the range of −50° C. to 25° C.

26. The method of claim 1, wherein the constant or increasing isosteric enthalpy of adsorption provides for reversible uptake or release of the gas adsorbed onto the exposed surface as the pressure is varied.

27. The method of claim 1, wherein the gas is adsorbed onto the exposed surface to an absolute uptake amount or excess uptake amount selected from the range of 0.5 mmol $g^{-1}$ to 50 mmol $g^{-1}$.

28. The method of claim 1, wherein a deliverable gravimetric gas capacity of the porous adsorbent is selected from the range of 5 to 50 weight percent or selected from the range of 1 to 20 weight percent.

29. A method of making a porous adsorbent having a first chemical composition, the method comprising:
   determining a first pore size distribution for the porous adsorbent, wherein the first pore size distribution provides a constant or increasing isosteric enthalpy of adsorption as a function of uptake of the gas on an exposed surface of the porous adsorbent;
   providing a porous template material comprising a first plurality of ordered pore structures having a second pore size distribution;
   exposing the porous template material to a first chemical composition precursor to create a porous template material and first chemical composition precursor mixture;
   converting the first chemical composition precursor to the first chemical composition, thereby creating a porous template material and first chemical composition mixture; and
   removing the porous template material from the porous template material and first chemical composition mixture, thereby creating the porous adsorbent.

30. A stored gas composition comprising a porous adsorbent and a gas adsorbed on an exposed surface of the porous adsorbent, wherein the porous adsorbent has a first chemical composition and a first plurality of ordered pore structures characterized by a first pore size distribution, wherein the first pore size distribution provides a constant or increasing isosteric enthalpy of adsorption as a function of uptake of the gas on the exposed surface of the porous adsorbent for a pressure of the gas exposed to the porous adsorbent selected from the range of 1 MPa to 12 MPa and at a temperature the range of −169° C. to 125° C.; wherein the gas is adsorbed on the exposed surface of the porous adsorbent to an absolute uptake amount selected from the range of 0.5 mmol $g^{-1}$ to 50 mmol $g^{-1}$.

* * * * *